(12) United States Patent
Reed et al.

(10) Patent No.: US 12,233,160 B2
(45) Date of Patent: Feb. 25, 2025

(54) DRIED NANOPARTICLE COMPOSITIONS

(71) Applicant: HDT Bio Corp., Seattle, WA (US)

(72) Inventors: Steven Gregory Reed, Bellevue, WA (US); Amit Praful Khandhar, Issaquah, WA (US); Darrick Albert Carter, Seattle, WA (US)

(73) Assignee: HDT Bio Corp., Seattle, WA (US)

( * ) Notice: Subject to any disclaimer, the term of this patent is extended or adjusted under 35 U.S.C. 154(b) by 0 days.

(21) Appl. No.: 18/609,128

(22) Filed: Mar. 19, 2024

(65) Prior Publication Data

US 2024/0216274 A1 Jul. 4, 2024

Related U.S. Application Data

(63) Continuation of application No. PCT/US2022/013508, filed on Jan. 24, 2022.

(60) Provisional application No. 63/297,449, filed on Jan. 7, 2022, provisional application No. 63/247,172, filed on Sep. 22, 2021.

(51) Int. Cl.
| | |
|---|---|
| A61K 9/107 | (2006.01) |
| A61K 9/19 | (2006.01) |
| A61K 9/51 | (2006.01) |
| A61K 31/7105 | (2006.01) |
| A61K 31/711 | (2006.01) |
| A61K 47/06 | (2006.01) |
| A61K 47/12 | (2006.01) |
| A61K 47/26 | (2006.01) |
| B82Y 5/00 | (2011.01) |

(52) U.S. Cl.
CPC ........... *A61K 9/1075* (2013.01); *A61K 9/19* (2013.01); *A61K 9/5115* (2013.01); *A61K 31/7105* (2013.01); *A61K 31/711* (2013.01); *A61K 47/06* (2013.01); *A61K 47/12* (2013.01); *A61K 47/26* (2013.01); *B82Y 5/00* (2013.01)

(58) Field of Classification Search
CPC ...... A61K 9/1075; A61K 9/19; A61K 9/5115; A61K 31/7105; A61K 31/711; A61K 47/06; A61K 47/12; A61K 47/26; B82Y 5/00
See application file for complete search history.

(56) References Cited

U.S. PATENT DOCUMENTS

| | | |
|---|---|---|
| 7,045,335 B2 | 5/2006 | Smith |
| 7,425,337 B2 | 9/2008 | Smith |
| 8,709,441 B2 | 4/2014 | Rayner |
| 8,734,832 B2 | 5/2014 | O'Hagan et al. |
| 8,853,179 B2 | 10/2014 | Mauro |
| 9,295,646 B2 | 3/2016 | Brito et al. |
| 9,555,136 B2 | 1/2017 | Khandhar et al. |
| 9,655,845 B2 | 5/2017 | Brito |
| 10,238,733 B2 | 3/2019 | Brito |
| 10,307,374 B2 | 6/2019 | Brito |
| 11,026,890 B2 | 6/2021 | Brito |
| 11,083,786 B2 | 8/2021 | Kamrud |
| 11,135,287 B2 | 10/2021 | Brito |
| 11,141,377 B2 | 10/2021 | Fox |
| 11,318,213 B2 | 5/2022 | Khandhar |
| 11,364,310 B2 | 6/2022 | Kamrud |
| 11,376,335 B2 | 7/2022 | Khandhar |
| 11,406,699 B2 | 8/2022 | Kehn-Hall |
| 11,433,142 B2 | 9/2022 | Khandhar |
| 11,458,209 B2 | 10/2022 | Khandhar |
| 11,534,497 B2 | 12/2022 | Khandhar |
| 2006/0128011 A1 | 6/2006 | Zhu |
| 2009/0252721 A1 | 10/2009 | Buschmann |
| 2012/0156251 A1 | 6/2012 | Brito |
| 2013/0195751 A1 | 8/2013 | Hahn |
| 2013/0202707 A1 | 8/2013 | Ali |
| 2016/0000886 A1 | 1/2016 | Parker |
| 2016/0201067 A1 | 7/2016 | Ataullakhanov |
| 2017/0189368 A1 | 7/2017 | Troiano |
| 2018/0008694 A1 | 1/2018 | Ciaramella |
| 2018/0104325 A1 | 4/2018 | Gale, Jr. |
| 2018/0147298 A1 | 5/2018 | Besin |
| 2018/0153848 A1 | 6/2018 | Chen |
| 2018/0207295 A1 | 7/2018 | Fotin-Mleczek |
| 2019/0015501 A1 | 1/2019 | Ciaramella |
| 2019/0274968 A1 | 9/2019 | Weissman |
| 2020/0006973 A1 | 1/2020 | Petersen |
| 2020/0069599 A1 | 3/2020 | Smith |
| 2020/0123573 A1 | 4/2020 | Kamrud |
| 2020/0157571 A1 | 5/2020 | Nakanishi |
| 2020/0224174 A1 | 7/2020 | Irvine |

(Continued)

FOREIGN PATENT DOCUMENTS

| | | |
|---|---|---|
| WO | 2001021810 A1 | 3/2001 |
| WO | 2002080982 A2 | 10/2002 |

(Continued)

OTHER PUBLICATIONS

"Gennova's mRNA vaccine to come in powder form; will stay stable at 2-8° C." Business Standard. Sep. 13, 2021 02:56 IST.
Brinckerhoff, L. H., et al., "Melanoma vaccines" Current Opinion in Oncology: Mar. 2000 —vol. 12—Issue 2—p. 163-173.

(Continued)

*Primary Examiner* — Robert S Cabral
(74) *Attorney, Agent, or Firm* — Greenberg Traurig, LLP

(57) ABSTRACT

Provided herein are dried compositions and methods for preparing such compositions for use in delivery of a nucleic acid to a subject. The dried composition may comprise a lipid carrier, wherein the lipid carrier is a nanoemulsion comprising a hydrophobic core, optionally one or more inorganic nanoparticles and one or more lipids, one or more nucleic acid, and at least one cryoprotectant. Methods of using these dried compositions for treatment are also provided.

47 Claims, 27 Drawing Sheets

Specification includes a Sequence Listing.

(56) References Cited

U.S. PATENT DOCUMENTS

| | | |
|---|---|---|
| 2020/0230056 A1 | 7/2020 | Fox |
| 2020/0297834 A1 | 9/2020 | Kehn-Hall |
| 2020/0368344 A1 | 11/2020 | Ciaramella |
| 2020/0370052 A1 | 11/2020 | Wilson |
| 2021/0128583 A1 | 5/2021 | Zhang |
| 2021/0283242 A1 | 9/2021 | Hutchins |
| 2021/0290752 A1 | 9/2021 | Sullivan |
| 2021/0290756 A1 | 9/2021 | Sullivan |
| 2021/0330781 A1 | 10/2021 | Kamrud |

FOREIGN PATENT DOCUMENTS

| | | |
|---|---|---|
| WO | 2005107760 A1 | 11/2005 |
| WO | 2007024826 A2 | 3/2007 |
| WO | 2008124647 A2 | 10/2008 |
| WO | 2008153541 A1 | 12/2008 |
| WO | WO2009049083 | 4/2009 |
| WO | 2010141861 A1 | 12/2010 |
| WO | WO 2011/156761 | 12/2011 |
| WO | 2014042780 A1 | 3/2014 |
| WO | 2015103167 A2 | 7/2015 |
| WO | 2017200852 A1 | 11/2017 |
| WO | 2017200957 A1 | 11/2017 |
| WO | 2017205225 A2 | 11/2017 |
| WO | 2017210364 A1 | 12/2017 |
| WO | 2017218704 A1 | 12/2017 |
| WO | WO2018022957 | 2/2018 |
| WO | 2018/044028 | 3/2018 |
| WO | 2018053294 A1 | 3/2018 |
| WO | WO 2018/147710 | 8/2018 |
| WO | 2018232257 | 12/2018 |
| WO | WO20182322257 | 12/2018 |
| WO | WO 2019/152884 | 8/2019 |
| WO | 2020132279 A1 | 6/2020 |
| WO | 2020/243115 | 12/2020 |
| WO | 2020254804 A1 | 12/2020 |
| WO | 2021021605 A1 | 2/2021 |
| WO | 2021076630 A1 | 4/2021 |
| WO | WO 2021/067480 | 4/2021 |
| WO | WO 2021/072112 | 4/2021 |
| WO | WO 2021/163536 | 8/2021 |
| WO | 2021178886 A1 | 9/2021 |
| WO | 2021183564 A1 | 9/2021 |
| WO | 2021194672 A1 | 9/2021 |
| WO | WO 2021/194672 | 9/2021 |
| WO | 2021210686 A1 | 10/2021 |
| WO | WO 2022/051022 | 3/2022 |
| WO | 2022136952 A1 | 6/2022 |
| WO | 2023286076 A1 | 1/2023 |
| WO | 2023026301 A1 | 3/2023 |
| WO | 2023049636 A1 | 3/2023 |
| WO | 2023049636 A2 | 3/2023 |
| WO | 2023056202 A2 | 4/2023 |

OTHER PUBLICATIONS

Brito, L.. A.. , et al., A cationic nanoemulsion for the delivery of next-generation RNA vaccines. Mol Ther. 2014;22(12):2118-2129. doi:10.1038/mt.2014.133.

Brocato, R. L., et al., Protective efficacy of a SARS-COV-2 DNA vaccine in wild-type and immunosuppressed Syrian hamsters. NPJ Vaccines 6, 16 (2021). https://doi.org/10.1038/s41541-020-00279-z.

Brown, C. M., et al. Outbreak of SARS-COV-2 Infections, Including COVID-19 Vaccine Breakthrough Infections, Associated with Large Public Gatherings—Barnstable County, Massachusetts, Jul. 2021. MMWR Morb Mortal Wkly Rep 2021;70:1059-1062.

Corbett, K. S., et al., "Evaluation of the mRNA-1273 Vaccine against SARS-COV-2 in Nonhuman Primates" N Engl J Med. Oct. 1, 20205;383(16): 1544-1555. doi: 10.1056/NEJMoa2024671.

Corman, V. C., et al., Detection of 2019 novel coronavirus (2019-nCOV) by real-time RT-PCR. Euro Surveill. 2020;25 (3), https://doi.org/10.2807/1560-7917.ES.2020.25.3.2000045.

CustomBiotech Online Development Exchange (CODE), Beyond COVID: The Future of mRNA technology, Webinar held Thursday, Nov. 11, 2021, https://dianews.roche.com/CustomBiotech-Webinar-2021.html.

Edara, V., et al., Infection and Vaccine-Induced Neutralizing-Antibody Responses to the SARS-COV-2 B. 1.617 Variants. N Engl J Med. Aug. 1, 20212;385(7):664-666. doi: 10.1056/NEJMc2107799. Epub Jul. 7, 2021. PMID: 34233096; Pmcid: PMC8279090.

Erasmus, J. H., A Nanostructured Lipid Carrier for Delivery of Replicating Viral RNA Provides Single, Low-Dose Protection against Zika, Molecular Therapy, vol. 26, No. 10. pages 2507-2522.

Erasmus, J. H., et al., "An Alphavirus-derived replicon RNA vaccine induces SARS-COV-2 neutralizing antibody and T cell responses in mice and nonhuman primates" Science Translational Medicine, Aug. 5, 2020, vol. 12, Issue 555.

Erasmus, J.H et al., "Single-dose Replicating RNA Vaccine Induces Neutralizing Antibodies Against SARS-COV-2 in Nonhuman Primates", bioRxiv, 28 pages.

Erasmus, J.H., "An Alphavirus-derived replicon RNA vaccine induces SARS-COV-2 Neutralizing Antibody and T-cell Responses in Mice and Nonhuman Primates", Science Translational Medicine, vol. 12, No. 555.

Erasmus, J.H., et al., Intramuscular Delivery of Replicon RNA Encoding ZIKV-117 Human Monoclonal Antibody Protects against Zika Virus Infection. Mol Ther - Methods Clin Dev. 2020; 18:402-414. PMID: 32695842.

File No: BIO/CT/U.S. Appl. No. 20/000,182, Ct No. CT-Feb. 2021 Government of India Directorate General of Health Services Central Drugs Standard Control Organization (Biological Division), Form CT-06 Permission To Conduct Clinical Trial of New Drug or Investigational New Drug, Jan. 25, 2021, 3 pages.

File No: BIO/CT/U.S. Appl. No. 21/000,105, Ct No. CT-28/2021 Government of India Directorate General of Health Services Central Drugs Standard Control Organization (Biological Division), Form CT-06 Permission To Conduct Clinical Trial of New Drug or Investigational New Drug, Aug. 22, 2021, 3 pages.

Fischer, Robert J., et al. "ChAdOx1 nCOV-19 (AZD1222) protects Syrian hamsters against SARS-CoV-2 B.1.351 and B.1.1.7." bioRxiv : the preprint server for biology 2021.03.11.435000. Jun. 30, 2021, doi:10.1101/2021.03.11.435000. Preprint.

Geall, Andrew J., et al. "Nonviral delivery of self-amplifying RNA vaccines." PNAS. vol. 109. No 36, pp. 14604-14609 (2012).

Gilchuk, P., et al., "Integrated pipeline for the accelerated discovery of antiviral antibody therapeutics" Nat Biomed Eng. 2020;4(11):1030-1043. PMID: 32747832.

Hörner, C., et al., A highly immunogenic and effective measles virus-based Th1-biased COVID-19 vaccine, Proceedings of the National Academy of Sciences Dec. 2020, 117 (51) 32657-32666; DOI: 10.1073/pnas.2014468117.

Hou, X., et al., Lipid nanoparticles for mRNA delivery. Nat Rev Mater (2021). https://doi.org/10.1038/s41578-021-00358-0.

International Search Report and Written Opinion for PCT/US2021/019103 issued Sep. 30, 2021.

Jain, T.K., et al., Iron Oxide Nanoparticles for Sustained Delivery of Anticancer Agents, Molecular Pharmaceutics, American Chemical Society, 2 (3), 194-205, 2005.

Kalnin, K.V., et al., Immunogenicity and efficacy of mRNA COVID-19 vaccine MRT5500 in preclinical animal models. npj Vaccines 6, 61 (2021). https://doi.org/10.1038/s41541-021-00324-5.

Kurup, D. et al., Inactivated rabies virus vectored SARS-CoV-2 vaccine prevents disease in a Syrian hamster model, PLOS Pathogens 17(3): e1009383. https://doi.org/10.1371/journal.ppat.1009383.

Li, Q. et al., "A Review of the Structure, Preparation, and Application of NLCs, PNPs and PLNs", Nanomaterials, vol. 7, No. 6, p. 1-25.

Limbach, P A et al. "Summary: the modified nucleosides of RNA." Nucleic acids research vol. 22,12 (1994): 2183-96. doi: 10.1093/nar/22.12.2183.

(56) References Cited

OTHER PUBLICATIONS

Lopez Bernal, J, et al., Effectiveness of Covid-19 Vaccines against the B.1.617.2 (Delta) Variant. N Engl J Med. Aug. 12, 2021;385(7):585-594. doi: 10.1056/NEJMoa2108891. Epub Jul. 21, 2021. PMID: 34289274; PMCID: PMC8314739.

Machado, B.A.S., et al., The Importance of RNA-Based Vaccines in the Fight against COVID-19: An Overview. Vaccines (Basel). Nov. 17, 2021;9(11):1345. doi: 10.3390/vaccines9111345. PMID: 34835276; PMCID: PMC8623509.

Mckay, P. F., et al., Self-amplifying RNA SARS-COV-2 lipid nanoparticle vaccine candidate induces high neutralizing antibody titers in mice. Nat Commun. Jul. 9, 2020;11(1):3523. doi: 10.1038/s41467-020-17409-9. PMID: 32647131; PMCID: PMC7347890.

Mercado, N.B., et al., "Single-shot Ad26 vaccine protects against SARS-CoV-2 in rhesus macaques" Nature. Oct. 2020;586(7830):583-588. doi: 10.1038/s41586-020-2607-z. Epub Jul. 30, 2020. Erratum in: Nature. Feb. 2021;590(7844): E25. PMID: 32731257; PMCID: PMC7581548.

Meyer, B., et al., Characterising proteolysis during SARS-CoV-2 infection identifies viral cleavage sites and cellular targets with therapeutic potential. Nat Commun. Sep. 21, 2021;12(1):5553. doi: 10.1038/s41467-021-25796-w. PMID: 34548480; PMCID: PMC8455558.

Mohandas, S., et al., Immunogenicity and protective efficacy of BBV152, whole virion inactivated SARS-CoV-2 vaccine candidates in the Syrian hamster model. iScience. Feb. 19, 2021;24(2):102054. doi: 10.1016/j.isci.2021.102054. Epub Jan. 9, 2021. PMID: 33521604; PMCID: PMC7829205.

Planas, D., et al., Reduced sensitivity of SARS-CoV-2 variant Delta to antibody neutralization. Nature. Aug. 2021;596(7871):276-280. doi: 10.1038/s41586-021-03777-9. Epub Jul. 8, 2021. PMID: 34237773.

Rauch, S, et al., mRNA-based SARS-CoV-2 vaccine candidate CVnCoV induces high levels of virus-neutralising antibodies and mediates protection in rodents. NPJ Vaccines. Apr. 16, 2021;6(1):57. doi: 10.1038/s41541-021-00311-w. PMID: 33863911; PMCID: PMC8052455.

Sheikh, A, et al., SARS-CoV-2 Delta VOC in Scotland: demographics, risk of hospital admission, and vaccine effectiveness. Lancet. Jun. 26, 2021;397(10293):2461-2462. doi: 10.1016/S0140-6736(21)01358-1. Epub Jun. 14, 2021. PMID: 34139198; PMCID: PMC8201647.

Shen, X, et al., SARS-CoV-2 variant B.1.1.7 is susceptible to neutralizing antibodies elicited by ancestral spike vaccines. Cell Host Microbe. Apr. 14, 2021;29(4):529-539.e3. doi: 10.1016/j.chom.2021.03.002. Epub Mar. 5, 2021. PMID: 33705729; PMCID: PMC7934674.

Szurgot, I., et al., DNA-launched RNA replicon vaccines induce potent anti-SARS-CoV-2 immune responses in mice. 2021 Scientific Reports. 11. 10.1038/s41598-021-82498-5.

Van Der Lubbe, J. E. M., et al., Ad26.COV2.S protects Syrian hamsters against G614 spike variant SARS-CoV-2 and does not enhance respiratory disease. NPJ Vaccines. Mar. 19, 2021;6(1):39. doi: 10.1038/s41541-021-00301-y. PMID: 33741993; PMCID: PMC7979827.

Van Doremalen, N., et al. Immunogenicity of low dose prime-boost vaccination of mRNA vaccine CV07050101 in non-human primates. bioRxiv [Preprint]. Jul. 7, 2021:2021.07.07.451505. doi: 10.1101/2021.07.07.451505. Update in: Viruses. Aug. 19, 2021;13(8): PMID: 34268507; PMCID: PMC8282095.

Van Doremalen, N., et al., ChAdOx1 nCOV-19 vaccine prevents SARS-CoV-2 pneumonia in rhesus macaques. Nature. Oct. 2020;586(7830):578-582. doi: 10.1038/s41586-020-2608-y. Epub Jul. 30, 2020. Erratum in: Nature. Feb. 2021;590(7844): E24. PMID: 32731258; PMCID: PMC8436420.

V'Kovski, P, et al., "Coronavirus biology and replication: implications for SARS-CoV-2". Nature Reviews. (Mar. 2021). Microbiology. 19 (3): 155-170. doi: 10.1038/s41579-020-00468-6. PMC 7592455. PMID 33116300.

Wang, P., et al., Antibody resistance of SARS-CoV-2 variants B.1.351 and B.1.1.7. Nature. May 2021;593(7857):130-135. doi: 10.1038/s41586-021-03398-2. Epub Mar. 8, 2021. PMID: 33684923.

Wang, Z., et al., Naturally enhanced neutralizing breadth against SARS-CoV-2 one year after infection. Nature. Jul. 2021;595(7867):426-431. doi: 10.1038/s41586-021-03696-9. Epub Jun. 14, 2021. PMID: 34126625; PMCID: PMC8277577.

Wu, C, et al. "Analysis of therapeutic targets for SARS-CoV-2 and discovery of potential drugs by computational methods," Acta Pharmaceutica Sinica (May 2020). B. 10 (5): 766-788. doi: 10.1016/j.apsb.2020.02.008. PMC 7102550. PMID 32292689, the contents of which are hereby incorporated by reference in their entirety.

Yinda, C. K., et al., Prior aerosol infection with lineage A SARS-CoV-2 variant protects hamsters from disease, but not reinfection with B.1.351 SARS-CoV-2 variant. Emerg Microbes Infect. Dec. 2021;10(1):1284-1292. doi: 10.1080/22221751.2021.1943539. PMID: 34120579; PMCID: PMC8238069.

Yu, Jingyou et al. "DNA vaccine protection against SARS-CoV-2 in rhesus macaques." Science (New York, N.Y.) vol. 369,6505 (2020): 806-811. doi:10.1126/science.abc6284.

Zhang, Y., et al., A second functional furin site in the SARS-CoV-2 spike protein. Emerg Microbes Infect. Dec. 3, 2021:1-35. doi: 10.1080/22221751.2021.2014284. Epub ahead of print. PMID: 34856891.

Zhou, D., et al., Evidence of escape of SARS-CoV-2 variant B.1.351 from natural and vaccine-induced sera. Cell. Apr. 29, 2021;184(9):2348-2361.e6. doi: 10.1016/j.cell.2021.02.037. Epub Feb. 23, 2021. PMID: 33730597; PMCID: PMC7901269.

Zost, S.J., et al., Rapid isolation and profiling of a diverse panel of human monoclonal antibodies targeting the SARS-CoV-2 spike protein. Nat Med. 2020;26(9):1422-1427. PMID: 32651581.

International Search Report issued Jun. 29, 2023 in PCT/US2022/076787.

International Search Report issued Jun. 7, 2023 in PCT/US2022/076304.

Pin, Elisa, et al. "Identification of a Novel Autoimmune Peptide Epitope of Prostein in Prostate Cancer." Journal of Proteome Research 16.1 (2017): 204-216.

Agnihothram, S., et al., "Development of a Broadly Accessible Venezuelan Equine Encephalitis Virus Replicon Particle Vaccine Platform" J Virol. May 14, 2018;92(11):e00027-18. doi: 10.1128/JVI.00027-18.

Anderluzzi, G., et al., "Investigating the Impact of Delivery System Design on the Efficacy of Self-Amplifying RNA Vaccines" Vaccines (Basel). May 8, 2020;8(2):212. doi: 10.3390/vaccines8020212.

Bazhan, S., et al., "Immunogenicity and Protective Efficacy of Influenza A DNA Vaccines Encoding Artificial Antigens Based on Conservative Hemagglutinin Stem Region and M2 Protein in Mice." Vaccines vol. 8,3 448. Aug. 9, 2020, doi:10.3390/vaccines8030448.

Boettler, T., et al., "SARS-CoV-2 vaccination can elicit a CD8 T-cell dominant hepatitis" J Hepatol. Sep. 2022;77(3):653-659. doi: 10.1016/j.jhep.2022.03.040.

Chiu, C.Y.H., et al., "Association of antibodies to Plasmodium falciparum reticulocyte binding protein homolog 5 with protection from clinical malaria" Front Microbiol. Jun. 30, 2014;5:314. doi: 10.3389/fmicb.2014.00314.

Deo, S., et al. "Evaluation of self-amplifying mRNA platform for protein expression and genetic stability: Implication for mRNA therapies." Biochemical and Biophysical Research Communications 680 (2023): 108-118.

Dewey, E.C., et al., "Programming of RIG-I Signaling Through Co-Factor Interactions," The Journal of Immunology 96 (1 Suppl):203, May 2016, 4 pages.

Du, L., et al., "The Spike Protein of SARS-CoV—A Target for Vaccine and Therapeutic Development", Nat Rev Microbiol 7, 226-236 (2009). https://doi.org/10.1038/nrmicro2090.

Duerrwald, R., et al., "Influenza A virus (A/swine/Bueren/5439/2006(H3N2)) segment 4 hemagglutinin (HA) gene, complete cds". Genbank entry (online). National Center for Biotechnology Information. URL: Https://www.ncbi.nlm.nih.gov/nucleotide/MK362039.1J. Jan. 31, 2020; pp. 1-2.

Erasmus, J.A., et al., "A Nanostructured Lipid Carrier for Delivery of a Replicating Viral RNA Provides Single, Low-Dose Protection

(56) References Cited

OTHER PUBLICATIONS against Zika", Mol Ther. Oct. 3, 2018;26(10):2507-2522. doi: 10.1016/j.ymthe.2018.07.010. Epub Aug. 2, 2018. PMID: 30078765; PMCID: PMC6171036.

Felgner, Philip L., et al. "Lipofection: a highly efficient, lipid-mediated DNA-transfection procedure." Proceedings of the National Academy of Sciences 84.21 (1987): 7413-7417.

Fleeton, M. N., et al., "Self-Replicative RNA Vaccines Elicit Protection Against Influenza A Virus, Respiratory Syncytial Virus, and a Tickborne Encephalitis Virus", The Journal of Infectious Diseases, vol. 183, Issue 9, May 1, 2001, pp. 1395-1398, https://doi.org/10.1086/319857.

Fox, C.B., "Squalene emulsions for parenteral vaccine and drug delivery" Molecules. Sep. 1, 2009;14(9):3286-312. doi: 10.3390/molecules14093286.

Gao, Y., et al, "Structure of the RNA-dependent RNA polymerase from COVID-19 virus" Science. May 15, 2020;368(6492):779-782. doi: 10.1126/science.abb7498.

Gehardt, Alana, et al., "A flexible, thermostable nanostructured lipid carrier platform for RNA vaccine delivery" Mol Ther Methods Clin Dev. Jun. 9, 2022;25:205-214. doi: 10.1016/j.omtm.2022.03.009.

Hartmann, G. "Chapter 4: Nucleic Acid Immunity," in F. Alt (ed.), "Advances in Immunology," 133:121-169, 2017.

Hatmal, M.M., et al., "Comprehensive Structural and Molecular Comparison of Spike Proteins of SARS-CoV-2, SARS-CoV and MERS-CoV, and Their Interactions with ACE2" Cells Dec. 8, 2020;9(12):2638. doi: 10.3390/cells9122638.

Hawman, D. W. et al., "SARS-CoV2 variant-specific replicating RNA vaccines protect from disease and pathology and reduce viral shedding following challenge with heterologous SARS-CoV2 variants of concern" bioRxiv [Preprint]. Dec. 13, 2021:2021.12.10.472134. doi: 10.1101/2021.12.10.472134 bioRxiv 2021.12.10.472134; doi: https://doi.org/10.1101/2021.12.10.472134.

Heinz, F.X., and Stiasny, K., "Distinguishing features of current COVID-19 vaccines: knowns and unknowns of antigen presentation and modes of action" NPJ Vaccines. Aug. 16, 2021;6(1):104. doi: 10.1038/s41541-021-00369-6.

Huang, Y., et al., "Structural and functional properties of SARS-CoV-2 spike protein: potential antivirus drug development for COVID-19" Acta Pharmacol Sin 41, 1141-1149 (2020). https://doi.org/10.1038/s41401-020-0485-4.

International Search Report issued Jun. 6, 2022 in PCT/US2022/13513.

International Search Report issued Jun. 8, 2022 in PCT/US2022/013516.

International Search Report issued Jun. 14, 2022 in PCT/US2022/13508.

International Search Report issued in PCT/US2023/060225 dated Jul. 28, 2023.

International Search Report issued Jun. 6, 2022 in PCT/US2022/013513.

International Search Report issued Jun. 8, 2023 in PCT/US2022/076821.

Kautz, T. F., et al., "Low-fidelity Venezuelan equine encephalitis virus polymerase mutants to improve live-attenuated vaccine safety and efficacy" Virus Evol.:4(1); pp. 1-14, Mar. 6, 2018;. doi: 10.1093/ve/vey004.

Kimuira, T, et al., "A localizing nanocarrier formulation enables multi-target immune responses to multivalent replicating RNA with limited systemic inflammation", Molecular Therapy (2023), doi: https://doi.org/10.1016/j.ymthe.2023.06.017.

Kwon, S.M., et al., "In vivo time-dependent gene expression of cationic lipid-based emulsion as a stable and biocompatible non-viral gene carrier" J Control Release. May 22, 2008;128(1):89-97. doi: 10.1016/j.jconrel.2008.02.004. Epub Feb. 19, 2008. Erratum in: J Control Release. Nov. 16, 2009;140(1):74.

Li, X-Y., et al., "Tumor Suppressor Activity of RIG-I," Molecular and Cellular Oncology 1(4):e968016, Dec. 2014.

Marcus, M., et al., "Iron oxide nanoparticles for neuronal cell applications: uptake study and magnetic manipulations", J Nanobiotechnology, vol. 14, Issue 37, May 2016, https://doi.org/10.1186/s12951-016-0190-0.

Maruggi, G., et al., "A self-amplifying mRNA SARS-CoV-2 vaccine candidate induces safe and robust protective immunity in preclinical models" Mol Ther. Jan. 3, 2022:S1525-0016(22)00001-6. doi: 10.1016/j.ymthe.2022.01.001.

Min, J. W., et al., "Hemagglutinin (Influenza A virus (A/Aichi/2/1968(H3N2))]". Genbank entry (online). National Center for Biotechnology Information. Retrieved From The Internet. URL: https://www.ncbi.nlm.nih.gov/protein/AAA43239.1]. Jul. 13, 2006; p. 1.

Pardi, N., et al., "mRNA vaccines—a new era in vaccinology" Nat Rev Drug Discov. Apr. 2018;17(4):261-279. doi: 10.1038/nrd.2017.243. Epub Jan. 12, 2018. PMID: 29326426.

Roeffen, W., et al., "Transmission-blocking activity of antibodies to Plasmodium falciparum GLURP. 10C chimeric protein formulated in different adjuvants" Malar J 14, 443 (2015). https://doi.org/10.1186/s12936-015-0972-0.

Safety And Immunogenicity Of HDT-301 Targeting A SARS-CoV-2 Variant Spike Protein, Sponsor: HDT Bio, posted 11/24/21ClinicalTrials.gov Identifier: NCT05132907 found at https://clinicaltrials.gov/ct2/show/record/NCT05132907?term=hdt+bio&draw=2&rank=1 11 pages.

Schoenmaker, L., et al. "mRNA-lipid nanoparticle COVID-19 vaccines: Structure and stability." International journal of pharmaceutics vol. 601 (2021): 120586. doi: 10.1016/j.ijpharm.2021.120586.

Shu, B., et al., "Structural basis of viral RNA-dependent RNA polymerase catalysis and translocation", Proc Natl Acad Sci USA; 113(28):E4005-14, Jun. 23, 2016 doi: 10.1073/pnas.1602591113.

Singh, K., et al., "Malaria vaccine candidate based on Duffy-binding protein elicits strain transcending functional antibodies in a Phase I trial" NPJ Vaccines. Sep. 28, 2018;3:48. doi: 10.1038/s41541-018-0083-3.

Starmans, L.W.E., et al., "Iron oxide nanoparticle-micelles (ION-micelles) for sensitive (molecular) magnetic particle imaging and magnetic resonance imaging" PLoS One. 2013;8(2):e57335. doi: 10.1371/journal.pone.0057335. Epub Feb. 20, 2013.

Stokes, A., et al., "Nonclinical safety assessment of repeated administration and biodistribution of a novel rabies self-amplifying mRNA vaccine in rats" Regul Toxicol Pharmacol. Jun. 2020;113:104648. doi: 10.1016/j.yrtph.2020.104648.

Teixeira, T. et al., "Cationic nanoemulsions as nucleic acids delivery systems" Int J Pharm. Dec. 20, 2017;534(1-2):356-367. doi: 10.1016/j.ijpharm.2017.10.030.

Tregoning, J. S., et al., "Formulation, inflammation, and RNA sensing impact the immunogenicity of self-amplifying RNA vaccines" Mol Ther Nucleic Acids. Dec. 5, 2022;31:29-42. doi: 10.1016/j.omtn.2022.11.024.

Tregoning, J.S .. "LION: Taming RNA vaccine inflammation" Mol Ther. Aug. 3, 2023:S1525-0016(23)00386-6. doi: 10.1016/j.ymthe.2023.07.006.

Valdivia, L, et al., Solid Lipid Particles for Lung Metastasis Treatment. Pharmaceutics. 2021;13(1):93. Published Jan. 13, 2021. doi:10.3390/pharmaceutics13010093.

Voigt, E.A., et al., "A self-amplifying RNA vaccine against COVID-19 with long-term room-temperature stability" npj Vaccines 7, 136 (2022). https://doi.org/10.1038/s41541-022-00549-y.

Walton, T.E., et al., "Experimental infection of horses with an attenuated Venezuelan equine encephalomyelitis vaccine (strain TC-83)" Infect Immun. May 1972;5(5):750-6. doi: 10.1128/iai.5.5.750-756.1972.

Wu, F., et al., "Severe acute respiratory syndrome coronavirus 2 isolate Wuhan-Hu-1, complete genome" GenBank: MN908947.3, VRL Mar. 18, 2020, available at https://www.ncbi.nlm.nih.gov/nuccore/MN908947.

Gerhardt, Alana, et al. "A thermostable, flexible RNA vaccine delivery platform for pandemic response." bioRxiv (2021):2021-02.

International Search Report issued Jun. 13, 2024 in PCT/US2024/010326.

SEQUENCE LISTING

```
Sequence total quantity: 2
SEQ ID NO: 1            moltype = RNA   length = 1557
FEATURE                 Location/Qualifiers
misc_feature            1..1557
                        note = Description of Artificial Sequence: Synthetic
                         polynucleotide
source                  1..1557
                        mol_type = other RNA
                        organism = synthetic construct
SEQUENCE: 1
atgctcctct tgctccttct cttgggactc cgattgcagc tctctttggg tataattcct    60
gtcgaagaag agaatcccga cttctggaat cgcgaagcgg cagaagcatt gggtgcggca   120
aaaaagctcc aaccggcaca gactgcggcc aagaatctca taattttctt gggtgatggc   180
atgggcgttt ccactgtgac tgcggcacga atcctgaagg gtcaaaagaa ggataaactg   240
ggtccagaga tcccgctggc tatggatagg tttccatacg ttgcgctctc taagacctat   300
aacgtcgata agcatgtacc agactccgga gcgacggcca ctgcttacct ttgtggagtt   360
aaaggtaatt tccaaacaat aggactgagc gcagctgcaa gattcaacca atgcaacacg   420
acaagaggga atgaggtgat ttcagtcatg aatcgagcaa agaaagctgg gaaatccgtt   480
ggcgtggtca ccactacaag agtgcagcat gcatctccag caggaactta cgcccacact   540
gtaaacagaa actggtatag tgacgccgat gttcccgcct ctgcgaggca agagggttgt   600
caagacatcg ctacccagct cataagcaac atggacattg atgtaatact gggtgggggt   660
cggaaataca tgttccggat gggcactccc gatccggagt accggatga ctattcccaa    720
ggaggtacca gattggacgg gaaaaatctt gtccaagaat ggctcgccaa gcggcaggggg  780
gcaaggtacg tgtggaacag gacagaactg atgcaggcaa gcttggatcc aagcgtaacg   840
catcttatgg gtcttttttga acccggtgat atgaaatacg aaatacatcg cgactcaaca  900
ctggacccgt ctctcatgga gatgactgaa gctgccttga ggtgttgag tcggaaccct    960
aggggctttt tcttgttcgt agagggcggg cgaattgacc acggtcatca cgaatctcga  1020
gcgtaccggg cgctcacaga aaccatcatg tttgacgatg ctatcgaacg agcgggtcag  1080
cttacctctg aagaagatac gctctctctt gtcaccgcgg accatagcca tgtttttcc   1140
ttcggtggtt atccgttgcg aggttccagc atattcggcc tcgcgccagg gaaagcccgc  1200
gaccgcaaag cttatacggt gctgctttac ggaaacggcc ctggttacgt ccttaaagac  1260
ggtgcgagac ctgacgtgac ggaatctgaa tccggttctc ccgaatatag acaacagagt  1320
gctgttccgc tggatgaaga gactcatgcg ggagaagatg tagcggtttt tgctaggggg  1380
ccgcaagcac accttgttca tggcgttcag gagcaaactt tcatagccca tgtaatggca  1440
tttgctgcgt gtctcgagcc gtataccgct tgcgatctcg ctccgccggc gggtacaacc  1500
gatgctgccc acccggggta ctcaagagta ggggcagcag ggcgatttga acaaact     1557

SEQ ID NO: 2            moltype = RNA   length = 597
FEATURE                 Location/Qualifiers
misc_feature            1..597
                        note = Description of Artificial Sequence: Synthetic
                         polynucleotide
source                  1..597
                        mol_type = other RNA
                        organism = synthetic construct
SEQUENCE: 2
atgaacagtt tcagtacctc cgcgttcggg ccggttgcct ttagcctggg gcttcttctg    60
gtgctccccg ccgcattccc agcgccggtc ttcacactcg aagatttcgt tggggactgg   120
cgacagacag ccggctacaa cctggaccaa gtccttgaac agggaggtgt gtccagtttg   180
tttcagaatc tcggggtgtc cgtaactccg atccaaagga ttgtcctgag cggtgaaaat   240
gggctgaaga tcgacatcca tgtcatcatc ccgtatgaag gtctgagcgg cgaccaaatg   300
ggccagatcg aaaaaatttt taaggtggtg taccctgtgg atgatcatca ctttaaggtg   360
atcctgcact atggcacact ggtaatcgac ggggttacgc cgaacatgat cgactatttc   420
ggacggccgt atgaaggcat cgccgtgttc gacggcaaaa agatcactgt aacagggacc   480
ctgtggaacg gcaacaaaat tatcgacgag cgcctgatca accccgacgg ctccctgctg   540
ttccgagtaa ccatcaacgg agtgaccggc tggcggctgt gcgaacgcat tctggcg      597
```

DRIED NANOPARTICLE COMPOSITIONS

CROSS-REFERENCE

This application is a continuation of International Application No. PCT/US2022/013508, filed Jan. 24, 2022, which claims the benefit of priority to U.S. Provisional Patent Application No. 63/247,172, filed Sep. 22, 2021, and U.S. Provisional Patent Application No. 63/297,449, filed Jan. 7, 2022, the contents of each of which are incorporated herein by reference in their entirety.

SEQUENCE LISTING

The instant application contains a Sequence Listing which has been submitted electronically in ST 0.26 xml format and is hereby incorporated by reference in its entirety. Said xml copy, created on Mar. 15, 2024, is named 201953-712301-SL.xml and is 5,796 bytes in size.

BACKGROUND

A variety of therapeutic and prophylactic products, including vaccines, are available for diseases. A challenge in the industry for such products is stability. Many of such products must be maintained at cold temperatures, requiring costly cooling units or liquid nitrogen, to retain stability. Thus, there is a need for manufacturing solutions, compositions, and their use, where the therapeutic and prophylactic products are stable with minimal cooling needs or at room temperature.

BRIEF SUMMARY

Provided herein are compositions, wherein the compositions are dried compositions. Provided herein are compositions, wherein the compositions comprise: a lipid carrier, wherein the lipid carrier is a nanoemulsion comprising a hydrophobic core, one or more inorganic nanoparticles and one or more lipids; one or more nucleic acids; and at least one cryoprotectant.

Further provided herein are pharmaceutical compositions, wherein the pharmaceutical compositions comprise: the dried composition reconstituted in a suitable diluent and a pharmaceutically acceptable carrier.

Further provided herein are kits, wherein the kits comprise a pharmaceutical composition comprising the dried composition provided herein; and a delivery system for administration to a subject.

Further provided herein are vaccine delivery systems, wherein the vaccine delivery systems comprise: the pharmaceutical composition and optionally, one or more vaccine adjuvants.

Further provided herein are methods for generating an immune response in a subject, the methods comprising: administering a therapeutically effective amount of a pharmaceutical composition provided herein to the subject.

Further provided herein are methods of treating or preventing a disease in a subject, the methods comprising: administering a therapeutically effective amount of the pharmaceutical composition to the subject.

Further provided herein are methods of imaging and/or tracking delivery of one or more nucleic acids in a subject, the methods comprising: administering a therapeutically effective amount of the pharmaceutical composition to the subject.

Further provided herein are methods for preparing a lyophilized compositions, the methods comprising: (a) obtaining a lipid carrier, wherein the lipid carrier is a nanoemulsion comprising a hydrophobic core, optionally one or more inorganic nanoparticles and one or more lipids; (b) incorporating one or more nucleic acid into the lipid carrier to form a lipid carrier-nucleic acid complex; (c) adding at least one cryoprotectant to the lipid carrier-nucleic acid complex to form a formulation; and (d) lyophilizing the formulation to form a lyophilized composition.

Further provided herein are methods for preparing a spray-dried composition, the methods comprising: (a) obtaining a lipid carrier, wherein the lipid carrier is a nanoemulsion comprising a hydrophobic core, optionally one or more inorganic nanoparticles and one or more lipids; (b) incorporating one or more nucleic acid into the lipid carrier to form a lipid carrier-nucleic acid complex; (c) adding at least one cryoprotectant to the lipid carrier-nucleic acid complex to form a formulation; and (d) spray drying the formulation to form a spray-dried composition.

Further provided herein are methods for reconstituting a lyophilized composition, the methods comprising: (a) obtaining a lipid carrier, wherein the lipid carrier is a nanoemulsion comprising a hydrophobic core, optionally one or more inorganic nanoparticles, and one or more lipids; (b) incorporating one or more nucleic acid into the said lipid carrier to form a lipid carrier-nucleic acid complex; (c) adding at least one cryoprotectant to the lipid carrier-nucleic acid complex to form a formulation; lyophilizing the formulation to form a lyophilized composition; and (d) reconstituting the lyophilized composition in a suitable diluent.

Further provided herein are methods for reconstituting a spray-dried composition, the methods comprising: (a) obtaining a lipid carrier, wherein the lipid carrier is a nanoemulsion comprising a hydrophobic core, optionally one or more inorganic nanoparticles, and one or more lipids; (b) incorporating one or more nucleic acid into the said lipid carrier to form a lipid carrier-nucleic acid complex; (c) adding at least one cryoprotectant to the lipid carrier-nucleic acid complex to form a formulation; (d) spray drying the formulation to form a spray-dried composition; and (e) reconstituting the spray-dried composition in a suitable diluent.

Further provided herein are dried compositions, wherein the dried compositions comprise: a sorbitan fatty acid ester, an ethoxylated sorbitan ester, a cationic lipid, an immune stimulant, and an RNA.

Further provided herein are dried compositions, wherein the dried compositions comprise: sorbitan monostearate, polyoxyethylene (20) sorbitan monooleate, DOTAP, an immune stimulant, and a RNA.

Further provided here are dried compositions, wherein the dried compositions comprise: (a) a lipid carrier, wherein the lipid carrier is a nanoemulsion comprising a hydrophobic core and one or more lipids; (b) optionally one or more nucleic acid; and (c) at least one sugar present in amount of (i) at least about 50% by weight of the dried composition, or (ii) present in an amount of least 50 mg.

Further provided herein are pharmaceutical compositions, wherein the pharmaceutical compositions comprise: a dried composition provided herein reconstituted in a suitable diluent; and a pharmaceutically acceptable carrier.

Further provided herein are kits, wherein the kits comprise: a pharmaceutical composition provided herein and a delivery system for administration to a subject.

Further provided herein are methods for generating an immune response in a subject, wherein the methods comprise: administering to the subject a therapeutically effective amount of the pharmaceutical composition provided herein.

Further provided herein are methods of treating or preventing a disease in a subject, wherein the methods comprise: administering to the subject a therapeutically effective amount of the pharmaceutical composition provided herein.

Further provided herein are methods of imaging and/or tracking delivery of one or more nucleic acids in a subject, wherein the methods comprise: administering a therapeutically effective amount of the pharmaceutical composition described herein.

BRIEF DESCRIPTION OF THE DRAWINGS

FIG. 1A shows an oil-in-water emulsion. FIG. 1B shows a nanostructured lipid carrier (NLC).

FIG. 1C shows a nanoparticle having an inorganic nanoparticle in liquid oil.

FIG. 2 illustrates the appearance of cake for the nanostructured lipid carrier (NLC) and lipid carrier formulations in the indicated sugar compositions at time=0 hours after lyophilization cycle #1.

FIG. 3 illustrates the appearance of cake for the nanostructured lipid carrier (NLC) and lipid carrier formulations in the indicated sugar compositions after 24 hours at 25 degrees Celsius and 42 degrees Celsius after lyophilization cycle #1.

FIG. 4 illustrates the appearance of nanostructured lipid carrier (NLC) and lipid carrier formulations in the indicated sugar compositions at 24 hours at 25 degrees Celsius and 42 degrees Celsius after lyophilization cycle #1.

FIG. 5A shows the fold-change relative to liquid formulation at time=0 hours in the indicated sugar compositions. FIG. 5B shows the points change relative to liquid formulation at time=0 hours in PDI in the indicated sugar compositions.

FIG. 6A shows the RNA integrity by agarose gel electrophoresis in the indicated sugar composition after lyophilization cycle #1 for lipid carrier+RNA formulations.

FIG. 6B shows the RNA integrity by agarose gel electrophoresis in the indicated sugar composition after lyophilization cycle #1 for lipid carrier+RNA and NLC+RNA formulations.

FIG. 7A shows the Relative Luminescence Units (RLU) for the lipid carrier+repRNA-SEAP in 10% trehalose. FIG. 7B shows the Relative Luminescence Units (RLU) for the lipid carrier+repRNA-SEAP in 5% mannitol. FIG. 7C shows the Relative Luminescence Units (RLU) for the lipid carrier+repRNA-SEAP in 10% sucrose. FIG. 7D shows the Relative Luminescence Units (RLU) for the lipid carrier+repRNA-SEAP in 20% sucrose. FIG. 7E shows the Relative Luminescence Units (RLU) for the lipid carrier+repRNA-SEAP in 5% glucose. FIG. 7F shows the Relative Luminescence Units (RLU) for the lipid carrier+repRNA-SEAP in 10% maltose. FIG. 7G shows the Relative Luminescence Units (RLU) for the NLC+repRNA-SEAP in 10% sucrose.

Figure 9:
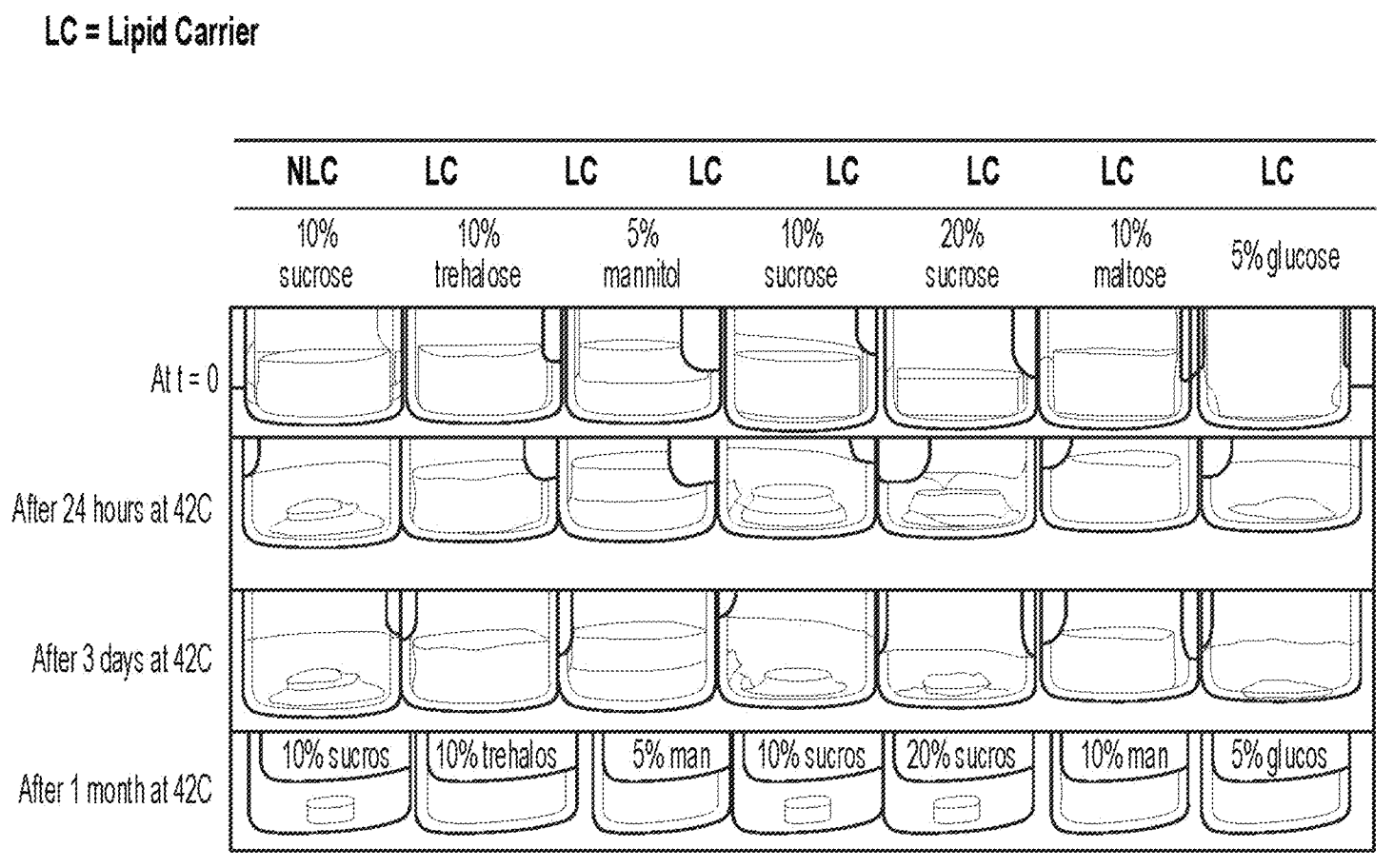

FIG. 9 illustrates the appearance of lipid carrier+RNA-SEAP cakes at various time points (time=0 hours, after 24 hours at 42 degrees Celsius and after 3 days at 42 degrees Celsius and after 1 month at 42 degrees Celsius) in the indicated sugar composition after lyophilization cycle #1.

FIG. 10A shows the points change in PDI of reconstituted formulations in the indicated sugar composition. FIG. 10B shows the $\log_{10}$ fold-change in particle size relative to lipid carrier+RNA fresh complex.

FIG. 13A shows the absorption spectra of various formulations with Nano Luciferase encoding replicon RNA in the first experiment. FIG. 13B shows the absorption spectra of various formulations with Nano Luciferase encoding replicon RNA in the second experiment.

FIG. 14A shows the production of TNF-alpha for various formulations in the first experiment. FIG. 14B shows the production of TNF-alpha for various formulations in the second experiment.

FIG. 15A show the correlation between sec-NanoLuc and TNF-alpha for various formulations in the first experiment. FIG. 15B show the correlation between sec-NanoLuc and TNF-alpha for various formulations in the second experiment.

FIG. 16A show the Relative Luminescence Units (RLU) at Day 4. FIG. 16B show the Relative Luminescence Units (RLU) at Day 6. FIG. 16C show the Relative Luminescence Units (RLU) at Day 8. FIG. 16D is a copy of the Relative Luminescence Units (RLU) at Day 4. FIG. 16E is a copy of Relative Luminescence Units (RLU) at Day 6. FIG. 16F is a copy of the Relative Luminescence Units (RLU) at Day 8.

FIG. 18A shows a dot chart with IgG (μg/ml) on the Y-axis, group number on the X-axis for conditions 1 to 14. Measurements were recorded at day 14 for anti-D614G (1:40 dilution) IgG responses. FIG. 18B shows a dot chart with IgG (μg/ml) on the Y-axis, group number on the X-axis for conditions 1 to 14. Measurements were recorded at day 28 for anti-D614G (1:200 dilution) IgG responses.

Figure 1A:
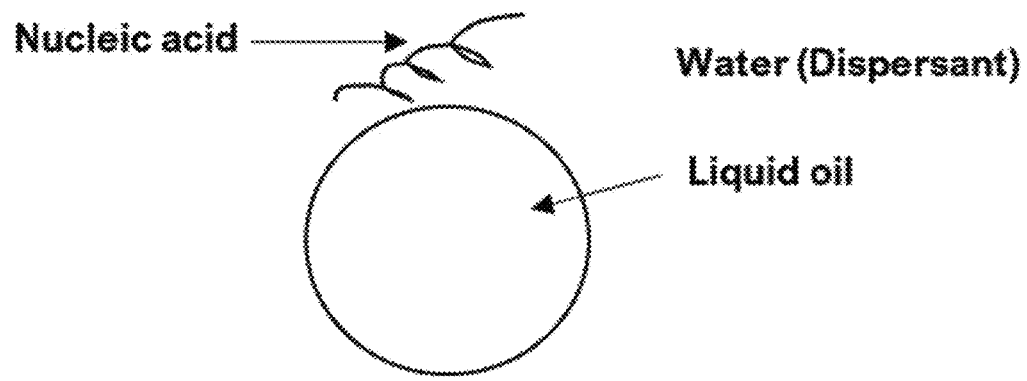
FIGS. 1A-1C show schematic representations of nanoparticle (NP) carriers.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

DETAILED DESCRIPTION

Provided herein are methods for the generation of therapeutically relevant compositions having enhanced stability profiles. In some embodiments, the compositions comprise a lipid nanoparticle carrier optionally complexed with a nucleic acid. In further embodiments, the composition is freeze dried.

Definitions

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document. All references disclosed herein, including patent references and non-patent references, are hereby incorporated by reference in their entirety as if each was incorporated individually. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The compositions of the present disclosure can comprise, consist essentially of, or consist of, the components disclosed.

As used herein, "optional" or "optionally" means that the subsequently described circumstance may or may not occur, so that the description includes instances where the circumstance occurs and instances where it does not.

As used herein, the term "about" or "approximately" means a range of up to +20%, of a given value. Where particular values are described in the application and claims, unless otherwise stated, the term "about" is implicit and in this context means within an acceptable error range for the particular value.

As used herein, the term "N/P ratio (or N:P)" refers to the ratio of positively-chargeable polymer amine (N=nitrogen) groups to negatively-charged nucleic acid phosphate (P) groups. The N/P character of a polymer/nucleic acid complex can influence many other properties such as its net surface charge, size, and stability.

As used herein, "modified nucleotide" refers to a nucleotide that contains one or more chemical modifications (e.g., substitutions) in or on the nitrogenous base of the nucleoside (e.g., cytosine (C), thymine (T) or uracil (U), adenine (A) or guanine (G)).

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure. For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

Nanoparticle Carrier Systems

Provided herein are various compositions comprising a nanoparticle or a plurality of nanoparticles. Nanoparticles also referred to herein as carriers or abbreviated as NPs. Nanoparticles provided herein may be an organic, inorganic, or a combination of inorganic and organic materials that are less than about 1 micrometer (μm) in diameter. In some embodiments, nanoparticles provided herein are used as a delivery system for a bioactive agent provided herein.

In some embodiments, provided is a dried composition comprising a lipid carrier, wherein the lipid carrier is a nanoemulsion comprising a hydrophobic core, one or more inorganic nanoparticles and one or more lipids; one or more nucleic acid; and at least one cryoprotectant. The composition can be spray-dried or lyophilized using techniques known in the art. The composition is thermally stable. For example, the composition is thermally stable at about 25 degrees Celsius, about 45 degrees Celsius, about −20 degrees Celsius, and at about 2 degrees Celsius to about 8 degrees Celsius. The composition is thermally stable for at least 1 week, at least 2 weeks, and/or at least 1 month.

Provided here are methods for freeze drying compositions described herein. In some embodiments, sublimation, or primary drying, takes place at this point, to remove the unbound water; secondary drying is then performed, to sublime the bound water, taking the material down to a desired residual moisture level. Given that the water at this stage is bound to the target rather than unbound, more energy is typically required to drive this process. Spray drying may be used, it is often a faster process and involves conversion of a liquid formulation into a dry powder in a single step. The solution is atomized into fine droplets, which are quickly dried straight in large chamber using a warm gas. The resulting dry particles may be then collected with a cyclone. Additional drying techniques include, for example, spray freeze drying and supercritical fluid drying.

The disclosure provides use of a lipid carrier as carriers of one or more nucleic acids, such as RNA. In particular, a solid inorganic core in a lipid matrix with a charged coating in a buffer is disclosed. The use of these nanoparticles has numerous advantages: RNA can be complexed independent of the particles, and the particle can be designed to have magnetic signals, such as useable for MRI or other imaging techniques. RNA is protected by the particles and they drive expression of numerous types of protein including antigens off of the protected RNA when given to cells or a living being.

Figure 1B:
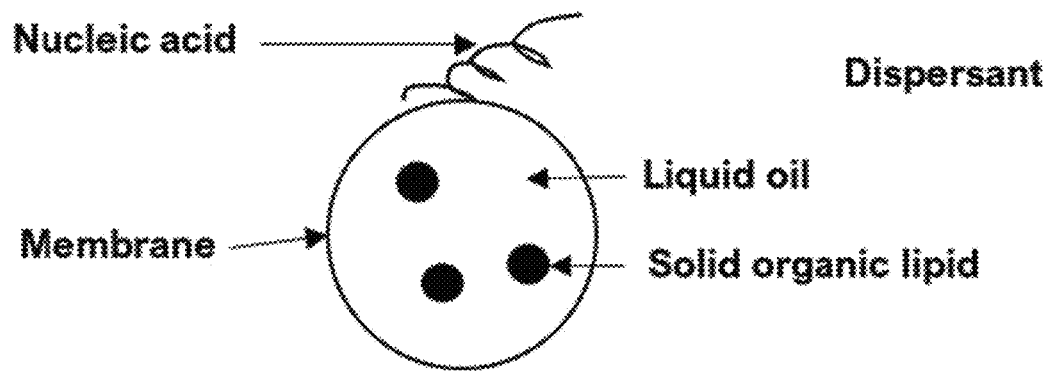
Figure 1C:
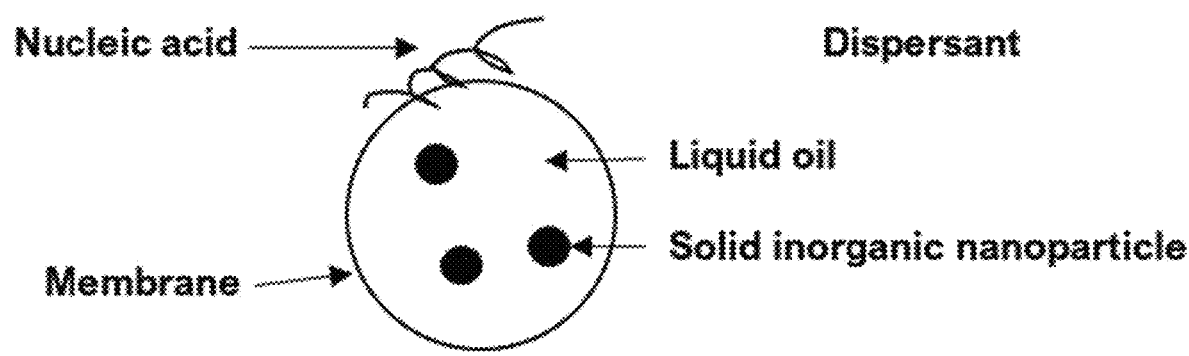

Various nanoparticles and formulations of nanoparticles (i.e., nanoemulsions) are employed. Exemplary nanoparticles are illustrated in FIGS. 1A-1C. Nanoparticles provided herein can include but are not limited to: oil in water emulsions, nanostructured lipid carriers (NLCs), cationic nanoemulsions (CNEs), vesicular phospholipid gels (VPG), polymeric nanoparticles, cationic lipid nanoparticles, liposomes, gold nanoparticles, solid lipid nanoparticles (LNPs or SLNs), mixed phase core NLCs, ionizable lipid carriers, magnetic carriers, polyethylene glycol (PEG)-functionalized carriers, cholesterol-functionalized carriers, polylactic acid (PLA)-functionalized carriers, and polylactic-co-glycolic acid (PLGA)-functionalized lipid carriers.

Oil in water emulsions, as illustrated in FIG. 1A (not to scale), are stable, immiscible fluids containing an oil droplet dispersed in water or aqueous phase. FIG. 1B (not to scale) illustrates a nanostructured lipid carrier (NLCs) which can comprise a blend of solid organic lipids (e.g., trimyristin) and liquid oil (e.g., squalene). In NLCs, the solid lipid is dispersed in the liquid oil. The entire nanodroplet is dispersed in the aqueous (water) phase. In some embodiments, the nanoparticle comprises inorganic nanoparticles, as illustrated in FIG. 1C (not to scale), as solid inorganic nanoparticles (e.g., iron oxide nanoparticles) dispersed in liquid oil. The entire nanodroplet is then dispersed as a colloid in the aqueous (water) phase. In some embodiments, the nanoparticles provided herein are dispersed in an aqueous solution. Non-limiting examples of aqueous solutions include water (e.g., sterilized, distilled, deionized, ultra-pure, RNAse-free, etc.), saline solutions (e.g., Kreb's, *Ascaris*, Dent's, Tet's saline), or 1% (w/v) dimethyl sulfoxide (DMSO) in water.

Provided herein are various compositions and methods comprising a lipid carrier. The lipid carrier is a nanoemulsion that comprises a hydrophobic core, one or more inorganic nanoparticles and one or more lipids. The hydrophobic core of the lipid carrier comprises an oil. In some embodiments, the oil is in liquid phase.

In some embodiments, the nanoparticles provided herein comprise a hydrophilic surface. In some embodiments, the hydrophilic surface comprises a cationic lipid. In some embodiments, the hydrophilic surface comprises an ionizable lipid. In some embodiments, the nanoparticle comprises a membrane. In some embodiments, the membrane comprises a cationic lipid. In some embodiments, the nanoparticles provided herein comprise a cationic lipid. Exemplary cationic lipids for inclusion in the hydrophilic surface include, without limitation: 1,2-dioleoyloxy-3 (trimethylammonium)propane (DOTAP), 3β-[N-(N',N'-dimethylaminoethane) carbamoyl]cholesterol (DC Cholesterol), dimethyldioctadecylammonium (DDA); 1,2-dimyristoyl 3-trimethylammoniumpropane (DMTAP),dipalmitoyl(C16:0)trimethyl ammonium propane (DPTAP), distearoyltrimethylammonium propane (DSTAP), N-[1-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3'',3'''-(((methylazanediyl) bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; β-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 3β-[N-(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9'',9''',9'''',9'''''-((((benzene-1,3,5-tricarbonyl)yris(azanediyl)) tris (propane-3,1-diyl)) tris(azantriyl))hexanonanoate; Lipid H (SM-102), heptadecan-9-yl 8-((2-hydroxyethyl)(6-oxo-6-(undecyloxy)hexyl)amino) octanoate; OF-Deg-Lin, (((3,6-dioxopiperazine-2,5-diyl)bis (butane-4,1-diyl))bis(azanetriyl))tetrakis(ethane-2,1-diyl) (9Z,9'Z,9''Z,9'''Z,12Z,12'Z,12''Z,12'''Z)-tetrakis (octadeca-9,12-dienoate); PEG2000-DMG, (R)-2,3-bis(myristoyloxy) propyl-1-(methoxy poly(ethylene glycol)2000) carbamate; TT3, or N1,N3,N5-tris(3-(didodecylamino)propyl)benzene- 1,3,5-tricarboxamide. Other examples for suitable classes of lipids include, but are not limited to, the phosphatidylcholines (PCs), phosphatidylethanolamines (PEs), phosphatidylglycerol (PGs); and PEGylated lipids including PEGylated version of any of the above lipids (e.g., DSPE-PEGs). In some embodiments, the nanoparticle provided herein comprises DOTAP.

In some embodiments, the nanoparticle provided herein comprises an oil. In some embodiments, the oil is in liquid phase. Non-limiting examples of oils that can be used include α-tocopherol, coconut oil, grapeseed oil, lauroyl polyoxylglyceride, mineral oil, monoacylglycerol, palm kernel oil, olive oil, paraffin oil, peanut oil, propolis, squalene, squalane, solanesol, soy lecithin, soybean oil, sunflower oil, a triglyceride, or vitamin E. In some embodiments, the nanoparticle provided herein comprises a triglyceride. Exemplary triglycerides include but are not limited to: capric triglycerides, caprylic triglycerides, a caprylic and capric triglycerides, triglyceride esters, and myristic acid triglycerins.

In some embodiments, the nanoparticles provided herein comprise a liquid organic material and a solid inorganic material. In some embodiments, the nanoparticle provided herein comprises an inorganic particle. In some embodiments, the inorganic particle is a solid inorganic particle. In some embodiments, the nanoparticle provided herein comprises the inorganic particle within the hydrophobic core. In some embodiments, the oil is in solid phase. In some embodiments, the oil comprises solanesol.

In some embodiments, the nanoparticle provided herein comprises a metal. In some embodiments, the nanoparticle provided herein comprises a metal within the hydrophobic core. The metal can be without limitation, a metal salt, a metal oxide, a metal hydroxide, or a metal phosphate. In some embodiments, the nanoparticle provided herein comprises aluminum oxide ($Al_2O_3$), aluminum oxyhydroxide, iron oxide ($Fe_3O_4$, $Fe_2O_3$, FeO, or combinations thereof), titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. The inorganic particles may be formed from one or more same or different metals (any metals including transition metal). In some embodiments, the inorganic particle is a transition metal oxide. In some embodiments, the transition metal is magnetite ($Fe_3O_4$), maghemite (γ-$Fe_2O_3$), wustite (FeO), or hematite (alpha (α)-$Fe_2O_3$). In some embodiments, the metal is aluminum hydroxide or aluminum oxyhydroxide, and a phosphate-terminated lipid or a surfactant, such as oleic acid, oleylamine, SDS, TOPO or DSPA is used to coat the inorganic solid nanoparticle before it is mixed with the liquid oil to form the hydrophobic core.

In some embodiments, the metal can comprise a paramagnetic, a superparamagnetic, a ferrimagnetic or a ferromagnetic compound. In some embodiments, the metal is a superparamagnetic iron oxide ($Fe_3O_4$).

In some embodiments, the nanoparticle provided herein comprises a cationic lipid, an oil, and an inorganic particle. In some embodiments, the nanoparticle provided herein comprises DOTAP; squalene and/or glyceryl trimyristate-dynasan; and iron oxide. In some embodiments, the nanoparticle provided herein further comprises a surfactant. Thus, in some embodiments, the nanoparticles provided herein comprise a cationic lipid, an oil, an inorganic particle, and a surfactant.

Surfactants are compounds that lower the surface tension between two liquids or between a liquid and a solid component of the nanoparticles provided herein. Surfactants can be hydrophobic, hydrophilic, or amphiphilic. In some embodiments, the nanoparticle provided herein comprises a hydrophobic surfactant. Exemplary hydrophobic surfactants that can be employed include but are not limited to: sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85). Suitable hydrophobic surfactants include those having a hydrophilic-lipophilic balance (HLB) value of 10 or less, for instance, 5 or less, from 1 to 5, or from 4 to 5. For instance, the hydrophobic surfactant can be a sorbitan ester having an HLB value from 1 to 5, or from 4 to 5. In some embodiments, the nanoparticle provided herein comprises a hydrophilic surfactant, also called an emulsifier.

In some embodiments, the nanoparticle provided herein comprises polysorbate. Polysorbates are oily liquids derived from ethoxylated sorbitan (a derivative of sorbitol) esterified with fatty acids. In some embodiments, the nanoparticle or lipid carrier provided herein comprises a hydrophilic surfactant. Exemplary hydrophilic surfactants that can be employed include but are not limited to: polysorbates such as TWEEN®, Kolliphor, Scattics, Alkest, or Canarcel; polyoxyethylene sorbitan ester (polysorbate); polysorbate 80 (polyoxyethylene sorbitan monooleate, or TWEEN® 80); polysorbate 60 (polyoxyethylene sorbitan monostearate, or TWEEN® 60); polysorbate 40 (polyoxyethylene sorbitan monopalmitate, or TWEEN® 40); and polysorbate 20 (polyoxyethylene sorbitan monolaurate, or TWEEN® 20). In one embodiment, the hydrophilic surfactant is polysorbate 80.

Nanoparticles provided herein comprises a hydrophobic core surrounded by a lipid membrane (e.g., a cationic lipid such as DOTAP). In some embodiments, the hydrophobic core comprises: one or more inorganic particles; a phosphate-terminated lipid; and a surfactant.

Inorganic solid nanoparticles described herein may be surface modified before mixing with the liquid oil. For instance, if the surface of the inorganic solid nanoparticle is hydrophilic, the inorganic solid nanoparticle may be coated with hydrophobic molecules (or surfactants) to facilitate the miscibility of the inorganic solid nanoparticle with the liquid oil in the "oil" phase of the nanoemulsion particle. In some embodiments, the inorganic particle is coated with a capping ligand, the phosphate-terminated lipid, and/or the surfactant. In some embodiments the hydrophobic core comprises a phosphate-terminated lipid. Exemplary phosphate-terminated lipids that can be employed include but are not limited to: trioctylphosphine oxide (TOPO) or distearyl phosphatidic acid (DSPA). In some embodiments, the hydrophobic core comprises surfactant is a phosphorous-terminated surfactant, a carboxylate-terminated surfactant, a sulfate-terminated surfactant, or an amine-terminated surfactant. Typical carboxylate-terminated surfactants include oleic acid. Typical amine terminated surfactants include oleylamine. In some embodiments, the surfactant is distearyl phosphatidic acid (DSPA), oleic acid, oleylamine or sodium dodecyl sulfate (SDS). In some embodiments, the inorganic solid nanoparticle is a metal oxide such as an iron oxide, and a surfactant, such as oleic acid, oleylamine, SDS, DSPA, or TOPO, is used to coat the inorganic solid nanoparticle before it is mixed with the liquid oil to form the hydrophobic core.

In some embodiments, the hydrophobic core comprises: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate.

In some embodiments, the hydrophobic core comprises: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; ahydrophobic surfactant comprising sorbitan monostearate; and a hydrophilic surfactant comprising polysorbate 80.

In some embodiments, the hydrophobic core consists of one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate. In some embodiments, the hydrophobic core consists of one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80. In some embodiments, the nanoparticle provided herein can comprise from about 0.2% to about 40% w/v squalene, from about 0.001% to about 10% w/v iron oxide nanoparticles, from about 0.2% to about 10% w/v DOTAP, from about 0.25% to about 5% w/v sorbitan monostearate, and from about 0.5% to about 10% w/v polysorbate 80. In some embodiments the nanoparticle provided herein from about 2% to about 6% w/v squalene, from about 0.01% to about 1% w/v iron oxide nanoparticles, from about 0.2% to about 1% w/v DOTAP, from about 0.25% to about 1% w/v sorbitan monostearate, and from about 0.5%) to about 5% w/v polysorbate 80. In some embodiments, the nanoparticle provided herein can comprise from about 0.2% to about 40% w/v squalene, from about 0.001% to about 10% w/v aluminum hydroxide or aluminum oxyhydroxide nanoparticles, from about 0.2% to about 10% w/v DOTAP, from about 0.25% to about 5% w/v sorbitan monostearate, and from about 0.5% to about 10% w/v polysorbate 80. In some embodiments, the nanoparticle provided herein can comprise from about 2% to about 6% w/v squalene, from about 0.01% to about 1% w/v aluminum hydroxide or aluminum oxyhydroxide nanoparticles, from about 0.2% to about 1% w/v DOTAP, from about 0.25% to about 1% w/v sorbitan monostearate, and from about 0.5%) to about 5% w/v polysorbate 80.

In some embodiments, a composition described herein comprises at least one nanoparticle formulation as described in Table 1. In some embodiments, a composition described herein comprises any one of NP-1 to NP-30. In some embodiments, a composition described herein comprises any one of NP-1 to NP-31. In some embodiments, the nanoparticles provided herein are admixed with a nucleic acid provided herein. In some embodiments, nanoparticles provided herein are made by homogenization and ultrasonication techniques.

TABLE 1

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| NP-1 [Fe-LC] (LC = lipid carrier) | 30 mg/ml 1,2-dioleoyl-3-trimethylammonium-propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN ® 80) | 0.2 mg Fe/ml 12 nm oleic acid-coated iron oxide nanoparticles 10 mM sodium citrate dihydrate. |
| NP-2 [High Fe-LC] | 30 mg/ml 1,2-dioleoyl-3-trimethylammonium-propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene | 1 mg Fe/ml 15 nm oleic acid-coated iron oxide nanoparticles 10 mM sodium citrate dihydrate. |

TABLE 1-continued

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
|  |  |  | (20) sorbitan monooleate, $C_{64}H_{124}O_{26}$, Polysorbate 80 (TWEEN ® 80) |  |
| NP-3 [Fe-LC-Miglyol] | 30 mg/ml 1,2-dioleoyl-3-trimethylammonium-propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN ® 80) | 0.2 mg Fe/ml 15 nm oleic acid-coated iron oxide nanoparticles 10 mM sodium citrate dihydrate. |
| NP-4 [High Fe-LC-Miglyol] | 30 mg/ml 1,2-dioleoyl-3-trimethylammonium-propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN ® 60) 37 mg/ml polyoxyethylene (20) sorbitan monooleate, $C_{64}H_{124}O_{26}$, Polysorbate 80 (TWEEN ® 80) | 1 mg Fe/ml 15 nm oleic acid-coated iron oxide nanoparticles 10 mM sodium citrate dihydrate. |
| NP-5 [Alum-LC] | 30 mg/ml DOTAP chloride | 37.5 mg/ml squalene | 37 mg/ml sorbitan monostearate (SPAN ® 60) 37 mg/ml polysorbate 80 (TWEEN ® 80) | 1 mg/ml trioctylphosphine oxide (TOPO)-coated aluminum hydroxide (Alhydrogel ® 2%) particles 10 mM sodium citrate dihydrate. |
| NP-6 [Fe-LC-Solanesol] | 30 mg/ml DOTAP chloride | 37.5 mg/ml Solanesol (Cayman chemicals), | 37 mg/ml sorbitan monostearate (SPAN ® 60) 37 mg/ml polysorbate 80 (TWEEN ® 80) | 0.2 mg Fe/ml oleic acid-coated iron oxide nanoparticles 10 mM sodium citrate |
| NP-7 [NLC] | 30 mg/ml DOTAP chloride | 37.5 mg/ml squalene 2.4 mg/ml Dynasan 114 | 37 mg/ml sorbitan monostearate (SPAN ® 60) 37 mg/ml polysorbate 80 (TWEEN ® 80) | 10 mM sodium citrate |
| NP-8 [CNE] | 4 mg/ml DOTAP chloride | 43 mg/ml squalene | 5 mg/ml sorbitan trioleate (SPAN ® 85) 5 mg/ml polysorbate 80 (TWEEN ® 80) | 10 mM sodium citrate |
| NP-9 | 7.5 mg/ml 1,2-dioleoyl-3-trimethylammonium-propane (DOTAP) chloride | 9.4 mg/ml squalene ((6E,10E,14E,18E)-2,6,10,15,19,23-Hexamethyltetracosa-2,6,10,14,18,22-hexaene, $C_{30}H_{50}$) 0.63 mg/ml glyceryl trimyristate-dynasan (DYNASAN 114 ®) | 9.3 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) | 0.05 mg/ml 15 nanometer superparamagnetic iron oxide ($Fe_3O_4$) 10 mM sodium citrate dihydrate |

TABLE 1-continued

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| | | | (SPAN® 60) 9.3 mg/ml polyoxyethylene (20) sorbitan monooleate, $C_{64}H_{124}O_{26}$, Polysorbate 80 (TWEEN 80®) | |
| NP-10 | 0.4% DOTAP | 0.25% glyceryl trimyristate-dynasan (DYNASAN 114®) 4.75% Squalene | 0.5% sorbitan monostearate (SPAN® 60) 0.5% polysorbate 80 (TWEEN® 80) | |
| NP-11 | 3.0% DOTAP | 0.25% glyceryl trimyristate-dynasan (DYNASAN 114®) 3.75% Squalene | 3.7% sorbitan monostearate (SPAN® 60) 3.7% polysorbate 80 (TWEEN® 80) | |
| NP-12 | 0.4% DOTAP | 4.3% Squalene | 0.5% sorbitan trioleate (SPAN® 85) 0.5% polysorbate 80 (TWEEN® 80) | |
| NP-13 | 0.4% DOTAP | 0.25% glyceryl trimyristate-dynasan (DYNASAN 114®) 4.08% squalene | 2.0% polysorbate 80 (TWEEN® 80) | |
| NP-14 | 0.4% DOTAP | 0.25% glyceryl trimyristate-dynasan (DYNASAN 114®) 4.08% squalene | 0.5% sorbitan trioleate (SPAN® 85) 2.0% polysorbate 80 (TWEEN® 80) | |
| NP-15 | 0.4% DOTAP | 0.25% glyceryl trimyristate-dynasan (DYNASAN 114®) 4.08% squalene | 0.25% sorbitan trioleate (SPAN® 85) 2.0% polysorbate 80 (TWEEN® 80) | |
| NP-16 | 0.4% DOTAP | 5% squalene | 0.5% sorbitan trioleate (SPAN® 85) 2.0% polysorbate 80 (TWEEN® 80) | |
| NP-17 | 0.4% DOTAP | 5% squalene | 0.5% sorbitan monostearate (SPAN® 60) 2% polysorbate 80 (TWEEN® 80) | |
| NP-18 | 0.4% DOTAP | 0.25% glyceryl trimyristate-dynasan (DYNASAN 114®) 4.08% squalene | 2% sorbitan trioleate (SPAN® 85) 2% polysorbate 80 (TWEEN® 80) | |
| NP-19 | 0.4% DOTAP | 0.25% glyceryl trimyristate-dynasan (DYNASAN 114®) 4.75% Squalene | 0.5% sorbitan monostearate (SPAN® 60) 0.5% polysorbate 80 (TWEEN® 80) | 1% aluminum hydroxide |
| NP-20 | 3.0% DOTAP | 0.25% glyceryl trimyristate-dynasan (DYNASAN 114®) 3.75% Squalene | 3.7% sorbitan monostearate (SPAN® 60) 3.7% polysorbate 80 (TWEEN® 80) | 1% aluminum hydroxide |
| NP-21 | 0.4% DOTAP | 4.3% Squalene | 0.5% sorbitan trioleate (SPAN® 85) 0.5% polysorbate 80 (TWEEN® 80) | 1% aluminum hydroxide |
| NP-22 | 0.4% DOTAP | 0.25% glyceryl trimyristate-dynasan (DYNASAN 114®) 4.08% squalene | 2.0% polysorbate 80 (TWEEN® 80) | 1% aluminum hydroxide |

TABLE 1-continued

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| NP-23 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80) | 1% aluminum hydroxide |
| NP-24 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80) | 1% aluminum hydroxide |
| NP-25 | 0.4% DOTAP | 5% squalene | 0.5% sorbitan trioleate (SPAN ® 85) 2.0% polysorbate 80 (TWEEN ® 80) | 1% aluminum hydroxide |
| NP-26 | 0.4% DOTAP | 5% squalene | 0.5% sorbitan monostearate (SPAN ® 60) 2% polysorbate 80 (TWEEN ® 80) | 1% aluminum hydroxide |
| NP-27 | 0.4% DOTAP | 0.25% glyceryl trimyristate-dynasan (DYNASAN 114 ®) 4.08% squalene | 2% sorbitan trioleate (SPAN ® 85) 2% polysorbate 80 (TWEEN ® 80) | 1% aluminum hydroxide |
| NP-28 | 0.5-5.0 mg/ml DOTAP | 0.2-10% (v/v) squalene | 0.01-2.5% (v/v) polysorbate 80 (TWEEN ® 80) | |
| NP-29 | 0.4% (w/w) DOTAP | 4.3% (w/w) squalene | 0.5% (w/w) sorbitan trioleate (SPAN ® 85) 0.5% (w/w) polysorbate 80 (TWEEN ® 80) | |
| NP-30 [LC without inorganic core] | 30 mg/ml DOTAP chloride | 37.5 mg/ml squalene | 37 mg/ml sorbitan monostearate (SPAN ® 60) 37 mg/ml polysorbate 80 (TWEEN ® 80) | 10 mM sodium citrate |
| NP-31 | 30 mg/ml DOTAP chloride | 37.5 mg/ml squalene | 37 mg/ml sorbitan monostearate (SPAN ® 60) 37 mg/ml polysorbate 80 (TWEEN ® 80) | 0.4 mg Fe/ml 5 nm oleic acid-coated iron oxide nanoparticles 10 mM sodium citrate dihydrate. |

In some embodiments, nanoparticles provided herein comprise: sorbitan monostearate (e.g., SPAN® 60), polysorbate 80 (e.g., TWEEN® 80), DOTAP, squalene, and no solid particles. In some embodiments, nanoparticles provided herein comprise: sorbitan monostearate (e.g., SPAN® 60), polysorbate 80 (e.g., TWEEN® 80), DOTAP, squalene, and iron oxide particles. In some embodiments, nanoparticles provided herein comprise an immune stimulant. In some embodiments, the immune stimulant is squalene. In some embodiments, the immune stimulant is a medium chain triglyceride. In some embodiments, the immune stimulant is Miglyol 810 or Miglyol 812. Miglyol 810 is a triglyceride ester of saturated caprylic and capric fatty acids and glycerol. Miglyol 812 is a triglyceride ester of saturated coconut/palmkemel oil derived caprylic and capric fat acids and plant derived glycerol. In some embodiments, the immune stimulant can decrease the total amount of protein produced, but can increase the immune response to a composition provided herein (e.g., when delivered as a vaccine). In some embodiments, the immune stimulant can increase the total amount of protein produced, but can decrease the immune response to a composition provided herein.

Nanoparticles provided herein can be of various average diameters in size. In some embodiments, nanoparticles provided herein have an average diameter (z-average hydrodynamic diameter, measured by dynamic light scattering) ranging from about 20 nanometers (nm) to about 200 nm. In some embodiments, the z-average diameter of the nanoparticle ranges from about 20 nm to about 150 nm, from about 20 nm to about 100 nm, from about 20 nm to about 80 nm, from about 20 nm to about 60 nm. In some embodiments, the z-average diameter of the nanoparticle) ranges from about 40 nm to about 200 nm, from about 40 nm to about 150 nm, from about 40 nm to about 100 nm, from about 40 nm to about 90 nm, from about 40 nm to about 80 nm, or from about 40 nm to about 60 nm. In one embodiment, the z-average diameter of the nanoparticle is from about 40 nm to about 80 nm. In some embodiments, the z-average diameter of the nanoparticle is from about 40 nm to about 60 nm. In some embodiments, the nanoparticle is up to 100 nm in diameter. In some embodiments, the nanoparticle is 50 to 70 nm in diameter. In some embodiments, the nanoparticle is 40 to 80 nm in diameter. In some embodiments, the inorganic particle (e.g., iron oxide) within the hydrophobic core of the nanoparticle can be an average diameter (number weighted average diameter) ranging from about 3 nm to about 50 nm. For instance, the inorganic particle can have an average diameter of about 5 nm, about 10 nm, about 15 nm, about 20 nm, about 25 nm, about 30 nm, about 35 nm, about 40 nm, about 45 nm, or about 50 nm.

Nanoparticles provided herein may be characterized by the polydispersity index (PDI), which is an indication of their quality with respect to size distribution. In some embodiments, average polydispersity index (PDI) of the nanoparticles provided herein ranges from about 0.1 to about 0.5. In some embodiments, the average PDI of the nanoparticles can range from about 0.2 to about 0.5, from about 0.1 to about 0.4, from about 0.2 to about 0.4, from about 0.2 to about 0.3, or from about 0.1 to about 0.3.

In some embodiments, the nanoparticles provided herein comprise an oil-to-surfactant molar ratio ranging from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the nanoparticles provided herein comprise a hydrophilic surfactant-to-lipid ratio ranging from about 0.1:1 to about 2:1, from about 0.2:1 to about 1.5:1, from about 0.3:1 to about 1:1, from about 0.5:1 to about 1:1, or from about 0.6:1 to about 1:1. In some embodiments, the nanoparticles provided herein comprise a hydrophobic surfactant-to-lipid ratio ranging from about 0.1:1 to about 5:1, from about 0.2:1 to about 3:1, from about 0.3:1 to about 2:1, from about 0.5:1 to about 2:1, or from about 1:1 to about 2:1. In some embodiments, the nanoparticles provided herein comprise from about 0.2% to about 40% w/v liquid oil, from about 0.001% to about 10% w/v inorganic solid nanoparticle, from about 0.2% to about 10% w/v lipid, from about 0.25% to about 5% w/v hydrophobic surfactant, and from about 0.5% to about 10% w/v hydrophilic surfactant. In some embodiments, the lipid comprises a cationic lipid, and the oil comprises squalene, and/or the hydrophobic surfactant comprises sorbitan ester. In some embodiments, nanoparticles provided herein comprise a ratio of the esters that yields a hydrophilic-lipophilic balance between 8 and 11. In some embodiments, nucleic acids provided herein are incorporated, associated with, or complexed a lipid carrier provided herein to form a lipid carrier-nucleic acid complex. In some embodiments, the lipid carrier-nucleic acid complex is formed via non-covalent interactions or via reversible covalent interactions.

Nucleic Acids

In some embodiments, a composition described herein comprise one or more nucleic acids. In some embodiments, the nucleic acid a DNA or an RNA. A variety of RNAs can be associated with the lipid carrier particles for delivery, including RNAs that modulate innate immune responses, RNAs that encode proteins or antigens, silencing RNAs, microRNAs, tRNAs, self-replicating RNAs, etc. In specific aspects of the disclosure, the RNA is a self-replicating RNA.

Provided herein are compositions comprising a nanoparticle and a nucleic acid. In some embodiments, the nucleic acid is in complex with the nanoparticle. In some embodiments, the nucleic acid is in complex with the membrane of the nanoparticle. In some embodiments, the nucleic acid is in complex with the hydrophilic surface of the nanoparticle. In some embodiments, the nucleic acid is within the nanoparticle. In some embodiments, the nucleic acid is within the hydrophobic core.

In some embodiments, the one or more nucleic acid encodes an RNA or DNA polymerase. In some embodiments, the one or more nucleic acid encodes an RNA dependent RNA polymerase. In some embodiments, one or more nucleic acid encode an element for self-replication, such as an RNA polymerase (e.g., a VEEV polymerase).

The self-replicating nucleotide generally contains at least one or more genes selected from the group consisting of viral replicases, viral proteases, viral helicases and other nonstructural viral proteins, and also comprises 5'- and 3'-end cis-active replication sequences, and an antigenic sequence encoding a cancer-associated protein. A subgenomic promoter that directs expression of the heterologous sequence(s) can be included in the self-replicating nucleotide sequence. If desired, a heterologous sequence may be fused in frame to other coding regions in the self-replicating RNA and/or may be under the control of an internal ribosome entry site (IRES).

In various embodiments, the self-replicating nucleotide sequence is a self-replicating RNA molecule. Self-replicating RNA molecules of the disclosure can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sindbis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the disclosure can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus, the delivered RNA leads to the production of multiple daughter RNAs. These transcripts are antisense relative to the delivered RNA and may be translated themselves to provide in situ expression of encoded cancer-associated protein, or may be transcribed to provide further transcripts with the same sense as the delivered RNA which are translated to provide in situ expression of the encoded cancer-associated protein(s).

If desired, a self-replicating RNA can contain chemical modifications in or on the sugar moiety of the nucleoside (e.g., ribose, deoxyribose, modified ribose, modified deoxyribose, six-membered sugar analog, or open-chain sugar analog), or the phosphate.

The self-replicating RNA molecules of the disclosure can contain one or more modified nucleotides and therefore have improved stability and be resistant to degradation and clearance in vivo, and other advantages. Without wishing to be bound by any particular theory, it is believed that self-replicating RNA molecules that contain modified nucleotides avoid or reduce stimulation of endosomal and cytoplasmic immune receptors when the self-replicating RNA is delivered into a cell. This permits self-replication, amplification and expression of protein to occur. This also reduces safety concerns relative to self-replicating RNA that does not contain modified nucleotides, because the self-replicating RNA that contains modified nucleotides reduce activation of the innate immune system and subsequent undesired consequences (e.g., inflammation at injection site, irritation at injection site, pain, and the like). It is also believed that the RNA molecules produced as a result of self-replication are recognized as foreign nucleic acids by the cytoplasmic immune receptors. Thus, self-replicating RNA molecules that contain modified nucleotides provide for efficient amplification of the RNA in a host cell and expression of cancer-associated protein, as well as adjuvant effects.

The RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methyltransferase, which catalyzes the construction of N7-monomethylated cap 0 structures). Cap structure can provide stability and translational efficacy to the RNA molecule. The 5' cap of the RNA molecule may be further modified by a 2'-O-Methyltransferase which results in the generation of a cap 1 structure (m7Gppp [m2'-O] N), which may further increases translation efficacy. A cap 1 structure may also increase in vivo potency.

As used herein, "modified nucleotide" refers to a nucleotide that contains one or more chemical modifications (e.g., substitutions) in or on the nitrogenous base of the nucleoside (e.g., cytosine (C), thymine (T) or uracil (U), adenine (A) or guanine (G)). If desired, a self-replicating RNA molecule can contain chemical modifications in or on the sugar moiety of the nucleoside (e.g., ribose, deoxyribose, modified ribose, modified deoxyribose, six-membered sugar analog, or open-chain sugar analog), or the phosphate.

The self-replicating RNA molecules can contain at least one modified nucleotide that, preferably, is not part of the 5' cap (e.g., in addition to the modification that are part of the 5" cap). Accordingly, the self-replicating RNA molecule can contain a modified nucleotide at a single position, can contain a particular modified nucleotide (e.g., pseudouridine, N6-methyladenosine, 5-methylcytidine, 5-methyluridine) at two or more positions, or can contain two, three, four, five, six, seven, eight, nine, ten or more modified nucleotides (e.g., each at one or more positions). Preferably, the self-replicating RNA molecules comprise modified nucleotides that contain a modification on or in the nitrogenous base, but do not contain modified sugar or phosphate moieties.

In some examples, between 0.001% and 99% or 100% of the nucleotides in a self-replicating RNA molecule are modified nucleotides. For example, 0.001%-25%, 0.01%-25%, 0.1%-25%, or 1%-25% of the nucleotides in a self-replicating RNA molecule are modified nucleotides.

In other examples, between 0.001% and 99% or 100% of a particular unmodified nucleotide in a self-replicating RNA molecule is replaced with a modified nucleotide. For example, about T % of the nucleotides in the self-replicating RNA molecule that contain uridine can be modified, such as by replacement of uridine with pseudouridine. In other examples, the desired amount (percentage) of two, three, or four particular nucleotides (nucleotides that contain uridine, cytidine, guanosine, or adenine) in a self-replicating RNA molecule are modified nucleotides. For example, 0.001%-25%, 0.01%-25%, 0.1%-25, or 1%-25% of a particular nucleotide in a self-replicating RNA molecule are modified nucleotides. In other examples, 0.001%-20%, 0.001%-15%, 0.001%-10%, 0.01%-20%, 0.01%-15%, 0.1%-25, 0.01%-10%, 1%-20%, 1%-15%, 1%-10%, or about 5%, about 10%, about 15%, about 20% of a particular nucleotide in a self-replicating RNA molecule are modified nucleotides.

It is preferred that less than 100% of the nucleotides in a self-replicating RNA molecule are modified nucleotides. It is also preferred that less than 100% of a particular nucleotide in a self-replicating RNA molecule are modified nucleotides. Thus, preferred self-replicating RNA molecules comprise at least some unmodified nucleotides.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); hoSU (5-hydroxyuridine); moSU (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Any one or any combination of these modified nucleobases may be included in the self-replicating RNA of the disclosure. Many of these modified nucleobases and their corresponding ribonucleosides are available from commercial suppliers.

In some embodiments, the RNA molecule, optionally the self-replicating RNA molecule, comprises phosphoramidate, phosphorothioate, and/or methylphosphonate linkages.

Self-replicating RNA molecules that comprise at least one modified nucleotide can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., using a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid-ammonium acetate pH 3.5), buffer B (20 mM acetic acid-ammonium acetate pH 3.5/methanol [90/10])).

The self-replicating RNA may be associated with a delivery system. The self-replicating RNA may be administered with or without an adjuvant.

The one or more nucleic acid may be incorporated/associated/complexed with the lipid carrier to form a lipid carrier-nucleic acid complex. The lipid carrier-nucleic acid complex is formed via non-covalent interactions or via reversible covalent interactions.

In some embodiments, compositions provided herein comprise one or more nucleic acids. In some embodiments, compositions provided herein comprise two or more nucleic acids. In some embodiments, compositions provided herein comprise at least one DNA. In some embodiments, compositions provided herein comprise at least one RNA. In some embodiments, compositions provided herein comprise at least one DNA and at least one RNA. In some embodiments, nucleic acids provided herein are present in an amount of above 5 ng to about 1 mg. In some embodiments, nucleic acids provided herein are present in an amount of up to about 25, 50, 75, 100, 150, 175 ng. In some embodiments, nucleic acids provided herein are present in an amount of up to about 1 mg. In some embodiments, nucleic acids provided herein are present in an amount of about 0.05 µg, 0.1 µg, 0.2 µg, 0.5, µg 1 µg, 5 µg, 10 µg, 12.5 µg, 15 µg, 25 µg, 40 µg, 50 µg, 100 µg, 200 µg, 300 µg, 400 µg, 500 µg, 600 µg, 700 µg, 800 µg, 900 µg, 1 mg. In some embodiments, nucleic acids provided herein are present in an amount of 0.05 µg, 0.1 µg, 0.2 µg, 0.5, µg 1 µg, 5 µg, 10 µg, 12.5 µg, 15 µg, 25 µg, 40 µg, 50 µg, 100 µg, 200 µg, 300 µg, 400 µg, 500 µg, 600 µg, 700 µg, 800 µg, 900 µg, 1 mg. In some embodiments, nucleic acids provided herein are present in an amount of about 5 µg, about 10 µg, about 25 µg, about 50 µg, or about 100 µg. In some embodiments, nucleic acids provided herein are present in an amount of up to about 5 µg, about 10 µg, about 25 µg, about 50 µg, or 100 µg. In some embodiments, the nucleic acid is at least about 200, 250, 500, 750, 1000, 2000, 3000, 4000, 5000, 6000, 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is up to about 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is about 7500, 10,000, 15,000, or 20,000 nucleotides in length.

Cryoprotectants

In some embodiments, compositions and methods provided herein comprise at least one cryoprotectant. Exemplary cryoprotectants for inclusion are, but not limited to, sucrose, maltose, trehalose, mannitol, or glucose, and any combinations thereof. In some embodiments, additional or alternative cryoprotectant for inclusion is sorbitol, ribitol, erthritol, threitol, ethylene glycol, or fructose. In some embodiments, additional or alternative cryoprotectant for inclusion is dimethyl sulfoxide (DMSO), glycerol, propylene glycol, ethylene glycol, 3-O-methyl-D-glucopyranose (3-OMG), polyethylene glycol (PEG), 1,2-propanediol, acetamide, trehalose, formamide, sugars, proteins, and carbohydrates. In some embodiments, the cryoprotectant is present at about 10% w/v to about 20% w/v, preferably about 10% w/v to at about 20% w/v, and more preferably at about 10% w/v. In certain aspects of the disclosure, the cryoprotectant is sucrose. In some aspects of the disclosure, the cryoprotectant is maltose. In some aspects of the disclosure, the cryoprotectant is trehalose. In some aspects of the disclosure, the cryoprotectant is mannitol. In some aspects of the disclosure, the cryoprotectant is glucose. In some embodiments, the cryoprotectant is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the cryoprotectant is present in an amount of about 50 to about 500 mg. In some embodiments, the cryoprotectant is present in an amount of about 200 to about 300 mg. In some embodiments, the cryoprotectant is present in an amount of about 250 mg. In some embodiments, the cryoprotectant is present in amount of a lyophilized composition by weight of at least 50, 55, 60, 65, 70, 75, 80, 85, 90, 95 or more percent. In some embodiments, the cryoprotectant is present in amount of a lyophilized composition by weight of about 95%. In some embodiments, the cryoprotectant is present in amount of a lyophilized composition by weight of 80 to 98%, 85 to 98%, 90 to 98%, or 94 to 96%. In some embodiments, the cryoprotectant is a sugar. In some embodiments, the sugar is sucrose, maltose, trehalose, mannitol, or glucose. In some embodiments, the sugar is sucrose. In some embodiments, the sucrose is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the sucrose is present in an amount of about 50 to about 500 mg. In some embodiments, the sucrose is present in an amount of about 200 to about 300 mg. In some embodiments, the sucrose is present in an amount of about 250 mg. In some embodiments, the sucrose is present in amount of a lyophilized composition by weight of at least 50, 55, 60, 65, 70, 75, 80, 85, 90, 95 or more percent. In some embodiments, the sucrose is present in amount of a lyophilized composition by weight of about 95%. In some embodiments, the sucrose is present in amount of a lyophilized composition by weight of 80 to 98%, 85 to 98%, 90 to 98%, or 94 to 96%.

In some embodiments, compositions provided herein are thermally stable. A composition is considered thermally stable when the composition resists the action of heat or cold and maintains its properties, such as the ability to protect a nucleic acid molecule from degradation at given temperature. In some embodiments, compositions and vaccines provided herein are thermally stable at about 25 degrees Celsius or standard room temperature. In some embodiments, compositions and vaccines provided herein are thermally stable at about 45 degrees Celsius. In some embodiments, compositions and vaccines provided herein are thermally stable at about −20 degrees Celsius. In some embodiments, compositions and vaccines provided herein are thermally stable at about 2 degrees Celsius to about 8 degrees Celsius. In some embodiments, compositions and vaccines provided herein are thermally stable at a temperature of at least about −80 degrees Celsius, at least about −20 degrees Celsius, at least about 0 degrees Celsius, at least about 2 degrees Celsius, at least about 4 degrees Celsius, at least about 6 degrees Celsius, at least about 8 degrees Celsius, at least about 10 degrees Celsius, at least about 20 degrees Celsius, at least about 25 degrees Celsius, at least about 30 degrees Celsius, at least about 37 degrees Celsius, up to 45 degrees Celsius. In some embodiments, compositions and vaccines provided herein are thermally stable for at least about 5 day, at least about 1 week, at least about 2 weeks, at least about 1 month, up to 3 months. In some embodiments, compositions and vaccines provided herein are stored at a temperature of at least about 4° C. up to 37 degrees Celsius for at least about 5 day, at least about 1 week, at least about 2 weeks, at least about 1 month, up to 3 months. In some embodiments, compositions and vaccines provided herein are stored at a temperature of at least about 20 degrees Celsius up to 25 degrees Celsius for at least about 5 day, at least about 1 week, at least about 2 weeks, at least about 1 month, up to 3 months.

Combination Compositions

Provided herein are compositions comprising a nucleic acid described herein and a lipid carrier described herein. In some embodiments, the lipid carrier comprises NP-1. In some embodiments, the lipid carrier comprises NP-2. In some embodiments, the lipid carrier comprises NP-3. In some embodiments, the lipid carrier comprises NP-4. In some embodiments, the lipid carrier comprises NP-5. In some embodiments, the lipid carrier comprises NP-6. In some embodiments, the lipid carrier comprises NP-7. In some embodiments, the lipid carrier comprises NP-8. In some embodiments, the lipid carrier comprises NP-9. In some embodiments, the lipid carrier comprises NP-10. In some embodiments, the lipid carrier comprises NP-11. In some embodiments, the lipid carrier comprises NP-12. In some embodiments, the lipid carrier comprises NP-13. In some embodiments, the lipid carrier comprises NP-14. In some embodiments, the lipid carrier comprises NP-15. In some embodiments, the lipid carrier comprises NP-16. In some embodiments, the lipid carrier comprises NP-17. In some embodiments, the lipid carrier comprises NP-18. In some embodiments, the lipid carrier comprises NP-18. In some embodiments, the lipid carrier comprises NP-19. In some embodiments, the lipid carrier comprises NP-20. In some embodiments, the lipid carrier comprises NP-21. In some embodiments, the lipid carrier comprises NP-22. In some embodiments, the lipid carrier comprises NP-23 In some embodiments, the lipid carrier comprises NP-24. In some embodiments, the lipid carrier comprises NP-25. In some embodiments, the lipid carrier comprises NP-26. In some embodiments, the lipid carrier comprises NP-27. In some embodiments, the lipid carrier comprises NP-28. In some embodiments, the lipid carrier comprises NP-28. In some embodiments, the lipid carrier comprises NP-29. In some embodiments, the lipid carrier comprises NP-30. In some embodiments, the lipid carrier comprises NP-31. In some embodiments, the lipid carrier comprises any of NP-1 to NP-31 and a cryoprotectant. In some embodiments, the cryoprotectant is a sugar described herein. Compositions provided herein can be characterized by an nitrogen:phosphate (N:P) molar ratio. The N:P ratio is determined by the amount of cationic lipid in the nanoparticle which contain nitrogen and the amount of nucleic acid used in the composition which contain negatively charged phosphates. A molar ratio of the lipid carrier to the nucleic acid can be chosen to increase the delivery efficiency of the nucleic acid, increase the ability of the nucleic acid-carrying nanoemulsion composition to elicit an immune response to the antigen, increase the ability of the nucleic acid-carrying nanoemulsion composition to elicit the production of antibody titers to the antigen in a subject. In some embodiments, compositions provided herein have a molar ratio of the lipid carrier to the nucleic acid can be characterized by the nitrogen-to-phosphate molar ratio, which can range from about 0.01:1 to about 1000:1, for instance, from about 0.2:1 to about 500:1, from about 0.5:1 to about 150:1, from about 1:1 to about 150:1, from about 1:1 to about 125:1, from about 1:1 to about 100:1, from about 1:1 to about 50:1, from about 1:1 to about 50:1, from about 5:1 to about 50:1, from about 5:1 to about 25:1, or from about 10:1 to about 20:1 In some embodiments, the molar ratio of the lipid carrier to the nucleic acid, characterized by the nitrogen-to-phosphate (N:P) molar ratio, ranges from about 1:1 to about 150:1, from about 5:1 to about 25:1, or from about 10:1 to about 20:1. In some embodiments, the N:P molar ratio of the nanoemulsion composition is about 15:1. In some embodiments, the nanoparticle comprises a nucleic acid provided herein covalently attached to the membrane.

Compositions provided herein can be characterized by an oil-to-surfactant molar ratio. In some embodiments, the oil-to-surfactant ratio is the molar ratio of squalene:cationic lipid, hydrophobic surfactant, and hydrophilic surfactant. In some embodiments, the oil-to-surfactant ratio is the molar ratio of squalene:DOTAP, hydrophobic surfactant, and hydrophilic surfactant. In some embodiments, the oil-to-surfactant ratio is the molar ratio of squalene:DOTAP, sorbitan monostearate, and polysorbate 80. In some embodiments, the oil-to surfactant molar ratio ranges from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the oil-to-surfactant molar ratio is at least about 0.1:1, at least about 0.2:1, at least about 0.3:1, at least about 0.4:1, at least about 0.5:1, at least about 0.6:1, at least about 0.7:1. In some embodiments, the oil-to surfactant molar ratio is at least about 0.4:1 up to 1:1.

Compositions provided herein can be characterized by hydrophilic surfactant-to-cationic lipid ratio. In some embodiments, the hydrophilic surfactant-to-cationic lipid ratio ranges from about 0.1:1 to about 2:1, from about 0.2:1 to about 1.5:1,from about 0.3:1 to about 1:1, from about 0.5:1 to about 1:1, or from about 0.6:1 to about 1:1. Compositions provided herein can be characterized by hydrophobic surfactant-to-lipid (e.g., cationic lipid) ratio. In some embodiments, the hydrophobic surfactant-to-lipid ratio ranges from about 0.1:1 to about 5:1, from about 0.2:1 to about 3:1, from about 0.3:1 to about 2:1, from about 0.5:1 to about 2:1, or from about 1:1 to about 2:1. In some embodiments, the cationic lipid is DOTAP.

Further provided herein is a dried composition comprising a sorbitan fatty acid ester, an ethoxylated sorbitan ester, a cationic lipid, an immune stimulant, and an RNA. Further provided herein are dried compositions, wherein the dried composition comprises sorbitan monostearate (e.g., SPAN® 60), polysorbate 80 (e.g., TWEEN® 80), DOTAP, an immune stimulant, and an RNA.

Pharmaceutical Compositions

In one aspect, the disclosure provides a pharmaceutical composition comprising lipid carriers and, optionally, nucleic acids described herein. Optionally, the pharmaceutical composition can comprise a pharmaceutically acceptable carrier or excipient. As used herein the term "pharmaceutically acceptable carrier or excipient" includes solvents, dispersion media, coatings, antibacterial and antifungal agents, isotonic and absorption delaying agents, etc., compatible with pharmaceutical administration.

The pharmaceutical composition comprises the dried composition reconstituted in a suitable diluent and a pharmaceutically acceptable carrier. The diluent is aqueous. In preferred aspects, the diluent is water.

The disclosure also provides kits comprising the pharmaceutical composition and a delivery system for administration to a subject. The subject can be a mammal. In preferred aspects, the subject is human.

In another aspect, the disclosure provides a vaccine delivery system comprising the compositions comprising the pharmaceutical composition, as described herein, and optionally one or more vaccine adjuvant.

By complexation of the lipid carrier with the nucleic acid, the composition can be delivered to a cell. The cell can be in a subject in need. For instance, when the nucleic acid is a protein antigen or encodes a protein antigen, the composition carrying the nucleic acid can elicit an immune response in the subject against the antigen. The composition may do so by eliciting antibody titers to the antigen in the subject, for instance, by inducing neutralizing antibody titers in the subject.

The disclosure also relates to a method for generating an immune response in a subject, comprising administering a therapeutically effective amount of the pharmaceutical composition to the subject.

In one embodiment, the composition containing the lipid carrier, when administered in an effective amount to the subject, can elicit an immune response to the antigen equal to or greater than the immune response elicited when the nucleic acid is administered to the subject without the lipid carrier.

Without being bound by theory, the hydrophobic surfactants in the nanoemulsion composition may contribute to increase the ability of the nanoemulsion composition to deliver a nucleic acid to the cell or to increase the ability of the nanoemulsion composition carrying a nucleic acid to elicit an immune response in the subject against the antigen (when the nucleic acid is a protein antigen or encodes a protein antigen). For instance, the hydrophobic surfactants in the nanoemulsion composition may contribute to increase the ability of the nanoemulsion composition carrying a nucleic acid.

Another aspect of the disclosure relates to a method of treating or preventing an infection or disease in a subject, comprising administering a therapeutically effective amount of the pharmaceutical composition to the subject.

As discussed above, the inorganic solid nanoparticles, when containing a reporter element detectable via imaging methods, the resulting nanoemulsion particles can be imaged and tracked after the nanoemulsion particles are administered in the body. For instance, the inorganic solid nanoparticle may contain a reporter element detectable via magnetic resonance imaging (MRI), such as a paramagnetic, superparamagnetic, ferrimagnetic or ferromagnetic compound.

Accordingly, one aspect of the disclosure also relates to a method of imaging and/or tracking a nucleic acid delivery in a subject, comprising administering a therapeutically effective amount of the pharmaceutical composition to the subject.

The disclosure also provides methods for preparing and reconstituting a lyophilized composition and a spray-dried composition.

In some aspects of the disclosure, the compositions and methods are useful in treating a variety of diseases and disclosures.

Non-limiting examples of infections may include viral and non-viral infections. Examples of viral infections include, but not limited to Human Papillomavirus (HPV), Herpes Simplex Virus (HSV), Varicella-Zoster Virus (VZV), influenza virus, types and subtypes of influenza virus, Yellow Fever Virus (YFV), Zika Virus, West Nile Virus, Chikungunya Virus, Dengue, Respiratory Syncytial Virus (RSV), Human Immunodeficiency Virus (HIV), Severe Acute Respiratory Syndrome Coronavirus 2 (SARS-CoV-2) and its variants.

Examples of diseases include cancer associated with melanoma-associated antigen A gene such as MAGE-A1, MAGE-A3 and tyrosinase-related protein (TYRP) gene such as TYRP-1.

In some aspects of the disclosure, the composition and methods comprises one or more nucleic acid that encodes an antigen, wherein the antigen is derived from a bacterial infection, a bacterial disease, a viral infection, a viral disease, a protozoan infection, a protozoan disease, a non-communicable disease, one or more cancers, or an autoimmune disease.

In some aspects, the antigen is derived from a virus. The virus is selected from the group consisting of Human Papillomavirus (HPV), Herpes Simplex Virus (HSV), Varicella-Zoster Virus (VZV), influenza virus, types and subtypes of influenza virus, Yellow Fever Virus (YFV), Zika Virus, West Nile Virus, Chikungunya Virus, Dengue, Respiratory Syncytial Virus (RSV), Human Immunodeficiency Virus (HIV), Severe Acute Respiratory Syndrome Coronavirus 2 (SARS-CoV-2) and its variants.

Administration and Dosage

In an aspect, the dried compositions of the disclosure may be used to deliver a nucleic acid (e.g., an RNA, optionally a self-replicating RNA) to a cell or a subject, e.g., a mammal, including but not limited to humans, dogs, cats, livestock (e.g., cows, sheep, goats, pigs), horses, and the like. Exemplary amounts of total nucleic acid for incorporation in a composition described herein includes about 1, 2, 2.5, 5, 7.5, 10, 12.5, 15, 20, 25, 30, 35, 40, 45, 50 micrograms (μg) or more In some embodiments, a formulation described herein is prepared in a single container for administration. In some embodiments, a formulation described herein is prepared in two containers for administration, separating the formulation from the nanoparticle carrier.

As used herein, "container" includes vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Examples of such containers include glass and/or plastic sealed or re-sealable tubes and ampules, including those having a rubber septum or other sealing means that is compatible with withdrawal of the contents using a needle and syringe. In some implementations, the containers are RNase free.

In preferred embodiments, the dried composition is lyophilized. In some embodiments, the dried composition is spray-dried.

In some embodiments, the lyophilized composition is reconstituted by the methods described herein. In other embodiments, the spray-dried composition is reconstituted by the methods described herein.

In some embodiments, pharmaceutical compositions provided here are in a form which allows for the composition to be administered to a subject. In some embodiments, the pharmaceutical composition is in the form of a solid, semi-solid, liquid or gas (aerosol).

To deliver the nucleic acid to a cell or a subject, any suitable administration route may be employed. In some embodiments, the pharmaceutical composition described herein is formulated for administration and/or for use in administration via an intratumoral, subcutaneous, intradermal, intramuscular, inhalation/intranasal, intravenous, intraperitoneal, intracranial, or intrathecal route. In some embodiments, the pharmaceutical composition is administered parenterally. In some embodiments, the pharmaceutical composition is administered percutaneously. In other embodiments, the pharmaceutical composition is administered intramuscularly. In other embodiments, the pharmaceutical composition is administered intradermally. In other embodiments, the pharmaceutical composition is administered transdermally. In other embodiments, the pharmaceutical composition is administered subcutaneously. In other embodiments, the pharmaceutical composition is administered intranasally, e.g., via a nasal sprayer. In other embodiments, the pharmaceutical composition is administered orally, e.g., via drops.

In an aspect, any suitable dosage form may be used for delivery of the pharmaceutical composition described herein. In some embodiments, the pharmaceutical composition is provided in an injectable dosage form, such as a solution or suspension.

In other embodiments, the composition is provided in a dosage form which may be delivered via an inhaler, such as a solution, suspension, or powder, wherein the dosage form is formulated for delivery via an inhaler such as a metered-dose inhaler, a soft-mist inhaler, a nebulizer, or a dry powder inhaler.

In other embodiments, the composition is provided in a dosage form which may be delivered nasally, such as a solution, suspension, or powder, wherein the dosage form is formulated for nasal delivery via an atomizer or nasal pump bottle, or other suitable device for delivery of nasally administered pharmaceutical compositions.

In an aspect, any pharmaceutically acceptable carriers, preservatives, and/or other excipients may be used in a dosage form described herein for delivery of compositions of the present disclosure.

The disclosure also provides dried compositions that do not contain one or more inorganic nanoparticles. The dried composition comprises a sorbitan fatty acid ester, an ethoxylated sorbitan ester, a cationic lipid, an immune stimulant and a RNA. In specific aspects, the dried composition comprises sorbitan monostearate, polyoxyethylene (20) sorbitan monooleate, DOTAP, an immune stimulant, and a RNA.

In some aspects, the immune stimulant can decrease the total amount of protein produced, but can increase the immune response to a vaccine. In some aspects, the immune stimulant can increase the total amount of protein produced, but can decrease the immune response to a vaccine. In some aspects, the immune stimulant is squalene. In some aspects, the immune stimulant is a caprylic/capric triglyceride (MIGLYOL® 810) or a triglyceride ester of saturated coconut/palmkernel oil derived caprylic and capric fatty acids and plant derived glycerol (MIGLYOL® 812N).

Exemplary Embodiments

Provided herein are dried compositions, wherein the dried compositions comprise: (a) a lipid carrier, wherein the lipid carrier is a nanoemulsion comprising a hydrophobic core, one or more inorganic nanoparticles and one or more lipids; (b) one or more nucleic acids; and (c) at least one cryoprotectant. Further provided herein are dried compositions, wherein the compositions are lyophilized Further provided herein are dried compositions, wherein the compositions are spray-dried. Further provided herein are dried compositions, wherein the dried compositions are thermally stable. Provided herein are dried compositions, wherein the dried compositions are thermally stable at about 25 degrees Celsius. Provided herein are dried compositions, wherein the dried compositions are thermally stable at about 45 degrees Celsius. Provided herein are dried compositions, wherein the dried compositions are thermally stable at about −20 degrees Celsius. Provided herein are dried compositions, wherein the dried compositions are thermally stable from about 2 degrees Celsius to about 8 degrees Celsius. Further provided herein are dried compositions, wherein the dried compositions are thermally stable for at least 1 week, at least 2 weeks, and/or at least 1 month. Further provided herein are dried compositions, wherein the hydrophobic core of the composition comprises an oil. Further provided herein are dried compositions, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut/palmkernel oil derived caprylic and capric fatty acids and plant derived glycerol, dihydroisosqualene (DHIS), farnesene and squalane. Further provided herein are dried compositions, wherein the one or more inorganic nanoparticles is selected from the group consisting of: a metal salt, metal oxide, metal hydroxide, metal phosphate, and any combinations thereof. Further provided herein are dried compositions, wherein the one or more lipids is selected from the group consisting of: cationic lipids, anionic lipids, neutral lipids, and any combinations thereof. Further provided herein are dried compositions, wherein the one or more lipids is a cationic lipid. Further provided herein are dried compositions, wherein the cationic lipid is selected from the group consisting of: 1,2-dioleoyloxy-3-(trimethylammonium)propane (DO-TAP); 3β-[N-(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethyl-ammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are dried compositions, wherein the lipid carrier optionally comprises at least one surfactant. Further provided herein are dried compositions, wherein the at least one surfactant is selected from the group consisting of: a hydrophobic surfactant, a hydrophilic surfactant, and any combinations Further provided herein are dried compositions, wherein the hydrophobic surfactant comprises a sorbitan ester. Further provided herein are dried compositions, wherein the sorbitan ester is selected from the group consisting of: sorbitan monolaurate, sorbitan monopalmitate, sorbitan monostearate, sorbitan tristearate, sorbitan monooleate, and sorbitan trioleate; and the hydrophilic surfactant comprises a polysorbate. Further provided herein are dried compositions, wherein the lipid carrier has a z-average hydrodynamic diameter ranging from about 40 nm to about 150 nm, with an average polydispersity index ranging from about 0.1 to about 0.4. Further provided herein are dried compositions, wherein the one or more nucleic acid is an RNA. Further provided herein are dried compositions, wherein the RNA is a self-replicating RNA. Further provided herein are dried compositions, wherein the one or more nucleic acid is incorporated or complexed with the lipid carrier to form a lipid carrier-nucleic acid complex. Further provided herein are dried compositions, wherein the lipid carrier-nucleic acid complex is formed via non-covalent interactions or via reversible covalent interactions. Further provided herein are dried compositions, wherein the molar ratio of the lipid carrier to the one or more nucleic acids, characterized by the nitrogen-to-phosphate (N:P) molar ratio, ranges from about 1:1 to about 150:1. Further provided herein are dried compositions, wherein the at least one cryoprotectant is selected from the group consisting of: sucrose, maltose, trehalose, mannitol, glucose, and any combinations thereof. Further provided herein are dried compositions, wherein the at least one cryoprotectant is sucrose. Further provided herein are dried compositions, wherein the at least one cryoprotectant is at about 1% w/v to about 20% w/v. Further provided herein are dried compositions, wherein the at least one cryoprotectant is at about 1% w/v to about 40% w/v. Further provided herein are dried compositions, wherein the at least one cryoprotectant is at about 10% w/v to about 20% w/v. Further provided herein are dried compositions, wherein the at least one cryoprotectant is at about 10% w/v. Further provided herein are dried compositions, wherein the one or more inorganic nanoparticles comprises aluminum oxide ($Al_2O_3$), aluminum oxyhydroxide, iron oxide, titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. Further provided herein are compositions, wherein the one or more inorganic nanoparticles comprises magnetite ($Fe_3O_4$), maghemite ($\gamma$-$Fe_2O_3$), wustite (FeO), or hematite (alpha ($\alpha$)-$Fe_2O_3$), or combinations thereof.

Further provided herein are pharmaceutical compositions, wherein the pharmaceutical compositions comprise: a dried composition provided herein reconstituted in a suitable diluent; and a pharmaceutically acceptable carrier. Further provided herein are pharmaceutical compositions, wherein the suitable diluent is aqueous. Further provided herein are pharmaceutical compositions, wherein the suitable diluent is water.

Further provided herein are kits, wherein the kits comprise a pharmaceutical composition provided herein or a dried composition provided herein; and a delivery system for administration to a subject.

Further provided herein are vaccine delivery systems, wherein the vaccine delivery systems comprise: a pharmaceutical composition provided herein and optionally, one or more vaccine adjuvants.

Further provided herein are methods for generating an immune response in a subject, the methods comprising: administering to the subject a therapeutically effective amount of a pharmaceutical composition provided herein.

Further provided herein are methods of treating or preventing a disease in a subject, the methods comprising: administering to the subject a therapeutically effective amount of the pharmaceutical composition provided herein.

Further provided herein are methods of imaging and/or tracking delivery of one or more nucleic acids in a subject, the methods comprising: administering to the subject a therapeutically effective amount of the pharmaceutical composition provided herein.

Further provided herein are methods for preparing a lyophilized compositions, the methods comprising: (a) obtaining a lipid carrier, wherein the lipid carrier is a nanoemulsion comprising a hydrophobic core, optionally one or more inorganic nanoparticles and one or more lipids; (b) incorporating one or more nucleic acid into the lipid carrier to form a lipid carrier-nucleic acid complex; (c) adding at least one cryoprotectant to the lipid carrier-nucleic acid complex to form a formulation; and (d) lyophilizing the formulation to form a lyophilized composition.

Further provided herein are methods for preparing a spray-dried composition, the methods comprising: (a) obtaining a lipid carrier, wherein the lipid carrier is a nanoemulsion comprising a hydrophobic core, optionally one or more inorganic nanoparticles and one or more lipids; (b) incorporating one or more nucleic acid into the lipid carrier to form a lipid carrier-nucleic acid complex; (c) adding at least one cryoprotectant to the lipid carrier-nucleic acid complex to form a formulation; and (d) spray drying the formulation to form a spray-dried composition.

Further provided herein are methods for reconstituting a lyophilized composition, the methods comprising: (a) obtaining a lipid carrier, wherein the lipid carrier is a nanoemulsion comprising a hydrophobic core, optionally one or more inorganic nanoparticles, and one or more lipids; (b) incorporating one or more nucleic acid into the said lipid carrier to form a lipid carrier-nucleic acid complex; (c) adding at least one cryoprotectant to the lipid carrier-nucleic acid complex to form a formulation; lyophilizing the formulation to form a lyophilized composition; and (d) reconstituting the lyophilized composition in a suitable diluent. Further provided herein are methods, wherein the suitable diluent is aqueous. Further provided herein are methods, wherein the suitable diluent is water. Further provided herein are methods, wherein the lyophilized composition is thermally stable. Further provided herein are methods, wherein the lyophilized composition is thermally stable for at least 1 week, at least 2 weeks, and/or at least 1 month. Further provided herein are methods, wherein the lyophilized composition is thermally stable at about 25 degrees Celsius. Further provided herein are methods, wherein the lyophilized composition is thermally stable at about 45 degrees Celsius. Provided herein are methods, wherein the lyophilized composition is thermally stable at about 20 degrees Celsius. Further provided herein are methods, wherein the lyophilized composition is thermally stable at about 2 degrees Celsius to about 8 degrees Celsius. Further provided herein are compositions, wherein the one or more inorganic nanoparticles comprises aluminum oxide ($Al_2O_3$), aluminum oxyhydroxide, iron oxide, titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. Further provided herein are compositions, wherein the one or more inorganic nanoparticles comprises magnetite ($Fe_3O_4$), maghemite ($\gamma$-$Fe_2O_3$), wustite (FeO), or hematite (alpha ($\alpha$)-$Fe_2O_3$), or combinations thereof.

Further provided herein are methods for reconstituting a spray-dried composition, the methods comprising: (a) obtaining a lipid carrier, wherein the lipid carrier is a nanoemulsion comprising a hydrophobic core, optionally one or more inorganic nanoparticles, and one or more lipids; (b) incorporating one or more nucleic acid into the said lipid carrier to form a lipid carrier-nucleic acid complex; (c) adding at least one cryoprotectant to the lipid carrier-nucleic acid complex to form a formulation; (d) spray drying the formulation to form a spray-dried composition; and (e) reconstituting the spray-dried composition in a suitable diluent. Further provided herein are methods, wherein the diluent is aqueous. Further provided herein are methods, wherein the diluent is water. Further provided herein are methods, wherein the lyophilized composition is thermally stable. Further provided herein are methods, wherein the lyophilized composition is thermally stable at about 25 degrees Celsius. Further provided herein are methods, wherein the lyophilized composition is thermally stable at about 45 degrees Celsius. Provided herein are methods, wherein the lyophilized composition is thermally stable at about −20 degrees Celsius. Further provided herein are methods, wherein the lyophilized composition is thermally stable at about 2 degrees Celsius to about 8 degrees Celsius. Further provided herein are methods, wherein the hydrophobic core comprises an oil. Further provided herein are methods, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut/palmkernel oil derived caprylic and capric fatty acids and plant derived glycerol, dihydroisosqualene (DHIS), famesene and squalane. Further provided herein are methods, wherein the one or more lipids is selected from the group consisting of cationic lipids, anionic lipids, neutral lipids, and any combinations thereof. Further provided herein are methods, wherein the one or more lipids comprises a cationic lipid. Further provided herein are methods, wherein the cationic lipid is selected from the group consisting of 1,2-dioleoyloxy-3-(trimethylammonium)propane (DOTAP); 3β-[N-(N', N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2, 3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis (2-hydroxydodecyl)amino)ethyl) (2-hydroxydodecyl) amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are methods, wherein the lipid carrier optionally comprises one or more surfactant. Further provided herein are methods, wherein the one or more surfactant is selected from the group consisting of hydrophobic surfactant, hydrophilic surfactant, and any combinations thereof. Further provided herein are methods, wherein the hydrophobic surfactant comprises a sorbitan ester selected from the group consisting of sorbitan monolaurate, sorbitan monopalmitate, sorbitan monostearate, sorbitan tristearate, sorbitan monooleate, and sorbitan trioleate; and the hydrophilic surfactant comprises a polysorbate. Further provided herein are methods, wherein the lipid carrier has a z-average hydrodynamic diameter ranging from about 40 nm to about 150 nm, with an average polydispersity index ranging from about 0.1 to about 0.4. Further provided herein are methods, wherein the one or more nucleic acid is an RNA. Further provided herein are methods, wherein the RNA is a self-replicating RNA. Further provided herein are methods, wherein the one or more nucleic acid is incorporated or complexed with the lipid carrier to form a lipid carrier-nucleic acid complex. Further provided herein are methods, wherein the lipid carrier-nucleic acid complex is formed via non-covalent interactions or via reversible covalent interactions. Further provided herein are methods, wherein the at least one cryoprotectant is selected from the group consisting of sucrose, maltose, trehalose, mannitol, glucose, and any combinations thereof. Further provided herein are methods, wherein the at least one cryoprotectant is sucrose. Further provided herein are methods, wherein the at least one cryoprotectant is at about 1% w/v to at about 20% w/v. Further provided herein are methods, wherein the at least one cryoprotectant is at about 10% w/v to at about 20% w/v. Further provided herein are methods, wherein the at least one cryoprotectant is at about 10% w/v. Further provided herein are compositions, wherein the one or more inorganic nanoparticles comprises aluminum oxide ($Al_2O_3$), aluminum oxyhydroxide, iron oxide, titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. Further provided herein are compositions, wherein the one or more inorganic nanoparticles comprises magnetite ($Fe_3O_4$), maghemite (y-$Fe_2O_3$), wustite (FeO), or hematite (alpha ($\alpha$)-$Fe_2O_3$), or combinations thereof.

Further provided herein are dried compositions, wherein the dried compositions comprise: a sorbitan fatty acid ester, an ethoxylated sorbitan ester, a cationic lipid, an immune stimulant, and an RNA. Further provided herein are dried compositions, wherein the sorbitan fatty acid ester is sorbitan monostearate. Further provided herein are dried compositions, wherein the ethoxylated sorbitan ester is polyoxyethylene (20) sorbitan monooleate. Provided herein are dried compositions, wherein the cationic lipid is DOTAP. Further provided herein are dried compositions, wherein the immune stimulant is squalene. Further provided herein are dried compositions, wherein Further provided herein are dried compositions, wherein the ratio of the esters yields a hydrophilic-lipophilic balance between 8 and 11. Provided herein are dried compositions, wherein the ratio of esters and lipids yields a particle size between 30 nm and 200 nm. Further provided herein are dried compositions, wherein the ratio of esters and lipids yields a particle size between 40 nm and 70 nm. Further provided herein are compositions, wherein the one or more inorganic nanoparticles comprises aluminum oxide ($Al_2O_3$), aluminum oxyhydroxide, iron oxide, titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. Further provided herein are compositions, wherein the one or more inorganic nanoparticles comprises magnetite ($Fe_3O_4$), maghemite (y-$Fe_2O_3$), wustite (FeO), or hematite (alpha ($\alpha$)-$Fe_2O_3$), or combinations thereof.

Further provided herein are dried compositions, wherein the dried compositions comprise: sorbitan monostearate, polyoxyethylene (20) sorbitan monooleate, DOTAP, an immune stimulant, and a RNA. Further provided herein are dried compositions, wherein the immune stimulant decreases the total amount of protein produced, but increases the immune response to the vaccine. Further provided herein are dried compositions, wherein the dried composition comprises: sorbitan monostearate, polyoxyethylene (20) sorbitan monooleate, DOTAP, and squalene and no solid particles. Further provided herein are dried compositions, wherein the ratio of the esters yields a hydrophilic-lipophilic balance between 8 and 11. Further provided herein are dried compositions, wherein the particle size is between 30 nm and 200 nm. Further provided herein are dried compositions, wherein the N:P ratio is between 5 and 35. Further provided herein are dried compositions, wherein the immune stimulant increases the total amount of protein produced, but decreases the immune response to the vaccine. Further provided herein are dried compositions, wherein the immune stimulant is at least one of caprylic/capric triglyceride or a triglyceride ester of saturated coconut/palmkernel oil derived caprylic and capric fatty acids and plant derived glycerol. Further provided herein are compositions, wherein the one or more inorganic nanoparticles comprises aluminum oxide ($Al_2O_3$), aluminum oxyhydroxide, iron oxide, titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. Further provided herein are compositions, wherein the one or more inorganic nanoparticles comprises magnetite ($Fe_3O_4$), maghemite (y-$Fe_2O_3$), wustite (FeO), or hematite (alpha ($\alpha$)-$Fe_2O_3$), or combinations thereof.

Further provided here are dried compositions, wherein the dried compositions comprise: (a) a lipid carrier, wherein the lipid carrier is a nanoemulsion comprising a hydrophobic core and one or more lipids; (b) optionally one or more nucleic acid; and (c) at least one sugar present in amount of (i) at least about 50% by weight of the dried composition, or (ii) present in an amount of least 50 mg. Further provided herein are compositions, wherein the composition is lyophilized. Further provided herein are compositions, wherein the compositions are thermally stable at about 25 degrees Celsius. Further provided herein are compositions, wherein the compositions are thermally stable at about 45 degrees Celsius. Further provided herein are compositions, wherein the compositions are thermally stable at about −20 degrees Celsius. Further provided herein are compositions, wherein the compositions are thermally stable at about 2 degrees Celsius to about 8 degrees Celsius. Further provided herein are compositions, wherein the compositions are thermally stable for at least 1 week, at least 2 weeks, and/or at least 1 month. Further provided herein are compositions, wherein the hydrophobic core comprises an oil. Further provided herein are compositions, wherein the oil comprises at least one of $\alpha$-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut/palmkemel oil derived caprylic and capric fatty acids and plant derived glycerol, dihydroisosqualene (DHIS), farnesene and squalane. Further provided herein are compositions, wherein the one or more lipids is selected from the group consisting of cationic lipids, anionic lipids, neutral lipids, and any combinations thereof. Further provided herein are compositions, wherein the one or more lipids comprises a cationic lipid. Further provided herein are compositions, wherein the cationic lipid is selected from the group consisting of 1,2-dioleoyloxy-3-(trimethylammonium)propane (DOTAP); 3β-[N-(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-

((2-(4-(2-((2-(bis(2-hydroxydodecyl)amino)ethyl) (2-hydroxydodecyl)amino)ethyl)piperazin-1-yl)ethyl) azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are compositions, wherein the lipid carrier comprises at least one surfactant. Further provided herein are compositions, wherein the at least one surfactant is selected from the group consisting of: a hydrophobic surfactant, a hydrophilic surfactant, and any combinations thereof. Further provided herein are compositions, wherein the hydrophobic surfactant comprises a sorbitan ester selected from the group consisting of sorbitan monolaurate, sorbitan monopalmitate, sorbitan monostearate, sorbitan tristearate, sorbitan monooleate, and sorbitan trioleate; and the hydrophilic surfactant comprises a polysorbate. Further provided herein are compositions, wherein the lipid carrier has a z-average hydrodynamic diameter ranging from about 40 nm to about 150 nm, with an average polydispersity index ranging from about 0.1 to about 0.4. Further provided herein are compositions, wherein the one or more nucleic acid is DNA. Further provided herein are compositions, wherein the one or more nucleic acid is RNA. Further provided herein are compositions, wherein the RNA is a self-replicating RNA. Further provided herein, are compositions, wherein the hydrophobic core comprises one or more inorganic nanoparticles. Further provided herein are compositions, wherein the one or more inorganic nanoparticles is selected from the group consisting of: a metal salt, metal oxide, metal hydroxide, metal phosphate, and any combinations thereof. Further provided herein are compositions, wherein the one or more nucleic acid is incorporated or complexed with the lipid carrier to form a lipid carrier-nucleic acid complex. Further provided herein are compositions, wherein the lipid carrier-nucleic acid complex is formed via non-covalent interactions or via reversible covalent interactions. Further provided herein are compositions, wherein a molar ratio of the lipid carrier to the one or more nucleic acids, characterized by the nitrogen-to-phosphate (N:P) molar ratio, ranges from about 1:1 to about 150:1. Further provided herein are compositions, wherein the at least one sugar is selected from the group consisting of sucrose, maltose, trehalose, mannitol, glucose, and any combinations thereof. Further provided herein are compositions, wherein the at least one sugar is present in an amount of at least about 50, 60, 70, 80, 90, 100, 110, 120, 130, 140, 150, 160, 170, 180, 190, 200, 210, 220, 230, 240, 250, 260, 270, 280, 290, 300 or more mg. Further provided herein are compositions, wherein the at least one sugar is present in an amount of 50 mg to 250 mg. Further provided herein are compositions, wherein the at least one sugar is present in an amount of at least about 250 mg. Further provided herein are compositions, wherein the sugar is present in amount of the composition by weight of at least 50, 55, 60, 65, 70, 75, 80, 85, 90, 95% or more. Further provided herein are compositions, wherein the sugar is present in amount of the composition by weight of 80 to 98%, optionally 94 to 96%. Further provided herein are compositions, wherein the sugar is present in amount of the composition by weight of about 95%. Further provided herein are compositions, wherein the at least one sugar comprises sucrose. Further provided herein are compositions, wherein the one or more inorganic nanoparticles comprises aluminum oxide ($Al_2O_3$), aluminum oxyhydroxide, iron oxide, titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. Further provided herein are compositions, wherein the one or more inorganic nanoparticles comprises magnetite ($Fe_3O_4$), maghemite ($\gamma$-$Fe_2O_3$), wustite (FeO), or hematite (alpha ($\alpha$)-$Fe_2O_3$), or combinations thereof.

Further provided herein are compositions comprising: a nucleic acid present in an amount of up to about 200 micrograms (μg); a cationic lipid present in a concentration of up to about 1.5 mg/ml; iron oxide present in a concentration of up to about 0.01 mg/ml; squalene present in a concentration of up to about 1.88 mg/ml; sorbitan monostearate present in a concentration of up to about 1.86 mg/ml; polysorbate 80 present in a concentration of up to about 1.86 mg/ml; sucrose present in a concentration of up to about 50 mg/ml; and optionally, citric acid monohydrate present in a concentration of up to about 2.1 mg/ml. Further provided herein are compositions wherein the nucleic acid is RNA or DNA. Further provided herein are compositions wherein the nucleic acid is RNA and present in an amount of up to about 50 μg.

Further provided herein are kits, wherein the kits comprise a pharmaceutical composition provided herein and a delivery system for administration to a subject. Further provided herein are kits, wherein the kits comprise two or more separate units comprising the lipid carrier and the nucleic acid, respectively. Further provided herein are kits, wherein the kits comprise a unit that comprises the lipid carrier and the nucleic acid. Further provided herein are kits, wherein the kits further comprise a unit comprising a reagent for hydration of the dried composition Further provided herein are kits, wherein the reagent for hydration comprises water.

Further provided herein are methods for generating an immune response in a subject, wherein the methods comprise: administering to the subject a therapeutically effective amount of the pharmaceutical composition provided herein.

Further provided herein are methods of treating or preventing a disease in a subject, wherein the methods comprise: administering to the subject a therapeutically effective amount of the pharmaceutical composition provided herein.

Further provided herein are methods of imaging and/or tracking delivery of one or more nucleic acids in a subject, wherein the methods comprise: administering a therapeutically effective amount of the pharmaceutical composition described herein.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

Examples

Example 1. General Production Techniques and Materials Employed

The following materials were used in the manufacturing of a lipid carrier, wherein the lipid carrier is a nanoemulsion comprising a hydrophobic core, one or more inorganic nanoparticles and one or more lipids.

Agents include: squalene, sorbitan monostearate, (SPAN® 60), polyoxyethylene (20) sorbitan monooleate (TWEEN® 80), DOTAP chloride, iron oxide nanoparticles and sodium citrate dihydrate. In general, to iron oxide nanoparticles with a number-weighted average diameter of 5 nm, chloroform was added. Chloroform was allowed to evaporate in a fume hood leaving behind a dry coating of iron oxide nanoparticles. To the iron oxide nanoparticles, SPAN® 60, squalene, and DOTAP chloride were added to prepare the "oil" phase. The oil phase was sonicated 30 minutes in a water bath pre-heated to 60° C. Separately, in a 1 liter glass bottle, the "aqueous" phase was prepared by adding TWEEN® 80 to sodium citrate dihydrate solution prepared with Milli-Q water. The aqueous phase was stirred for 30 minutes to allow complete dissolution of TWEEN® 80. After complete dissolution of TWEEN® 80, the aqueous phase was transferred to a beaker and incubated in a water bath pre-heated to 60° C. To the heated oil phase, the pre-heated aqueous phase was added. The mixture was immediately emulsified using a VWR 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 59 nm with a 0.2 polydispersity index. The microfluidized lipid carrier sample was terminally filtered with a 200 nm pore-size polyethersulfone (PES) syringe filter.

Example 2. Preparation of Lipid Carrier+RNA-Secreted Embryonic Alkaline Phosphatase (SEAP) Complex Lipid carrier+RNA-SEAP complexes were prepared and aliquoted in triplicate for lyophilization. Fe-lipid carrier described elsewhere herein includes 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml 12 nm oleic acid-coated iron oxide nanoparticles (Imagion Biosystems, San Diego, CA, USA) and 10 mM sodium citrate dihydrate (Fisher Chemical). The liquid samples were saved for comparison. Samples were collected and selected for reconstitution. The appearance of the lyophilized cakes was then recorded. All lyophilized cakes were then reconstituted in 0.7 ml milliQ water. The physicochemical properties of the reconstituted material including measurement of (i) particle size, (ii) size distribution, (iii) RNA integrity, (iv) DOTAP and squalene content, and (v) in vitro protein expression were then measured. The results are set forth below. Table 2 discloses the materials used in the preparation of lipid carrier+RNA-SEAP complex.

TABLE 2

Materials for the preparation of lipid carrier + RNA-SEAP complex.

| Name | Vendor (If Applicable) | Molecular weight | Concentration |
|---|---|---|---|
| Fe-lipid carrier | — | | 30 mg DOTAP/ml |
| NLC | — | | 30 mg DOTAP/ml |
| repRNA-SEAP (SEQ ID NO: 1) | — | | 1015 ng RNA/ul |
| Sucrose | EMD Millipore | 342.3 | |
| D-Glucose | J T Baker | 180.16 | |
| D-Mannitol | VWR | 182.17 | |

TABLE 2-continued

Materials for the preparation of lipid carrier + RNA-SEAP complex.

| Name | Vendor (If Applicable) | Molecular weight | Concentration |
|---|---|---|---|
| Maltose monohydrate | Sigma | 360.31 | |
| Trehalose dihydrate | Sigma | 378.33 | |
| Sodium citrate | Teknova | | 1M |

The conditions for lyophilization are set forth as below in Tables 3 to 5.

TABLE 3

Lyophilization cycle # 1.

| Time [hr] | T [C.] | P [mTorr] |
|---|---|---|
| 0 | 20 | 760000 |
| 1.5 | −50 | 760000 |
| 2 | −50 | 760000 |
| 2.1 | −50 | 50 |
| 2.5 | −30 | 50 |
| 20 | −30 | 50 |
| 20.5 | 25 | 50 |
| 22 | 25 | 50 |
| 22.1 | 25 | 760000 |

TABLE 4

Lyophilization cycle # 2.

| Time [hr] | T [C.] | P [mTorr] |
|---|---|---|
| 0 | 20 | 760000 |
| 1.5 | −65 | 760000 |
| 2 | −65 | 760000 |
| 2.1 | −65 | 15 |
| 2.5 | −50 | 15 |
| 24 | −50 | 15 |
| 24.5 | 25 | 15 |
| 26 | 25 | 15 |
| 26.1 | 25 | 760000 |

TABLE 5

Lyophilization cycle # 3.

| Time [hr] | T [C.] | P [mTorr] |
|---|---|---|
| 0 | 20 | 760000 |
| 1.5 | −65 | 760000 |
| 2 | −65 | 760000 |
| 2.1 | −65 | 15 |
| 2.5 | −50 | 15 |
| 26.5 | −50 | 15 |
| 26.6 | −30 | 15 |
| 46 | −30 | 15 |
| 48 | 25 | 15 |
| 48.1 | 25 | 760000 |

Preparation of diluents: The diluents comprising the sugar and citrate were prepared as outlined in Table 6. Each sugar was weighed out in a 50 ml RNase free conical tube. About 35-40 ml of nuclease free water was added to dissolve the sugar and slight heat and sonication was used, as needed. Pipette-in 0.5 ml of 1M Na-citrate, pH=6 solution. After all sugar has dissolved and solution is clear, Q.S. with nuclease free water to 50 ml mark in conical tube. Filter diluents with 0.22 μm STERIFLIP® and screw on cap aseptically to maintain sterility.

TABLE 6

Preparation of diluents.

| Diluent | Composition ID | Total Volume [ml] | Actual mass [g] | Calculated conc [g/L] |
|---|---|---|---|---|
| 22% sucrose/ 10 mM citrate | 22% sucrose | 50.0 | 11.1 | 222.0 |
| 50% sucrose/ 10 mM citrate | 50% sucrose | 50.0 | 25.0 | 500.0 |
| 22% maltose/ 10 mM citrate | 22% maltose | 50.0 | 11.7 | 233.7 |
| 22% trehalose/ 10 mM citrate | 22% trehalose | 50.0 | 12.3 | 245.4 |
| 11% glucose/ 10 mM citrate | 11% glucose | 50.0 | 5.6 | 111.0 |
| 11% mannitol/ 10 mM citrate | 11% mannitol | 50.0 | 5.6 | 111.0 |

Preparation of pre-complex formulation: Lipid carrier "DS" is the bulk solution at 30 mg DOTAP/ml and refers to Fe-lipid carrier formulation, whose preparation is described in Example 8.

Lipid carrier "DS" (30 mg DOTAP/ml) 10-fold was diluted in each diluent to make 3 mg DOTAP/ml lipid carrier "DP", except in 50% sucrose composition lipid carrier 5-fold was diluted to make 2×6 mg DOTAP/ml lipid carrier "DP". The target RNA concentration in liquid formulation was 50 ng/ul, complexed with lipid carrier at N:P of 15. This simulates 25 µg RNA dose per vial. Table 7 disclose the preparation of pre-complex lipid carrier complex. The unused lipid carrier was stored at 2-8 degrees Celsius.

TABLE 7

Pre-complex lipid carrier preparation.

| Composition ID | Lipid Carrier DS [ul] | Diluent [ul] | Total [ul] |
|---|---|---|---|
| 22% sucrose | 420 | 3780 | 4200 |
| 50% sucrose | 420 | 1680 | 2100 |
| 22% maltose | 420 | 3780 | 4200 |
| 22% trehalose | 420 | 3780 | 4200 |
| 11% glucose | 420 | 3780 | 4200 |
| 11% mannitol | 420 | 3780 | 4200 |
| Maltose monohydrate | Sigma | | 360.31 |
| Trehalose dihydrate | sigma | | 378.33 |
| Sodium citrate | Teknova | | 1M |

Table 8 discloses the preparation of pre-complex nanostructured lipid carrier (NLC) complex. The NLCs were used as control. The unused NLC was stored at 2-8 degrees Celsius for fresh complex controls.

TABLE 8

Pre-complex NLC preparation.

| Composition ID | NLC [ul] | Diluent [ul] | Total [ul] |
|---|---|---|---|
| 22% sucrose | 420 | 3780 | 4200 |

The preparation of RNA pre-complex is disclosed in Table 9. The RNA stock was prepared. About 7.5 ml or 0.63 ml for 50% sucrose per aliquot were split and stored at −80 degrees Celsius.

TABLE 9

Preparation of RNA pre-complex.

| Composition ID | RNA Stock [ul] | 5 mM citrate [ul] | Total [ul] | Actual RNA concentration pre-complex [ng/ul] |
|---|---|---|---|---|
| all | 2141.4 | 19593.6 | 21735.0 | 107.3 |
| 50% sucrose | 356.9 | 1454.4 | 1811.3 | 221.0 |

The preparation of lipid carrier-RNA complex is disclosed in Table 9. The RNA stock was prepared. The volume of diluted RNA was (+5%) and diluted lipid carrier was (+5%) per complexing per lyophilization (lyo) cycle.

Complexes of lipid carrier+RNA or NLC+RNA were prepared by mixing 1:1 by volume each diluted formulation listed in the above described Table 8 and Table 9, with the corresponding "Composition ID" diluted RNA disclosed in Table 10. The complexes were equilibrated for 30 minutes at room temperature before subjecting to the lyophilization cycles or long-term storage conditions.

TABLE 10

Preparation of lipid carrier-RNA pre-complex.

| Composition ID | Diluted RNA | Diluted lipid carrier | Diluted NLC [ul] | Total [ul] | Final RNA conc. [ng/ul] | Final Sugar conc. [% w/v] |
|---|---|---|---|---|---|---|
| 22% sucrose | 1102.5 | 1102.5 | | 2205 | 50 | 10 |
| 50% sucrose | 551.25 | 551.25 | | 1102.5 | 100 | 20 |
| 22% maltose | 1102.5 | 1102.5 | | 2205 | 50 | 10 |
| 22% trehalose | 1102.5 | 1102.5 | | 2205 | 50 | 10 |
| 11% glucose | 1102.5 | 1102.5 | | 2205 | 50 | 5 |
| 11% mannitol | 1102.5 | 1102.5 | | 2205 | 50 | 5 |
| 22% sucrose | 1102.5 | | 1102.5 | 2205 | 50 | 10 |

Example 3: Particle Size Measurements

The formulation was diluted 100-fold by adding 900 µl milliQ water to 10 µl GLB51-F04-20-02 in a disposable sizing cuvette DTS0012. Vortex and bubbles were removed by lightly tapping cuvette. Particle size was measured by MALDS method in the zetasizer ULTRA. A minimum of 5 measurements were collected. Average z-average diameter and average PDI were recorded from back scattering (173°) measurements.

Example 4: RNA Integrity by Agarose Gel Electrophoresis

Samples were prepared by diluting 50 ng/µl complex 5-fold to 10 ng/µl in nuclease free water: 12 µl complex+48 µl water. 60 µl of phenol:chloroform was added and invert 10-15 times to extract RNA. Centrifuged for 15 minutes to remove 10 µl supernatant and combined with 10 µl glyoxal load dye, followed by denaturing of RNA by heating to 50 degrees Celsius for 30 min. Loaded 10 µl per lane.

Example 5: SEAP Expression in BHK21 Cells

Cell transfection: A 96-well plate was pre-seeded with $1.5 \times 10^5$ cells/mL one day prior to transfection. On the day of transfection, the growth media was removed from the plate by pipetting. 50 µL RNA:lipid carrier mixtures and 50 µL of Opti-MEM™ (Thermo Fisher Scientific, Waltham, MA USA) were added to the BHK21 (baby hamster kidney fibroblast) cells. Cells were incubated for 4 hours. RNA: lipid carrier and Opti-MEM™ media was removed by pipetting and replaced with DMEM growth media. Cells were incubated overnight.

Evaluation of SEAP expression in supernatants: SEAP Reporter Assay Kit™ (Novus Biologicals NPB2-25285) kit was used to measure SEAP levels in supernatants. Supernatants were analyzed undiluted according to manufacturer's recommended protocol.

Example 6: Characterization Data after Cycle #1

Figure 2:
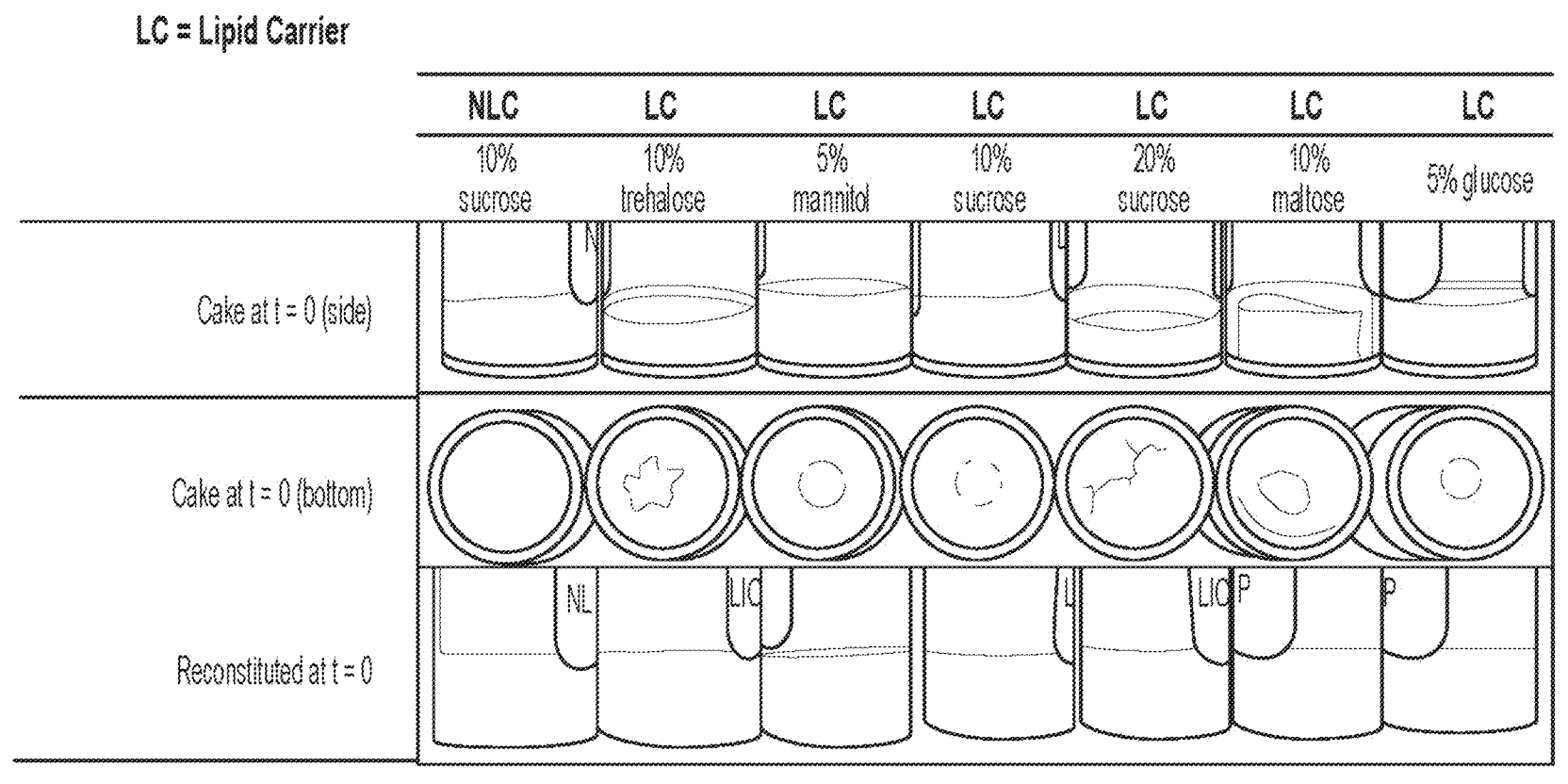
Figure 3:
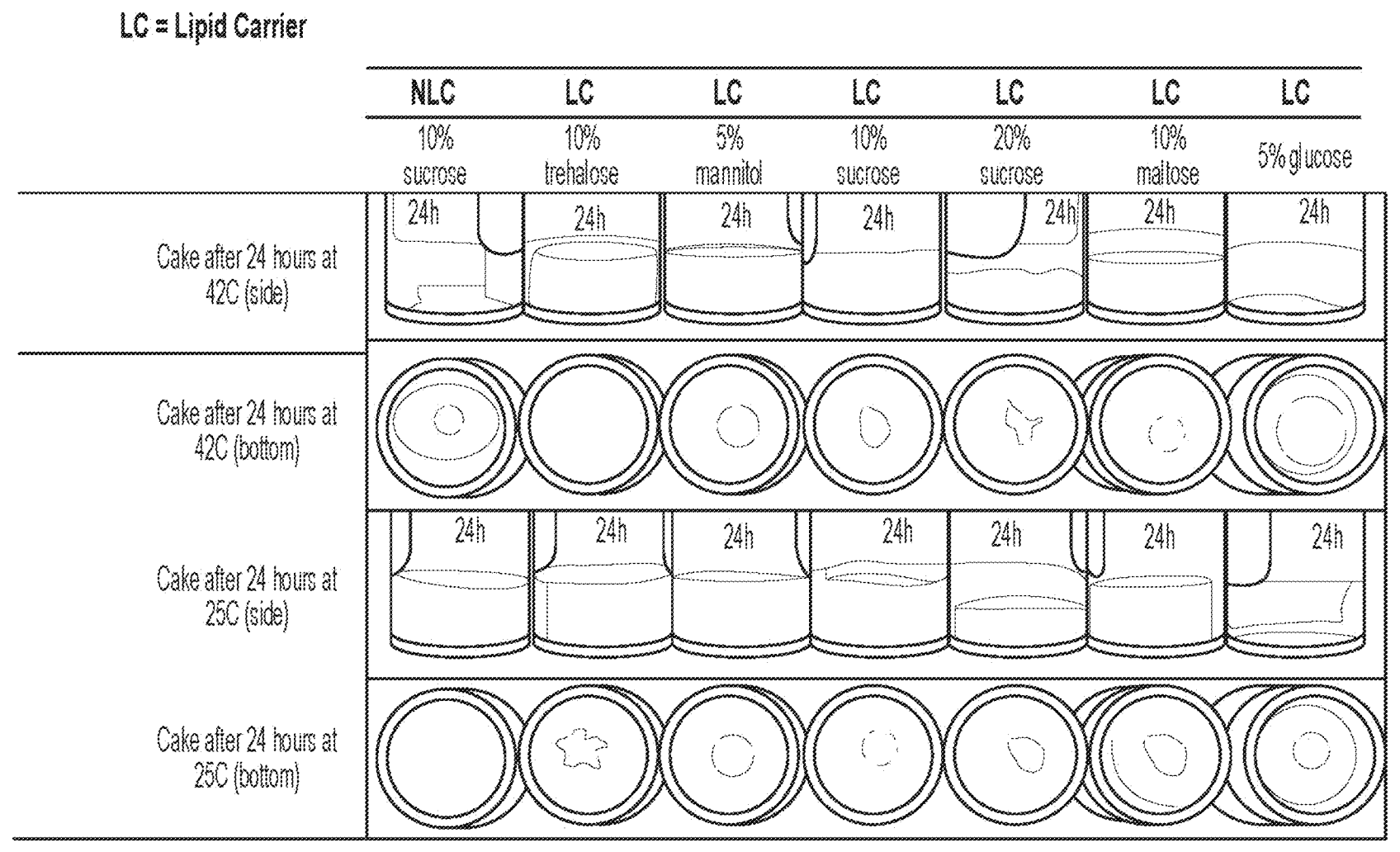
Figure 4:
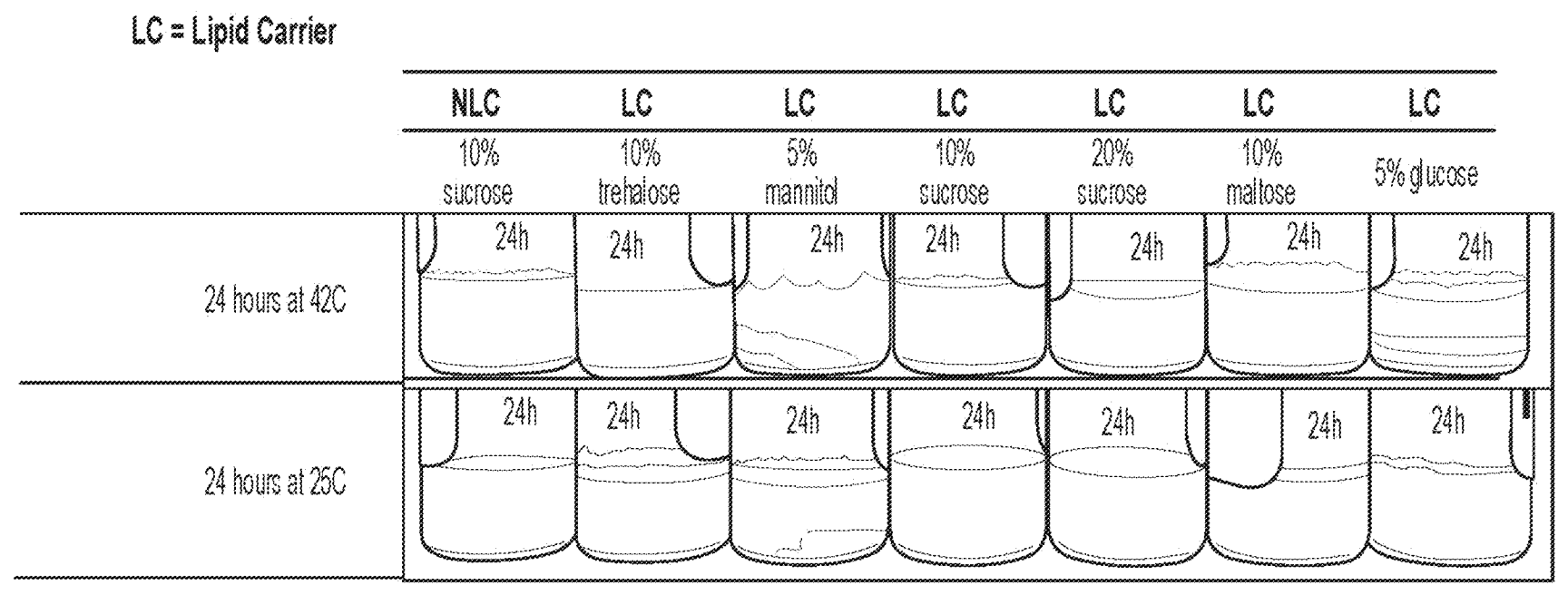

All lyophilized cakes showed good integrity at time=0 hr after cycle #1. Integrity of lipid carrier+RNA-SEAP in 5% glucose was partially compromised after 24 hours at 25 degrees Celsius. Integrity of all other formulations was preserved. Fe-lipid carrier described elsewhere herein includes 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml 12 nm oleic acid-coated iron oxide nanoparticles (Imagion Biosystems) and 10 mM sodium citrate dihydrate (Fisher Chemical). Cakes from NLC+RNA-SEAP in 10% sucrose and lipid carrier+RNA-SEAP in 5% glucose formulations shrank noticeably after 24 hours at 42 degrees Celsius. Integrity of all other formulations was preserved. FIGS. 2-4 illustrate the appearance of lyophilized cake in the indicated sugar composition after lyophilization cycle #1. FIG. 2 illustrates the appearance of NLC and lipid carrier cake in the indicated sugar composition at time=0 hr. FIG. 3 illustrates the appearance of NLC and lipid carrier cake in the indicated sugar composition after 24 hr at t=25 degrees Celsius and 42 degrees Celsius. FIG. 4 illustrates the appearance of NLC and lipid carrier cake in the indicated sugar composition at 24 hr at t=25 degrees Celsius and 42 degrees Celsius.

Figure 5A:
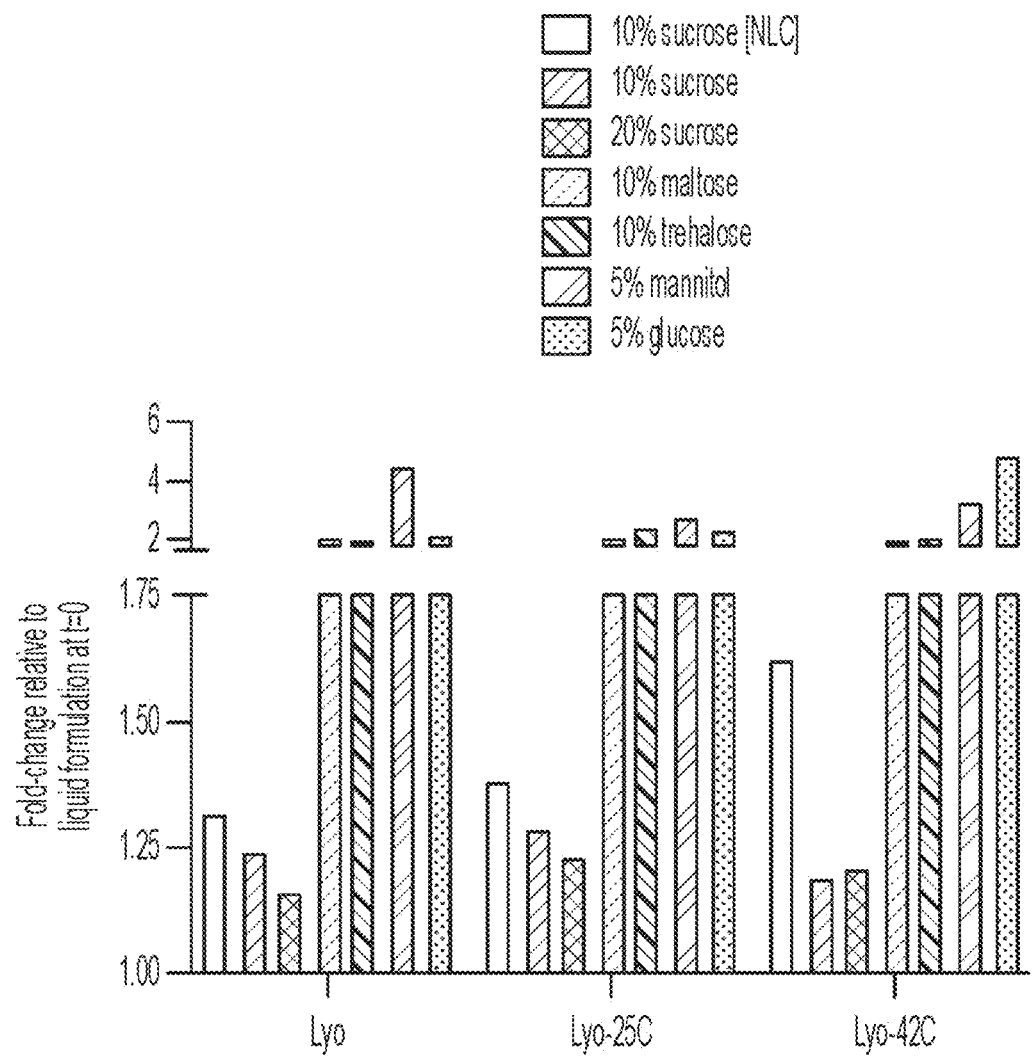
FIGS. 5A-5B illustrate the particle size of reconstituted cakes one day after storage at 25 degrees Celsius or 42 degrees Celsius in the indicated sugar compositions after lyophilization cycle #1.
Figure 5B:
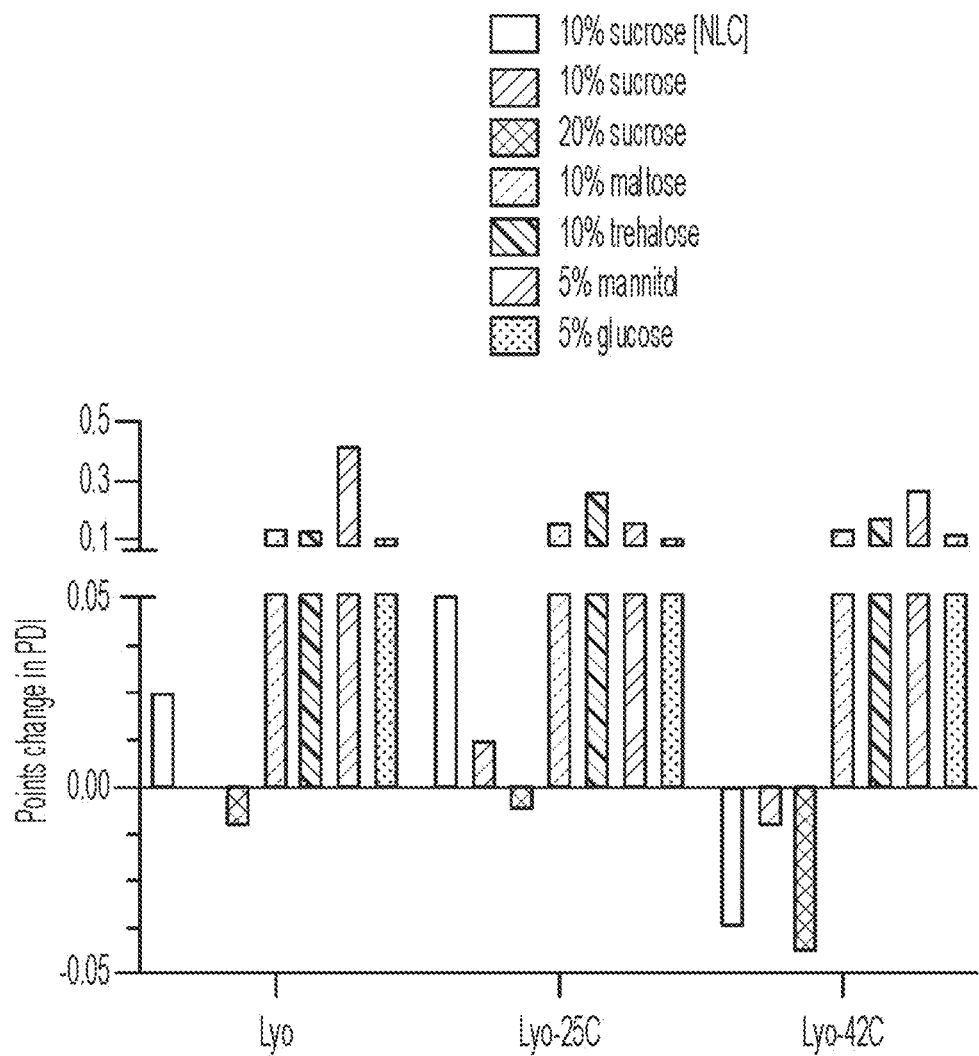

The particle size of reconstituted cakes one day after storage in the indicated sugar composition at 25 degrees Celsius or 42 degrees Celsius after lyophilization cycle #1 was measured as in FIGS. 4A-4B. FIG. 5A shows the fold-change in particle size relative to liquid formulation at time=0 hr in the indicated sugar compositions. FIG. 5B shows the points change in PDI of reconstituted lyophilized formulations relative to their corresponding liquid formulations in the indicated sugar compositions. Mean size and size distribution values are shown in Table 11. All reconstituted lyophilized formulations resulted in an increase in lipid carrier+RNA complex size after reconstitution. All reconstituted formulations containing sucrose as a cryoprotectant resulted in minimal PDI change at time=0 hr and 24 hours at 25 degrees Celsius.

Lyophilization (t=0) described in Table 11 refers to the lyophilized formulation reconstituted on the same day as completion of the lyophilization cycle. Liquid described in Table 11 refers to the equivalent liquid (un-lyophilized) formulation of the lyophilized formulation.

TABLE 11

Mean z-average Diameter and Mean PDI lyophilization cycle #1.

|  | 10% sucrose [NLC] | 10% sucrose [lipid carrier] | 20% sucrose [lipid carrier] | 10% maltose [lipid carrier] | 10% trehalose [lipid carrier] | 5% mannitol [lipid carrier] | 5% glucose [lipid carrier] |
|---|---|---|---|---|---|---|---|
| Mean z-average diameter [nm] | | | | | | | |
| Liquid | 74.7 | 80.5 | 98.1 | 76.3 | 77.3 | 74.7 | 73.6 |
| Lyo t = 0 | 98.3 | 99.8 | 113.3 | 158.9 | 153.0 | 327.1 | 153.2 |
| Lyo 24 hours at t = 25 degrees Celsius | 103.0 | 103.7 | 120.3 | 158.0 | 179.1 | 199.4 | 168.6 |
| Lyo 24 hours at t = 42 degrees Celsius | 121.1 | 95.4 | 118.2 | 153.7 | 157.5 | 238.4 | 353.0 |
| Mean PDI | | | | | | | |
| Liquid | 0.21 | 0.22 | 0.25 | 0.21 | 0.19 | 0.20 | 0.19 |
| Lyo t = 0 | 0.23 | 0.22 | 0.24 | 0.33 | 0.30 | 0.63 | 0.28 |
| Lyo 24 hours at t = 25 degrees Celsius | 0.26 | 0.23 | 0.24 | 0.36 | 0.45 | 0.35 | 0.27 |
| Lyo 24 hours at t = 42 degrees Celsius | 0.17 | 0.21 | 0.20 | 0.34 | 0.36 | 0.46 | 0.30 |

Figure 6A:
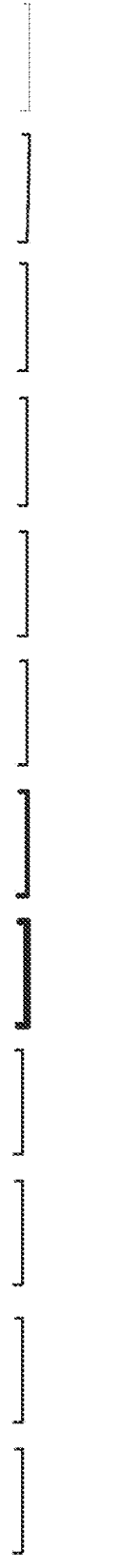
FIGS. 6A-6B illustrate the RNA integrity by agarose gel electrophoresis in the indicated sugar composition after lyophilization cycle #1 for lipid carrier+RNA and NLC+RNA formulations.
Figure 6B:
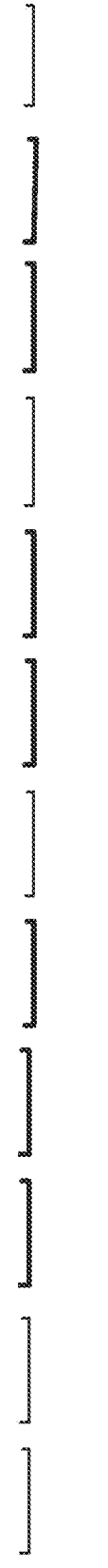

RNA Integrity by Agarose Gel Electrophoresis after Lyophilization Cycle #1:

The RNA integrity by agarose gel electrophoresis in the indicated sugar composition after lyophilization cycle #1 is illustrated in FIGS. 6A-6B for the lipid carrier+RNA and NLC+RNA formulations. FIG. 6A shows the RNA integrity by agarose gel electrophoresis in the indicated sugar composition after lyophilization cycle #1 for lipid carrier+RNA formulations. FIG. 6B shows the RNA integrity by agarose gel electrophoresis in the indicated sugar composition after lyophilization cycle #1 for lipid carrier+RNA and NLC+RNA formulations.

Lyophilized cakes at 25 degrees Celsius and 42 degrees Celsius were stored for 24 hours before reconstitution. All lyophilized samples after reconstitution and phenol:chloroform extraction of RNA-SEAP from lipid carrier+RNA-SEAP showed a defined RNA band that coincided with the naked RNA-SEAP positive control, as shown in FIGS. 6A-6B. FIG. 6A shows that the liquid formulation of lipid carrier+RNA-SEAP complex in 10% sucrose stored for 24 hours at 42 degrees Celsius resulted in significant decrease in RNA band intensity suggesting accelerated degradation when stored as a liquid but not when stored in the dried lyophilized form.

The lyophilization preserved RNA integrity in the liquid lipid carrier+RNA formulation at 42 degrees Celsius storage.

Figure 7A:
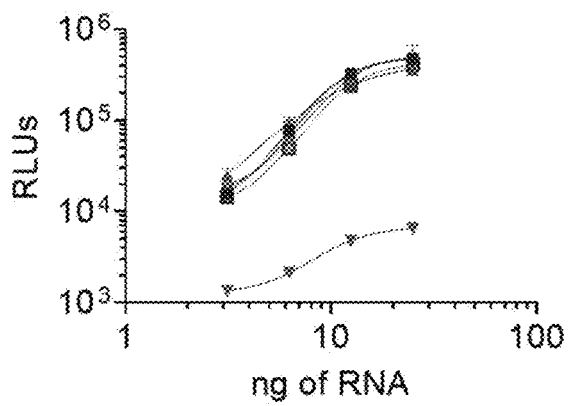
FIGS. 7A-7G illustrate the SEAP expression in BHK21 cells in the indicated sugar compositions after lyophilization cycle #1 for the lipid carrier+repRNA and NLC+repRNA-SEAP formulations.
Figure 7B:
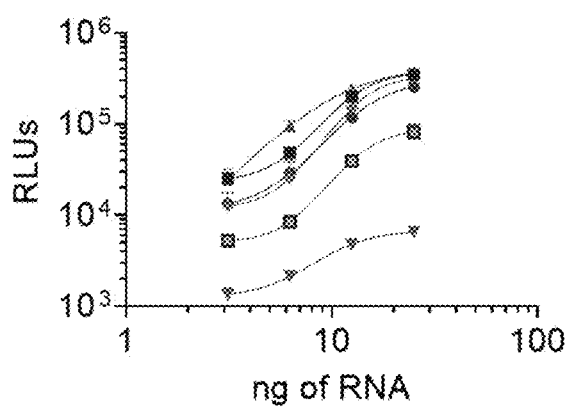
Figure 7C:
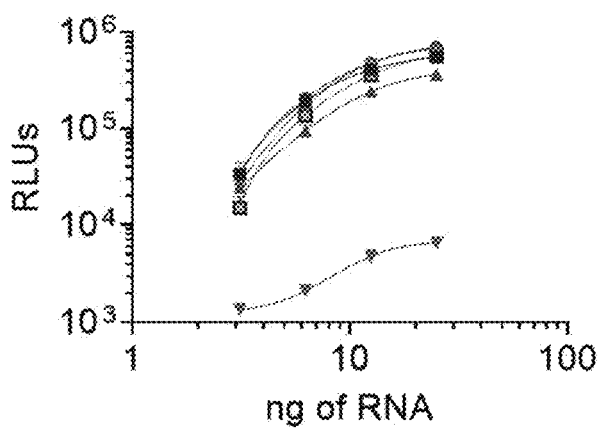
Figure 7D:
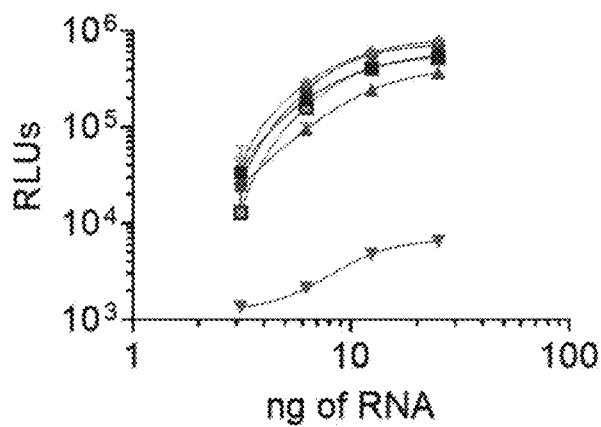
Figure 7E:
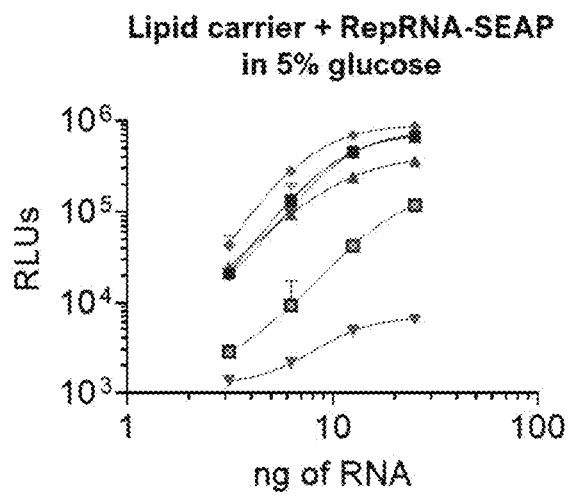
Figure 7F:
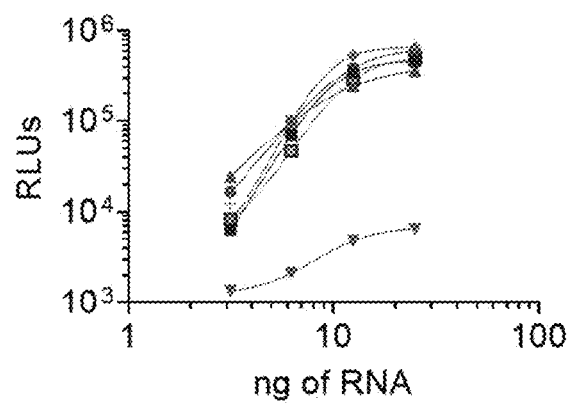
Figure 7G:
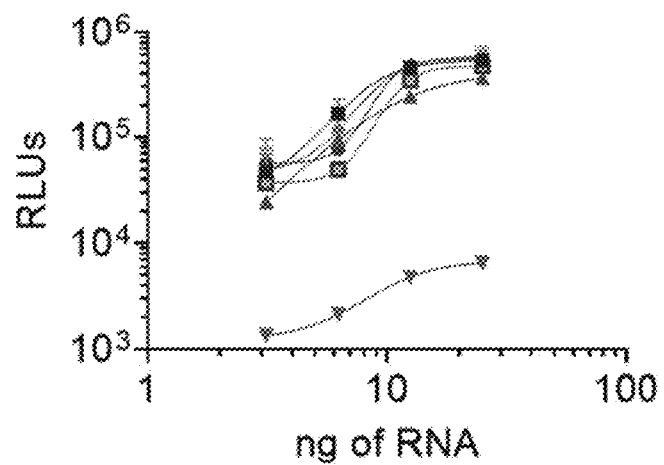

SEAP Expression in BHK21 Cells after Lyophilization Cycle #1:

The SEAP expression in BHK21 cells in the indicated sugar compositions after lyophilization cycle #1 for the lipid carrier+repRNA and NLC+repRNA-SEAP formulations is illustrated in FIGS. 7A-7G. FIG. 7A shows the Relative Luminescence Units (RLU) for the lipid carrier+repRNA-SEAP in 10% trehalose. FIG. 7B shows the Relative Luminescence Units (RLU) for the lipid carrier+repRNA-SEAP in 5% mannitol. FIG. 7C shows the Relative Luminescence Units (RLU) for the lipid carrier+repRNA-SEAP in 10% sucrose. FIG. 7D shows the Relative Luminescence Units (RLU) for the lipid carrier+repRNA-SEAP in 20% sucrose. FIG. 7E shows the Relative Luminescence Units (RLU) for the lipid carrier+repRNA-SEAP in 5% glucose. FIG. 7F shows the Relative Luminescence Units (RLU) for the lipid carrier+repRNA-SEAP in 10% maltose. FIG. 7G shows the Relative Luminescence Units (RLU) for the NLC+repRNA-SEAP in 10% sucrose.

For comparison, cells were transfected with freshly prepared lipid carrier+RNA-SEAP in the indicated sugar composition. As an additional stability comparison, cells were transfected with liquid formulation of lipid carrier+RNA-SEAP in 10% sucrose stored at 25 degrees Celsius for 24 hours or 42 degrees Celsius for 24 hours. The latter condition served as a comparison for measuring the effect of degraded RNA on in vitro protein expression. FIG. 7A-7G illustrate that all lyophilized formulations reconstituted at time=0 hr or after 24 hours at 25 degrees Celsius resulted in no change in the RNA dose-dependent expression profile relative to the corresponding freshly prepared lipid carrier+RNA-SEAP complex. Lipid carrier+RNA-SEAP in 10% sucrose (FIG. 7C) stored for 24 hours at 42 degrees Celsius in a liquid formulation resulted in significantly decreased SEAP expression compared to the lyophilized formulation. 10% trehalose (FIG. 7A), 20% sucrose (FIG. 7D) and 10% maltose (FIG. 7F) also preserved potency of RNA-SEAP, as measured by SEAP expression, after 24 hours storage at 42 degrees Celsius. Finally, at 42 degrees Celsius, lyophilized lipid carrier+RNA-SEAP containing 5% mannitol (FIG. 7B) or 5% glucose (FIG. 7E) resulted in a noticeable decrease in the dose-dependent expression profile of SEAP relative to their corresponding freshly prepared liquid formulations. For comparison, NLC was prepared with RNA-SEAP in 10% sucrose (FIG. 7G).

Figure 8:
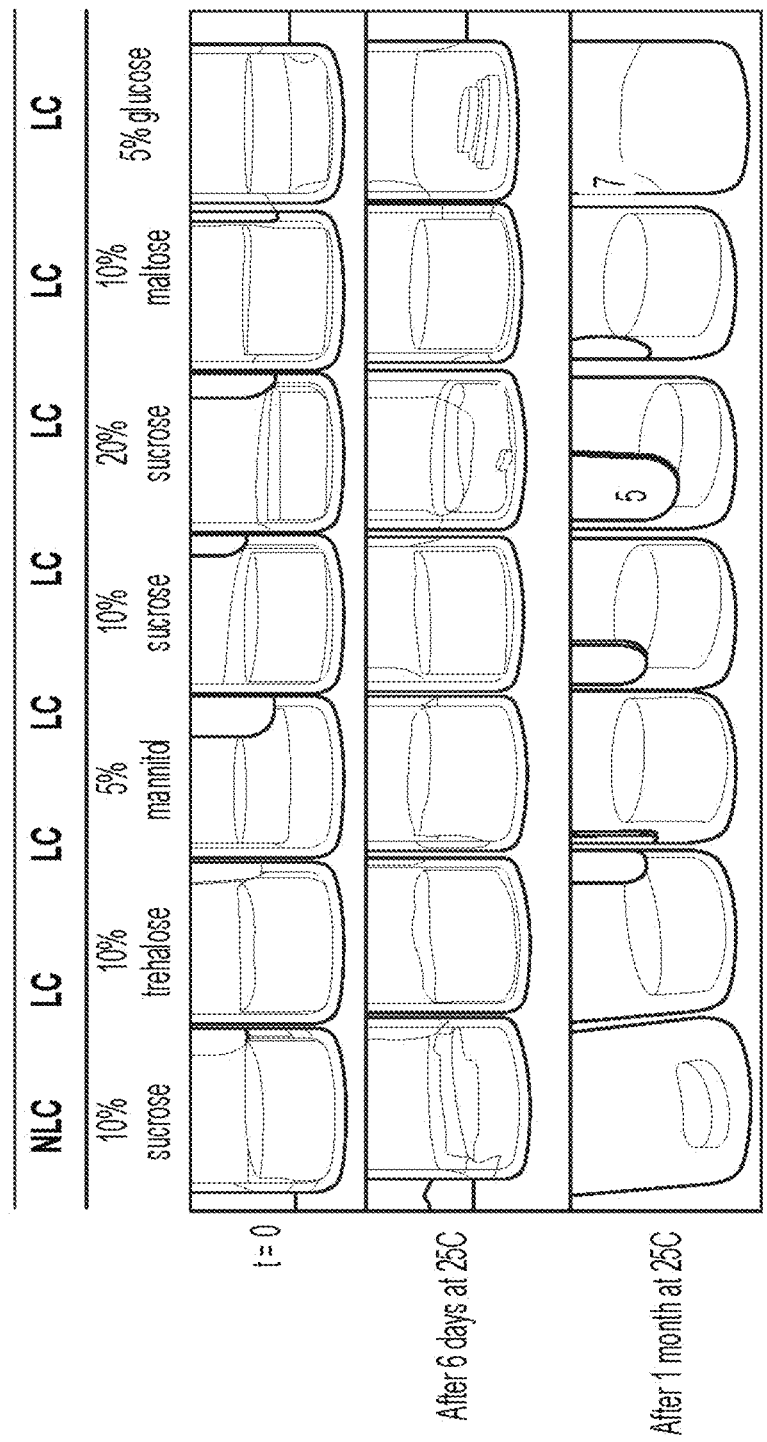
FIG. 8 illustrates the appearance of lipid carrier+RNA-SEAP cakes at various time points (time=0 hours, after 6 days at 25 degrees Celsius and after 1 month at 25 degrees Celsius) in the indicated sugar composition after lyophilization cycle #1.

Appearance of Lipid Carrier+RNA-SEAP Cakes after Lyophilization Cycle #1:

FIG. 8 and FIG. 9 show the appearance of lipid carrier+RNA-SEAP cakes in the indicated sugar composition at various time points after cycle #1. All lyophilized cakes showed good integrity at time=0 hr after cycle #1. FIG. 8 illustrates the appearance of lipid carrier+RNA-SEAP cakes at various time points (time=0 hr, after 6 days at 25 degrees Celsius and after 1 month at 25 degrees Celsius) in the indicated sugar composition after lyophilization cycle #1. FIG. 8 shows that the integrity of lipid carrier+RNA-SEAP in 5% glucose was significantly compromised after 6 days at 25 degrees Celsius and 1 month at 25 degrees Celsius. Integrity of NLC+RNA-SEAP in 10% sucrose was partially compromised after 6 days at 25 degrees Celsius and significantly compromised after 1 month at 25 degrees Celsius. Integrity of all other formulations was preserved after 1 month at 25 degrees Celsius.

FIG. 9 illustrates the appearance of lipid carrier+RNA-SEAP cakes at various time points (time=0 hr, after 24 days at 42 degrees Celsius and after 3 days at 42 degrees Celsius and after 1 month at 42 degrees Celsius) in the indicated sugar composition after lyophilization cycle #1. FIG. 8 shows that all sucrose and glucose containing formulations progressively shrank after 24 hours, 3 days and 1 month storage at 42 degrees Celsius. Integrity of all other formulations was preserved after 1 month at 42 degrees Celsius.

Example 7: Characterization Data after Cycle #3

Figure 10A:
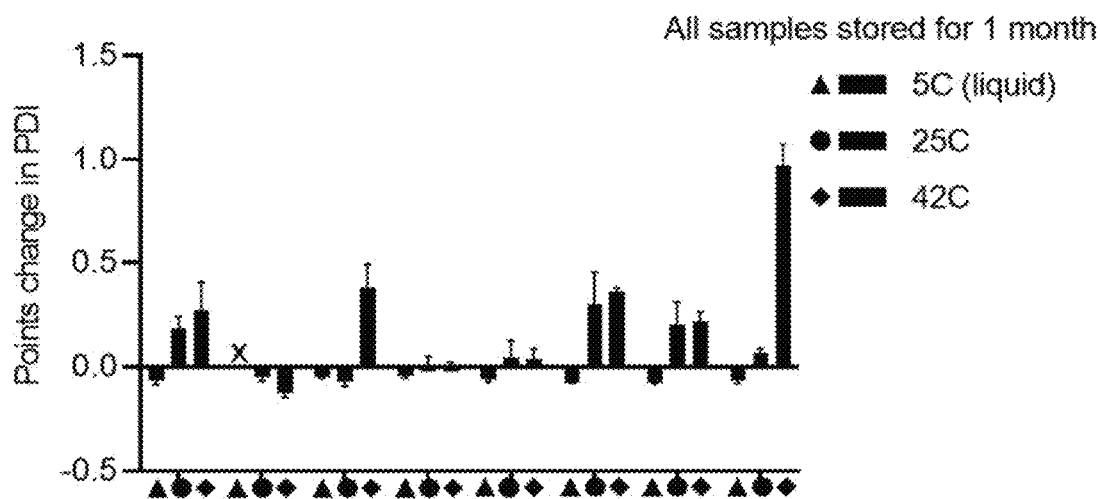
FIGS. 10A-10B illustrate the particle size of reconstituted cakes one day after storage in the indicated sugar composition after lyophilization cycle #3.
Figure 10B:
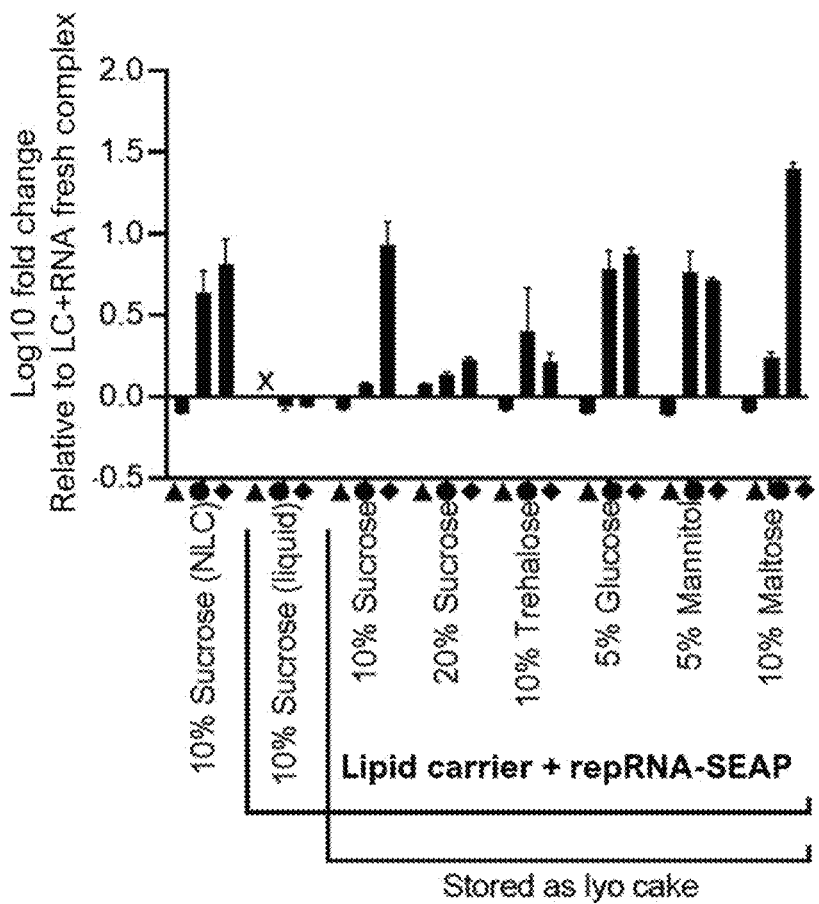

Particle Size after Lyophilization Cycle #3:

The particle size of reconstituted cakes one day after storage at 25 degrees Celsius or 42 degrees Celsius in the indicated sugar composition after lyophilization cycle #3 was measured as in FIGS. 10A-10B. FIGS. 10A-10B illustrate the particle size of reconstituted cakes one day after storage in the indicated sugar composition after lyophilization cycle #3. FIG. 10A shows the points change in PDI of reconstituted formulations in the indicated sugar composition. FIG. 10B shows the log 10 fold-change in particle size relative to lipid carrier+RNA fresh complex.

Mean size and size distribution values are shown in Table 12. All lyophilized formulations stored at 25 degrees Celsius or 42 degrees Celsius for one month resulted in an increase in complex size after reconstitution. Lipid carrier+RNA-SEAP prepared in 20% sucrose resulted in the smallest fold-change in particle size and minimal change in PDI relative to the liquid formulation stored at 5 degrees Celsius for one month as shown in FIGS. 10A-10B.

TABLE 12

Mean z-average diameter and mean PDI after lyophilization cycle #3.

| | 1 month stored at: | | |
|---|---|---|---|
| | 5 degrees Celsius (liquid) | 25 degrees Celsius (lyo) | 42 degrees Celsius (lyo) |
| Mean Z-average diameter [nm] | | | |
| 10% Sucrose (liquid) | x | 81.6 | 82.5 |
| 10% Sucrose | 79.3 | 112.4 | 830.7 |
| 20% Sucrose | 112.6 | 129.4 | 159.0 |
| 10% Trehalose | 77.6 | 270.7 | 153.7 |
| 5% Glucose | 75.0 | 583.6 | 711.9 |
| 5% Mannitol | 73.3 | 559.0 | 488.0 |
| 10% Maltose | 76.5 | 164.1 | 2370.3 |
| 10% Sucrose (NLC) | 74.8 | 423.8 | 634.9 |
| Fresh complex in 10% sucrose (t = 0) | | 94.1 | |
| Mean PDI | | | |
| 10% Sucrose (liquid) | x | 0.215 | 0.142 |
| 10% Sucrose | 0.220 | 0.197 | 0.648 |
| 20% Sucrose | 0.225 | 0.278 | 0.277 |
| 10% Trehalose | 0.204 | 0.312 | 0.305 |
| 5% Glucose | 0.193 | 0.564 | 0.625 |
| 5% Mannitol | 0.189 | 0.468 | 0.483 |
| 10% Maltose | 0.202 | 0.330 | 1.238 |
| 10% Sucrose (NLC) | 0.202 | 0.452 | 0.540 |
| Fresh complex in 10% sucrose (t = 0) | | 0.268 | |

Figure 11:
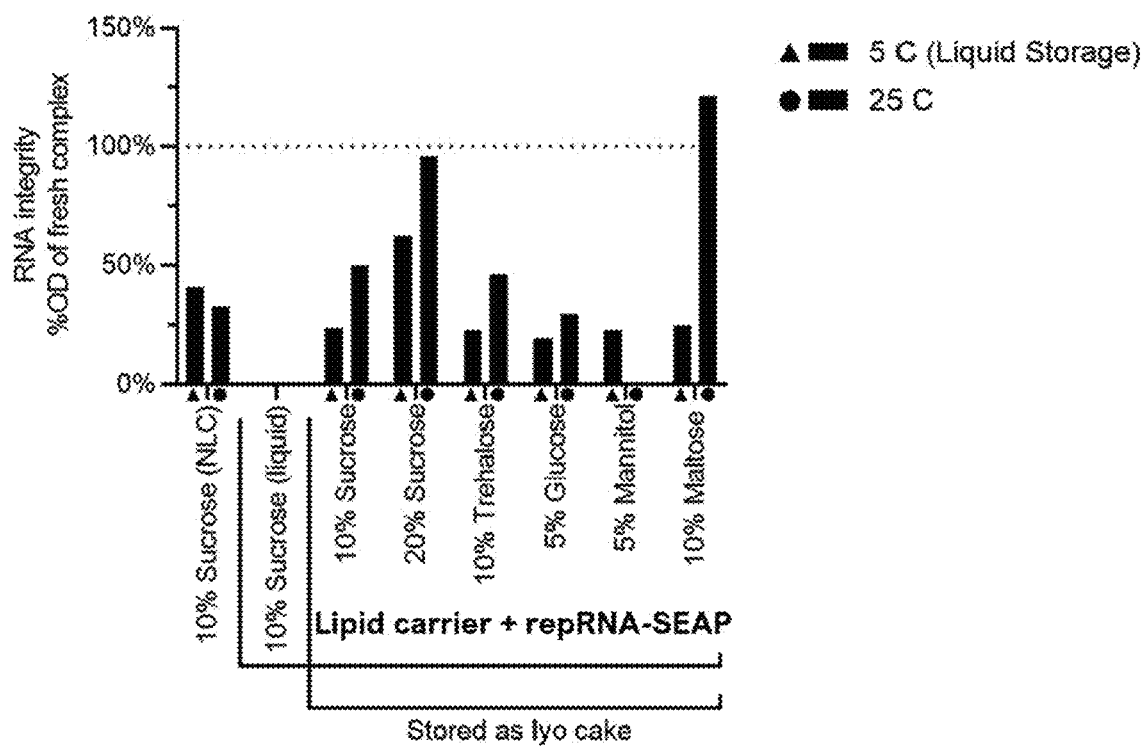
FIG. 11 illustrates the RNA integrity by agarose gel electrophoresis in the indicated sugar composition after lyophilization cycle #3.

RNA Integrity by Agarose Gel Electrophoresis after Lyophilization Cycle 93:

The RNA integrity by agarose gel electrophoresis in the indicated sugar composition after lyophilization cycle #3 is illustrated in FIG. 11. Both liquid and lyophilized formulations were stored for one month at 25 degrees Celsius and 42 degrees Celsius. FIG. 11 shows the % optical density (OD) of bands normalized to RNA-SEAP extracted from freshly prepared lipid carrier+RNA-SEAP in 10% sucrose. All samples, liquid or lyophilized, stored for 1 month at 42 degrees Celsius showed no detectable RNA band indicating complete degradation of RNA-SEAP. Except for NLC+RNA-SEAP in 10% sucrose and lipid carrier+RNA-SEAP in 5% mannitol, all lyophilized lipid carrier+RNA-SEAP formulations protected RNA-SEAP better at 25 degrees Celsius for 1 month than lipid carrier+RNA-SEAP stored in liquid form at 5 degrees Celsius for 1 month. Lipid carrier+RNA-SEAP in 10% sucrose stored as a liquid at 25 degrees Celsius for 1 month was completely. In comparison, when stored at 25 degrees Celsius in lyophilized form RNA-SEAP was at 50% OD relative to fresh complex and 23% OD when stored at 5 degrees Celsius in liquid form. lipid carrier+RNA-SEAP formulated in 20% sucrose or 10% maltose significantly preserved RNA-SEAP after 1 month storage at 25 degrees Celsius.

Figure 12:
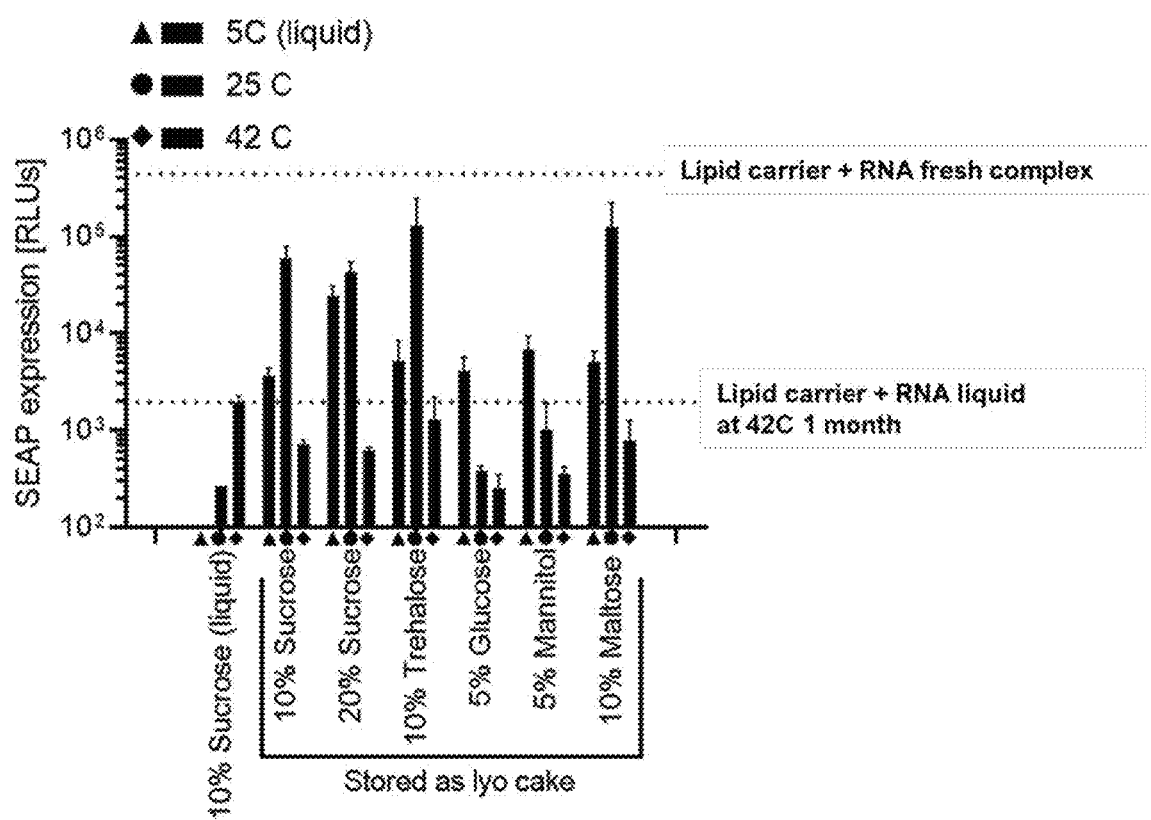
FIG. 12 illustrates the SEAP expression in BHK21 cells in the indicated sugar composition after lyophilization cycle #3.

SEAP Expression in BHK21 Cells after Lyophilization Cycle #3:

The SEAP expression in BHK21 cells in the indicated sugar composition after lyophilization cycle #3 is illustrated in FIG. 12. Mean SEAP expression levels shown for a single RNA transfection dose of 12.5 ng/well. For comparison, cells were transfected with freshly prepared lipid carrier+RNA-SEAP in 10% sucrose (upper dotted line), as shown in FIG. 12. Cells transfected with liquid formulation of lipid carrier+RNA-SEAP in 10% sucrose stored at 42 degrees Celsius for 1 month served as a comparison for measuring the effect of degraded RNA on in vitro protein expression (lower dotted line). Expression from all lyophilized samples stored at 42 degrees Celsius for 1 month was at or below the expression level of lipid carrier+RNA-SEAP in 10% sucrose stored in liquid form for 1 month at 42 degrees Celsius. Lyophilized lipid carrier+RNA-SEAP complexes in 10% sucrose, 20% sucrose, 10% trehalose and 10% maltose stored for 1 month at 25 degrees Celsius resulted in higher SEAP expression than the same compositions stored for 1 month in liquid form at 5 degrees Celsius.

Example 8: Immune Response in Macrophages

Various formulations of lipid carrier and repRNA were prepared and analyzed to assay innate immune response of the lipid carrier in macrophages. Protein expression and stimulation of TNF production in THP-1 macrophages was studied.

Initially, the THP-1 monocytes were differentiated into macrophages using phorbol 12-myristate 13-acetate (PMA). The cells were then transfected with various formulations with Nano Luciferase encoding replicon RNA (SEQ ID NO: 2). The cell culture media was then assessed for NanoLuc and TNF expression.

The formulations and their characteristics such as particle size and PDI that were used in this assay are described in Table 13. The concentration of repRNA encoding NanoLuc was 909 ng/ul and maintained at −80 degrees Celsius. MIGLYOL® 812 N, a triglyceride ester of saturated coconut/palm-kernel oil derived caprylic and capric fatty acids and plant derived glycerol was used in this assay.

TABLE 13

Formulations.

| Formulation | Particle size [diameter, nm] | PDI | Iron [mg Fe/ml] | Aluminum [mg Al/ml] | DOTAP [mg/ml] | Squalene [mg/ml] | MIGLYOL [mg/ml] | Solanesol [mg/ml] |
|---|---|---|---|---|---|---|---|---|
| Fe-lipid carrier | 59.3 | 0.23 | 0.19 | n/a | 27.9 | 39.4 | n/a | n/a |
| High Fe-lipid carrier | 57.5 | 0.24 | 0.85 | n/a | 29.1 | 40.5 | n/a | n/a |
| Fe-lipid carrier MIGLYOL | 48.7 | 0.2 | 0.18 | n/a | 28.3 | n/a | not measured | n/a |
| High Fe-lipid carrier MIGLYOL | 62.6 | 0.28 | 0.94 | n/a | 27.7 | n/a | not measured | n/a |
| Alum-lipid carrier | 64.5 | 0.25 | n/a | 0.88 | 27.4 | 41.2 | n/a | n/a |
| Fe-lipid carrier solanesol (SLN) | 86.1 | 0.26 | 0.16 | n/a | 26.2 | n/a | n/a | 36 |
| NLC | 50 | 0.26 | n/a | n/a | 26.7 | 34.1 | n/a | n/a |
| CNE | 105.4 | 0.06 | n/a | n/a | 4.4 | 47.4 | n/a | n/a |
| lipid carrier (w/o IO) | 54.2 | 0.22 | n/a | n/a | 19.3 | 32.6 | n/a | n/a |

Fe-lipid carrier formulation (prepared at 100 ml scale): Fe-lipid carrier formulation comprise 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml 12 nm oleic acid-coated iron oxide nanoparticles (Imagion Biosystems) and 10 mM sodium citrate dihydrate (Fisher Chemical). 1 ml of 20 mg Fe/ml 12 nm diameter oleic acid-coated iron oxide nanoparticles in chloroform (Imagion Biosystems, lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.25 polydispersity index (PDI). The microfluidized formulation was terminally filtered with a 200 nm pore-size polyethersulfone (PES) filter and stored at 2-8 degrees Celsius. Iron concentration was determined by ICP-OES. DOTAP and Squalene concentration were measured by RP-HPLC.

High Fe-lipid carrier formulation (prepared at 100 ml scale): High Fe-lipid carrier formulation comprise 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 1 mg Fe/ml 15 nm oleic acid-coated iron oxide nanoparticles (Imagion Biosystems) and 10 mM sodium citrate dihydrate (Fisher Chemical). 5 ml of 20 mg Fe/ml 15 nm diameter oleic acid-coated iron oxide nanoparticles in chloroform (Imagion Biosystems, Lot #95-133) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2-8 degrees Celsius. Iron concentration was determined by ICP-OES. DOTAP and Squalene concentration were measured by RP-HPLC.

Fe-lipid carrier miglyol formulation (prepared at 100 ml scale): Fe-lipid carrier miglyol formulation comprise 37.5 mg/ml MIGLYOL® 812 N (IOI Oleo GmbH, Hamburg, Germany), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml 15 nm oleic acid-coated iron oxide nanoparticles (Imagion Biosystems) and 10 mM sodium citrate dihydrate (Fisher Chemical). 1 ml of 20 mg Fe/ml 15 nm diameter oleic acid-coated iron oxide nanoparticles in chloroform (Imagion Biosystems, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2-8 degrees Celsius. Iron concentration was determined by ICP-OES. DOTAP concentration was measured by RP-HPLC.

High Fe-lipid carrier miglyol formulation (prepared at 100 ml scale): High Fe-lipid carrier miglyol formulation comprise 37.5 mg/ml MIGLYOL® 812 N (IOI Oleo GmbH), 37 mg/ml SPAN® 60 (Millipore Sigma), 37 mg/ml TWEEN® 80 (Fisher Chemical), 30 mg/ml DOTAP chloride (LIPOID), 1 mg/ml 15 nm oleic acid-coated iron oxide nanoparticles (Imagion Biosystems) and 10 mM sodium citrate dihydrate (Fisher Chemical). 5 ml of 20 mg Fe/ml 15 nm diameter oleic acid-coated iron oxide nanoparticles in chloroform (Imagion Biosystems, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN® 60, and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2-8 degrees Celsius. Iron concentration was determined by ICP-OES. DOTAP concentration was measured by RP-HPLC.

Alum-lipid carrier formulation (prepared at 100 ml scale): Alum-lipid carrier formulation comprise 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 1 mg Al/ml TOPO-coated Alhydrogel® (aluminum oxyhydroxide) particles (Croda) and 10 mM sodium citrate. 10 ml of Alhydrogel was washed three times in methanol by centrifuging at 1000 rpm for 20 minutes. After the third wash, Alhydrogel was dispersed in 10 ml methanol and to this dispersion was added 1 ml of 250 mg/ml trioctylphosphine oxide (TOPO) and incubated overnight in a 37 degrees Celsius orbital shaker. Excess TOPO was removed by additional methanol washes and then dispersed in 11 ml methanol. Methanol was allowed to evaporate overnight in the fume hood leaving behind a dry layer of TOPO-Alhydrogel. To this dry TOPO-Alhydrogel layer, 3.75 grams squalene, 3.7 grams SPAN® 60, and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2-8 degrees Celsius. Aluminum concentration was determined by ICP-OES. DOTAP and Squalene concentration were measured by RP-HPLC.

Fe-lipid carrier solanesol formulation (prepared at 100 ml scale): Fe-lipid carrier solanesol formulation comprise 37.5 mg/ml Solanesol (Cayman chemicals), 37 mg/ml SPAN® 60 (Millipore Sigma), 37 mg/ml TWEEN® 80 (Fisher Chemical), 30 mg/ml DOTAP chloride (LIPOID), 0.2 mg Fe/ml oleic acid-coated iron oxide nanoparticles (Imagion Biosystems) and 10 mM sodium citrate. 1 ml of 20 mg Fe/ml 15 nm diameter oleic acid-coated iron oxide nanoparticles in chloroform (Imagion Biosystems, Lot #95-133) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams solanesol, 3.7 grams SPAN® 60, and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber. The microfluidized formulation was terminally filtered with a 200 nm pore-size polyethersulfone (PES) filter and stored at 2-8 degrees Celsius. Iron concentration was determined by ICP-OES. DOTAP and solanesol concentration were measured by RP-HPLC.

NLC formulation (prepared at 100 ml scale): NLC formulation comprise 37.5 mg/ml squalene (SEPPIC), 37 mg/ml SPAN® 60 (Millipore Sigma), 37 mg/ml TWEEN® 80 (Fisher Chemical), 30 mg/ml DOTAP chloride (LIPOID), 2.4 mg/ml Dynasan 114 (101 Oleo GmbH) and 10 mM sodium citrate. To a 200 ml beaker 3.75 grams squalene, 3.7 grams SPAN® 60, 0.24 grams Dynasan 114 and 3 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 92 ml of the aqueous phase was transferred to a separate glass bottle and heated to 65 degrees Celsius for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2-8 degrees Celsius. DOTAP and Squalene concentration were measured by RP-HPLC.

CNE formulation (prepared at 100 ml scale): CNE formulation comprise 43 mg/ml squalene (SEPPIC), 5 mg/ml SPAN® 85 (Millipore Sigma), 5 mg/ml TWEEN® 80 (Fisher Chemical), 4 mg/ml DOTAP chloride (LIPOID) and 10 mM sodium citrate. To a 200 ml beaker 4.3 grams squalene, 0.5 grams SPAN® 85, and 0.4 grams DOTAP were added to produce the oil phase. The oil phase was sonicated for 45 minutes in a 65 degrees Celsius water bath. Separately, the aqueous phase was prepared by dissolving 2.6 grams TWEEN® 80 in 500 ml of 10 mM sodium citrate buffer prepared in nuclease free water. 95 ml of the aqueous phase was transferred to a separate glass bottle and heated to 65 degrees Celsius for 30 minutes. The oil phase was mixed with the 95 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 100±10 nm with a 0.05-0.1 polydispersity index (PDI). The microfluidized formulation was terminally filtered with a 200 nm pore-size polyethersulfone (PES) filter and stored at 2-8 degrees Celsius. DOTAP and Squalene concentration were measured by RP-HPLC.

The treatment groups were prepared. Eight of those groups were NanoLuc repRNA groups, with 600 ng dose per well was prepared using the Fe-lipid carrier, High Fe-lipid carrier, Fe-lipid carrier miglyol, High Fe-lipid carrier miglyol, Alum-lipid carrier, Fe-lipid carrier solanesol (SLN), NLC, and CNE formulations. The untreated group did not have NanoLuc.

The various formulations were prepared by diluting NanoLuc repRNA to 8 ng/μL in 2.2 mL of RNAse-free water. The lipid carrier formulations and RNA master mix was complexed by adding 250 μL of each diluted formulation with 250 μL of diluted RNA, and mixed by pipetting up and down.

Cell transfections were carried out by seeding 7×10$^5$ THP-1s per well in a 24 well plate. 80 μM of PMA per well was added and incubated at 37 degrees Celsius. The next day, the PMA-containing media was removed and replaced with cRPMI for an hour before transfection. The samples were then serially diluted in Opti-MEM™ to make a 10-point 1.5-fold dilution series starting at 0.45 ng/μL. The culture media was then removed from the plates by pipetting. 450 μL of Opti-MEM™ and 150 μL of the complexed formulation was added to the plate in duplicate. The empty wells were given 450 μL of Opti-MEM™ only. After four hours, the samples were removed from the plate by pipetting and replaced with 500 μL of growth media. The plate was then incubated overnight at 37 degrees Celsius. The growth media was harvested the next day and stored at −80 degrees Celsius. Downstream assays were conducted.

The luciferase assay was performed by first diluting the Nano-Glo luciferase assay reagent 1:50 in buffer. 25 μL of supernatant was removed and mixed with 25 μL of Nano-Glo reagent in a 96-well plate. This was incubated at room temperature for 3 minutes. The luminescence was read.

ELISA assay was performed to evaluate the TNF-alpha protein level in the media using the Human TNF-alpha DuoSet ELISA by R&D Systems according to the manufacturer's protocol. The 96-well microplate was coated with anti-TNF capture antibody. The plate was blocked and then media samples were added directly without dilution. After addition of the biotinylated detection antibody, SA-HRP, and substrate, the absorbance was read at 450 nm on a SPECTRAMAX® i3 (Molecular Devices, LLC, San Jose CA, USA) plate reader.

All studies in this example were done in duplicates. Results from the duplicates are presented as first experiment and second experiment respectively.

Figure 13A:
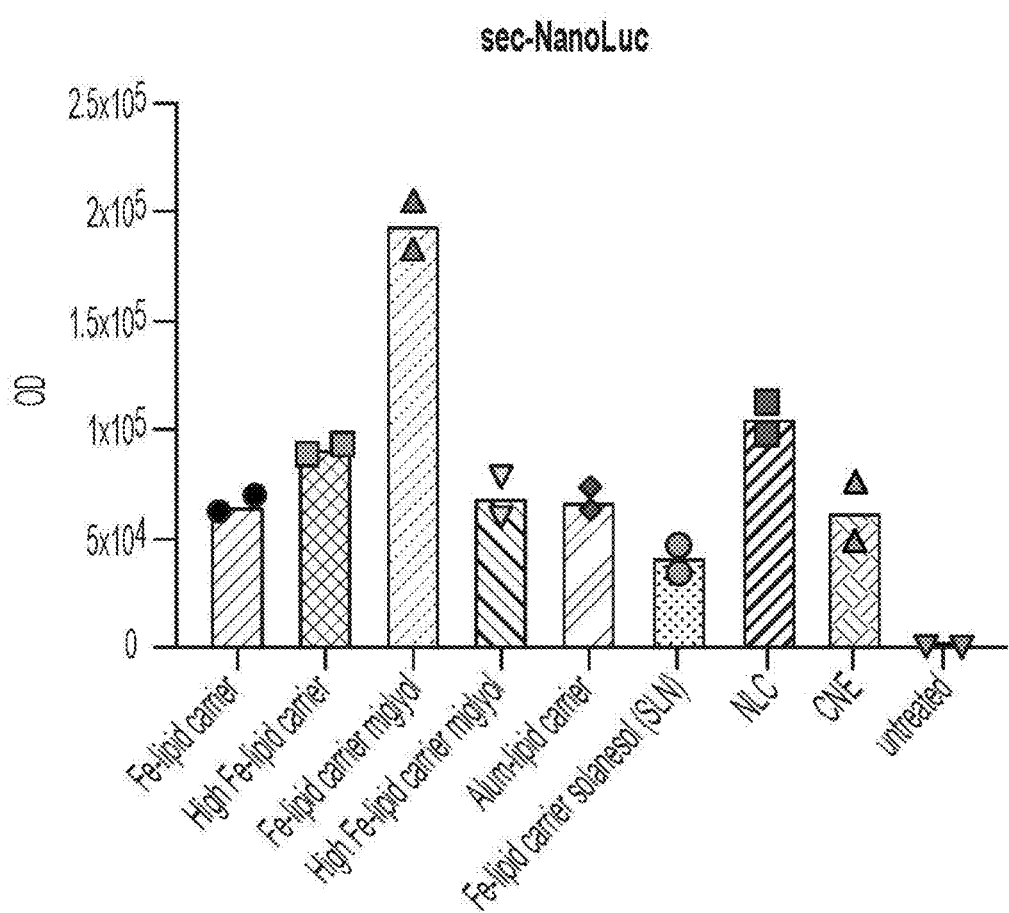
FIGS. 13A-13B show that miglyol-lipid carrier formulation induces enhanced repRNA protein production in macrophages.
Figure 13B:
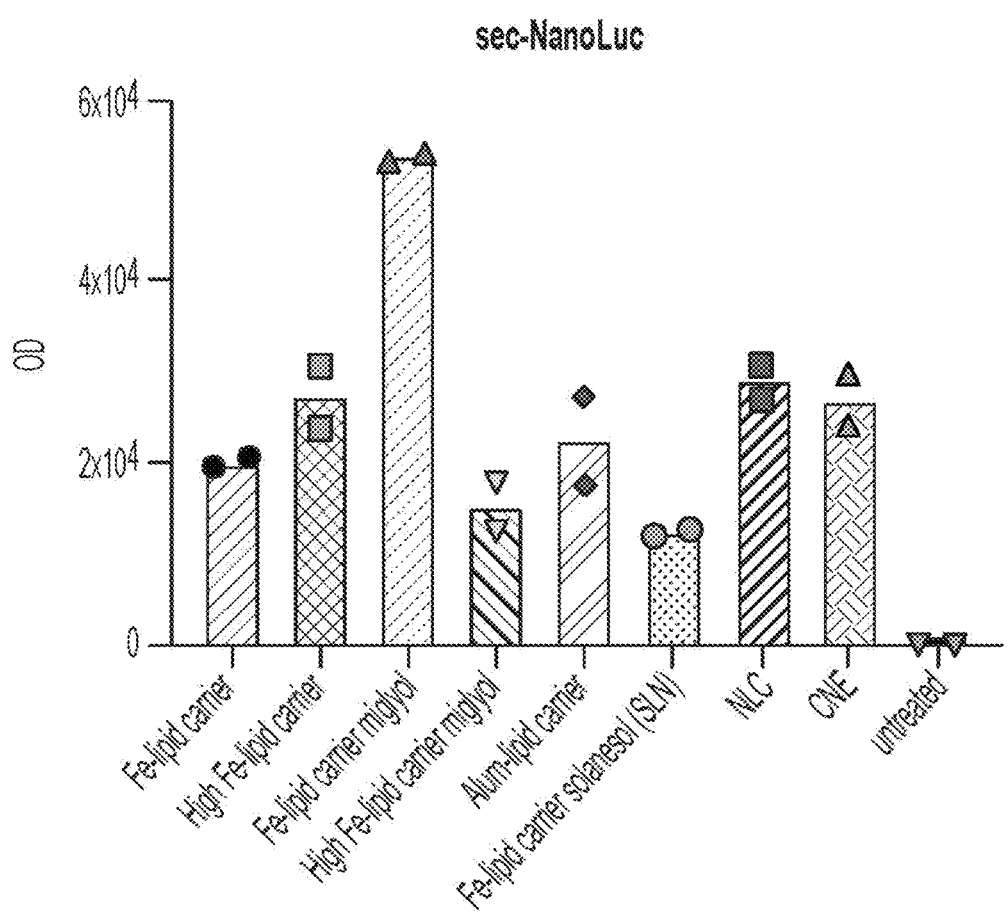
Figure 14A:
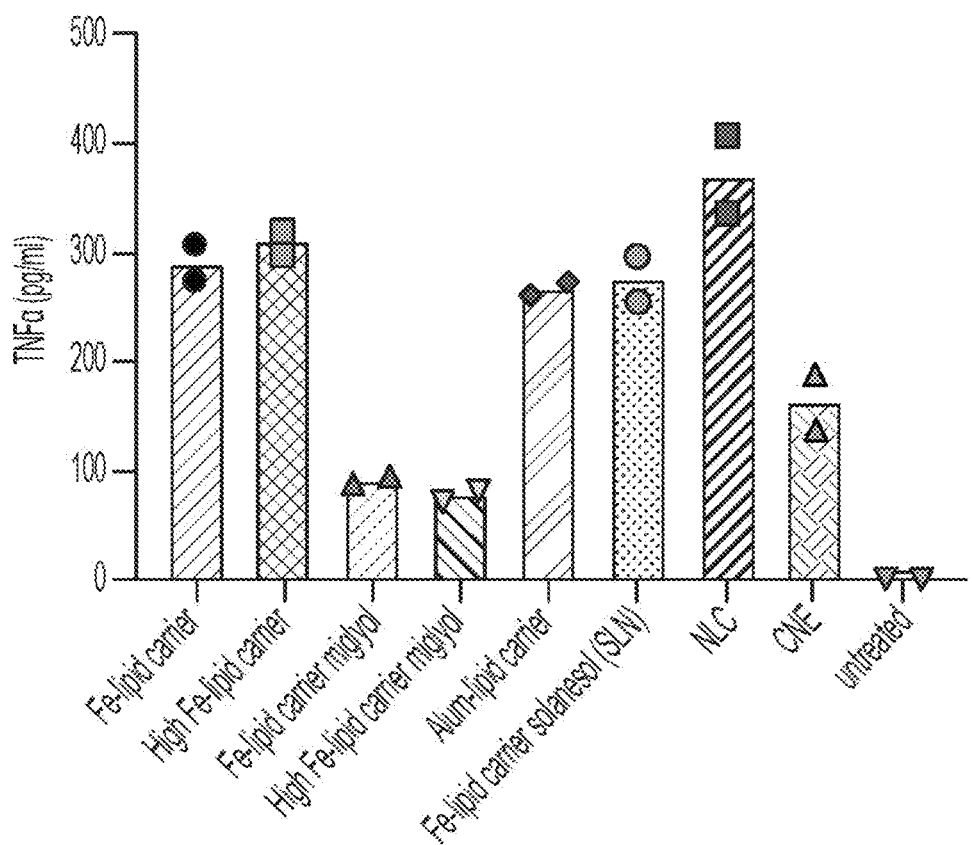
FIGS. 14A-14B show reduced TNF-alpha (α) production in macrophages with miglyol formulation.
Figure 14B:
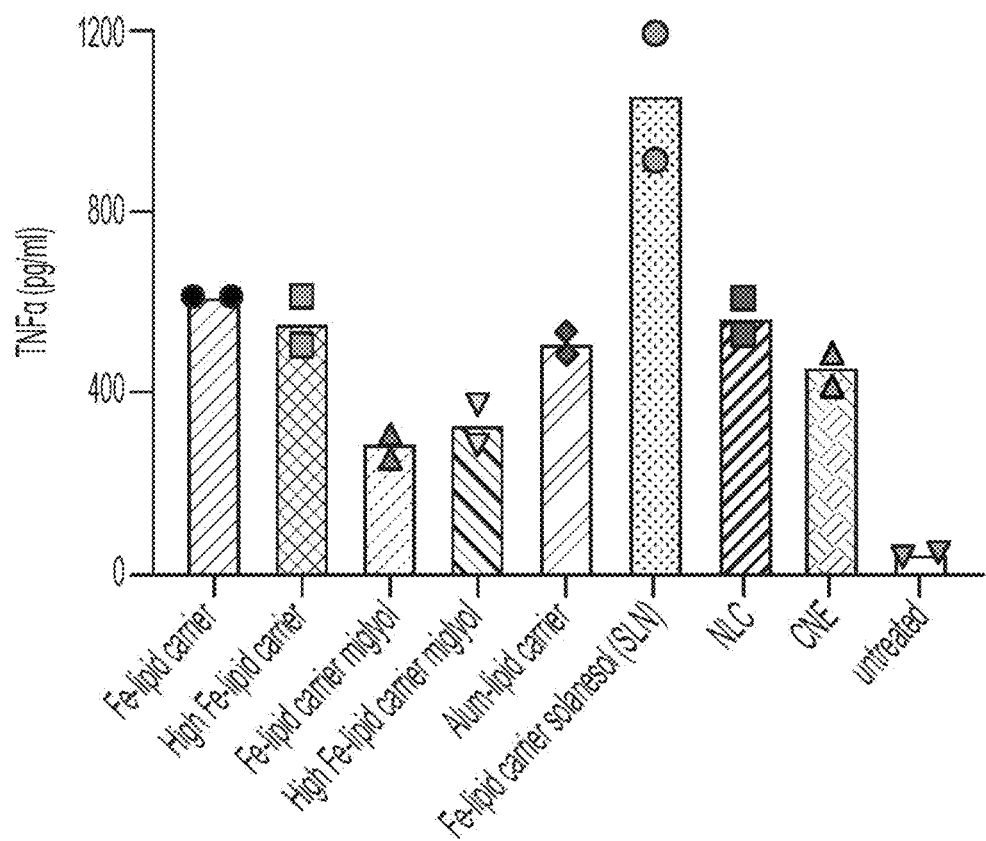

The assay demonstrates that the liquid formulation comprising of lipid carrier and Miglyol induced higher protein production off the replicon, as shown in the first assay in FIG. 13A and in the second assay in FIG. 13B. A reduced innate immune response was detected, as measured by TNF-alpha secretion and is shown in the first assay in FIG. 14A and in the second assay in FIG. 14B.

Figure 15A:
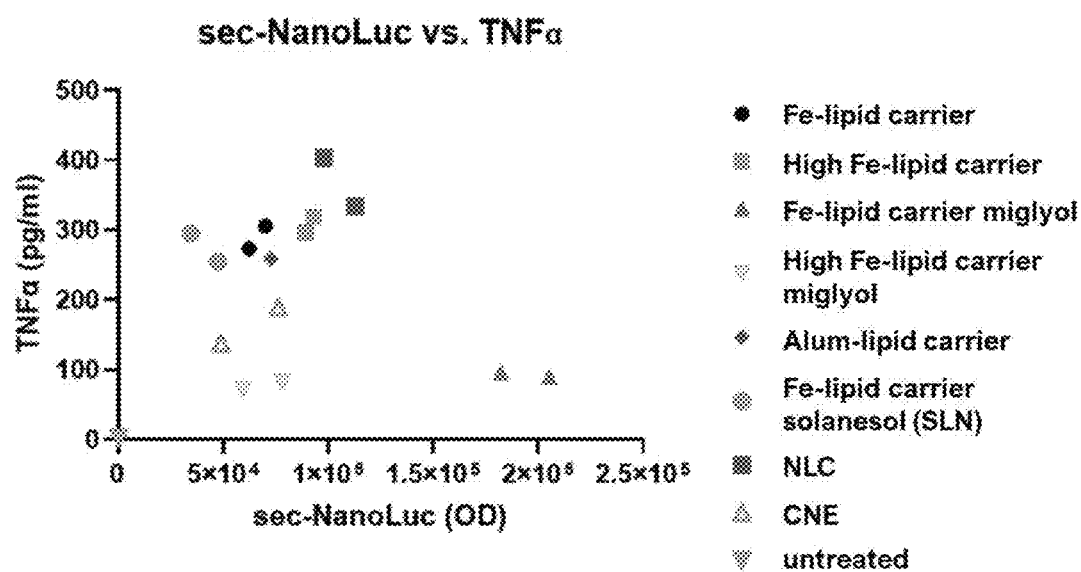
FIGS. 15A-15B show the correlation between enhanced protein production and low TNF-alpha production in macrophages with miglyol formulation.
Figure 15B:
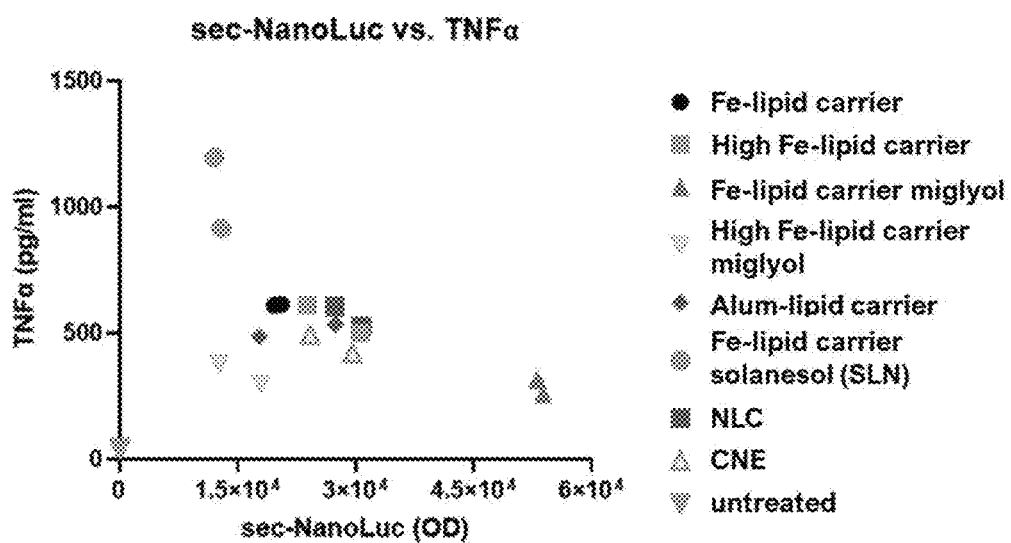

The correlation between enhanced protein production and low TNF-alpha stimulation was observed with Miglyol lipid carrier formulation, as shown in the first assay in FIG. 15A and in the second assay in FIG. 15B. The solanesol induced slightly lower protein production, but potentially higher TNF production, shown in the first assay in FIG. 15A and in the second assay in FIG. 15B.

Figure 16A:
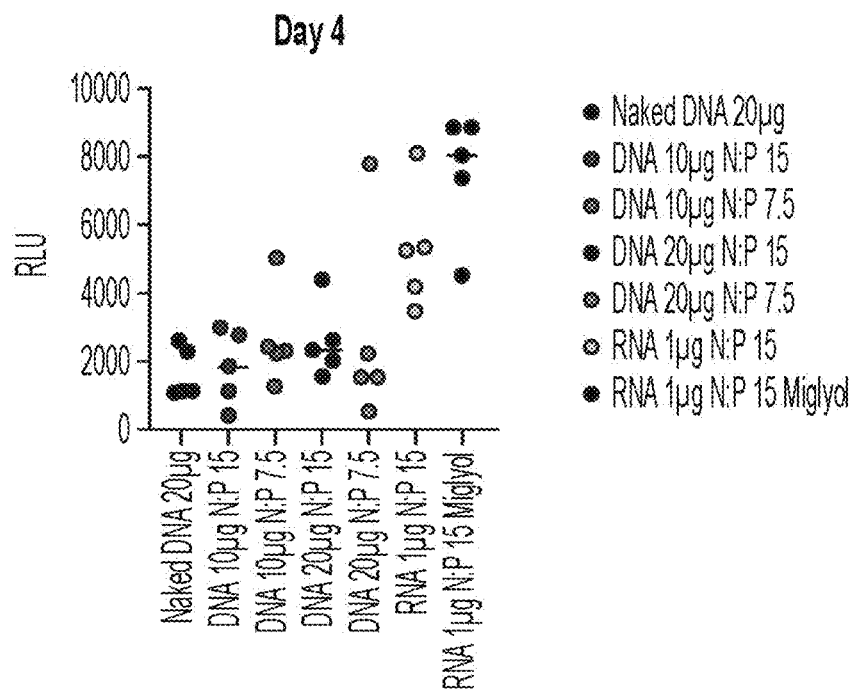
FIGS. 16A-16F illustrate the SEAP levels in BALB/c mice injected intramuscularly with varying iterations of lipid carrier-formulated DNA SEAP.
Figure 16B:
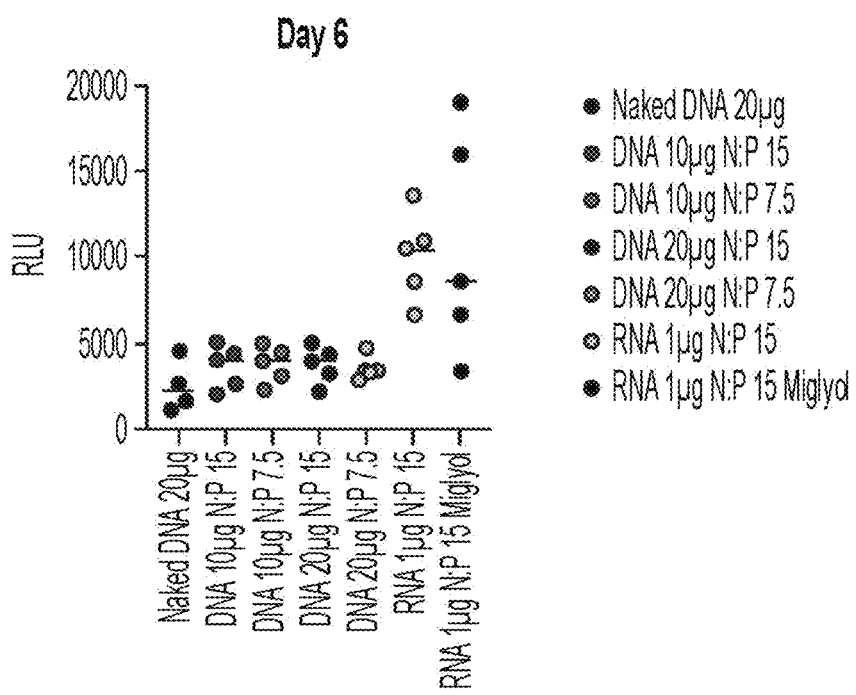
Figure 16C:
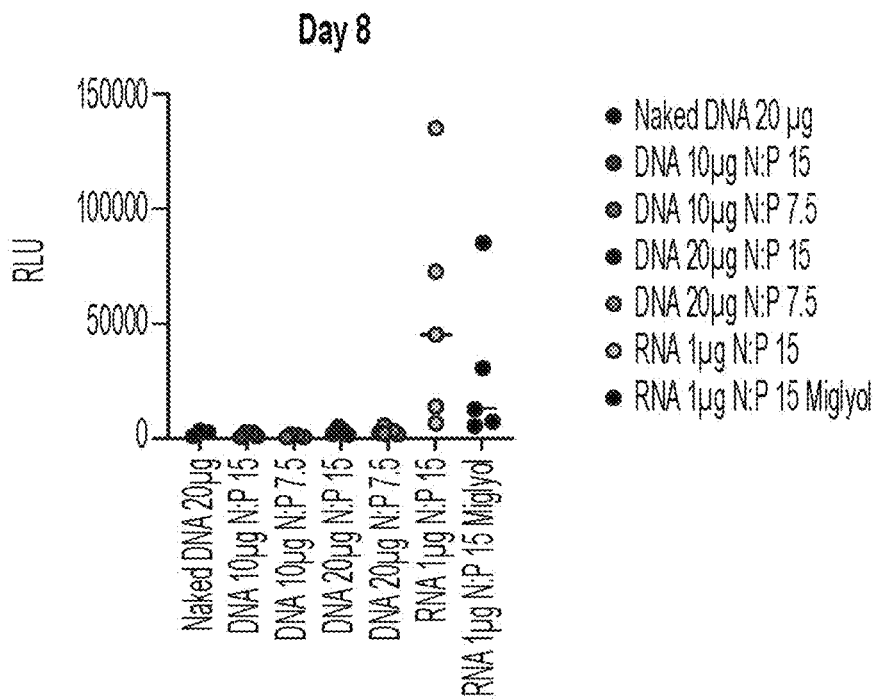
Figure 16D:
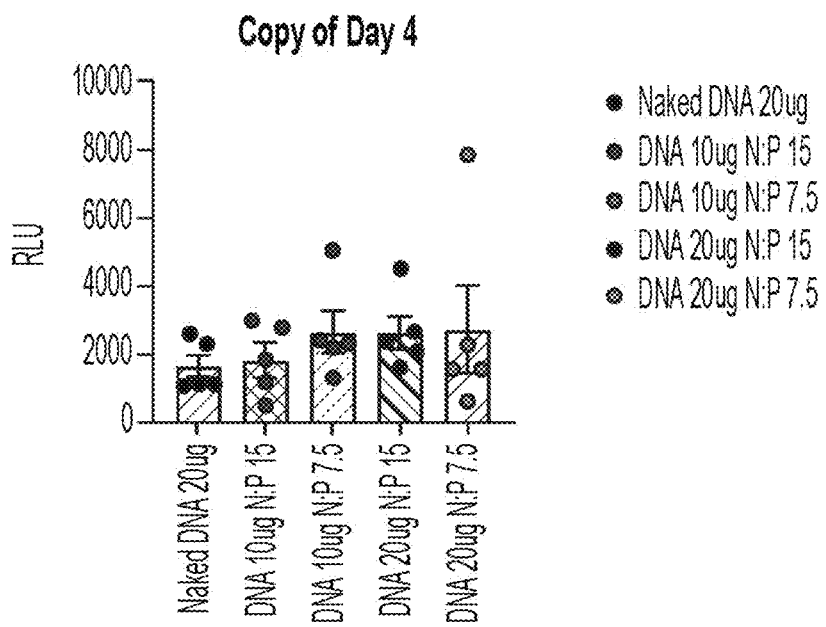
Figure 16E:
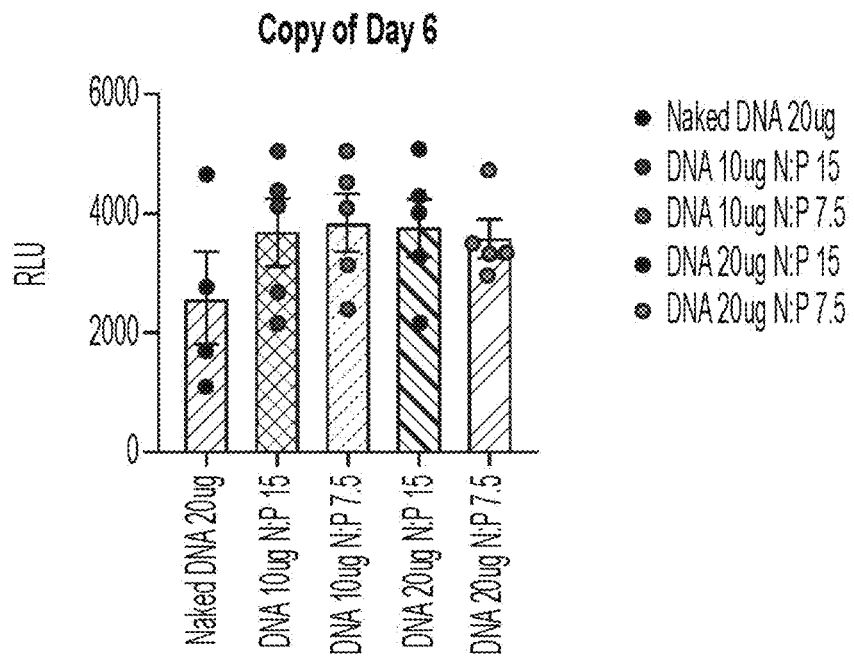
Figure 16F:
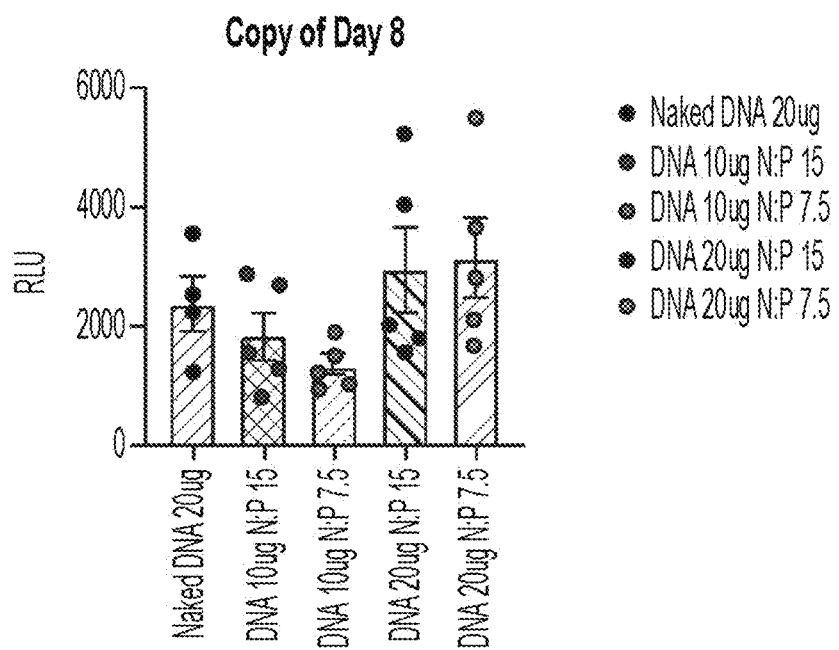

FIGS. 16A-16F illustrate the SEAP levels in BALB/c mice injected intramuscularly with varying iterations of lipid carrier-formulated DNA SEAP. FIG. 16A shows the Relative Luminescence Units (RLU) at Day 4. FIG. 16B shows the Relative Luminescence Units (RLU) at Day 6. FIG. 16C shows the Relative Luminescence Units (RLU) at Day 8. FIG. 16D is a copy of the Relative Luminescence Units (RLU) at Day 4. FIG. 16E is a copy of Relative Luminescence Units (RLU) at Day 6. FIG. 16F is a copy of the Relative Luminescence Units (RLU) at Day 8.

Figure 17:
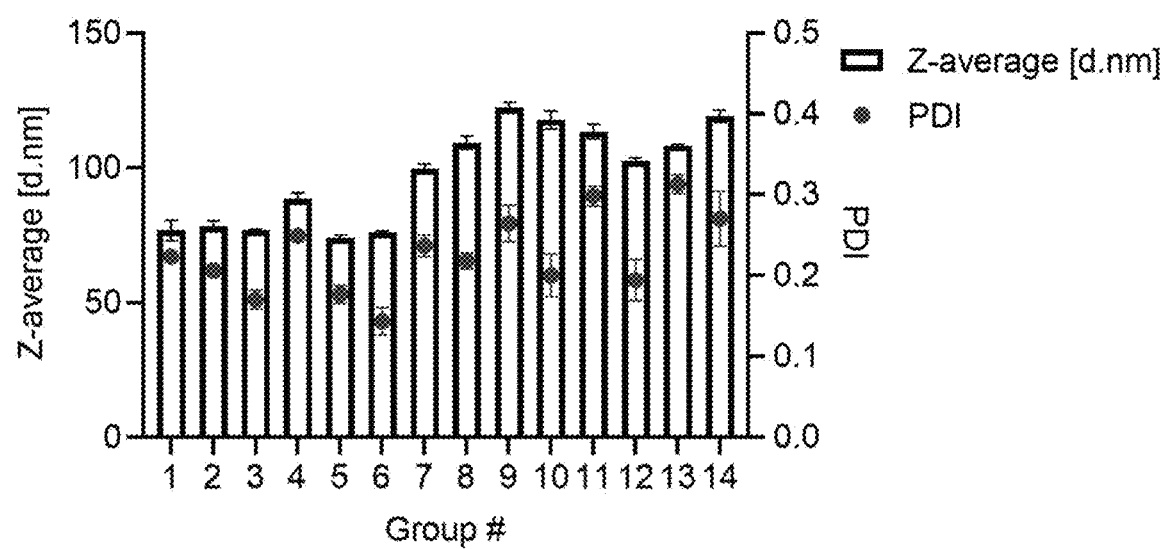
FIG. 17 is a bar chart with measurements of Z-average measurement and polydispersity index (PDI) on the Y-axis and group number on the X-axis for conditions 1 to 14.

FIG. 17 is a bar chart with measurements of Z-average measurement and polydispersity index (PDI) on the Y-axis and group number on the X-axis for conditions 1 to 14.

Figure 18A:
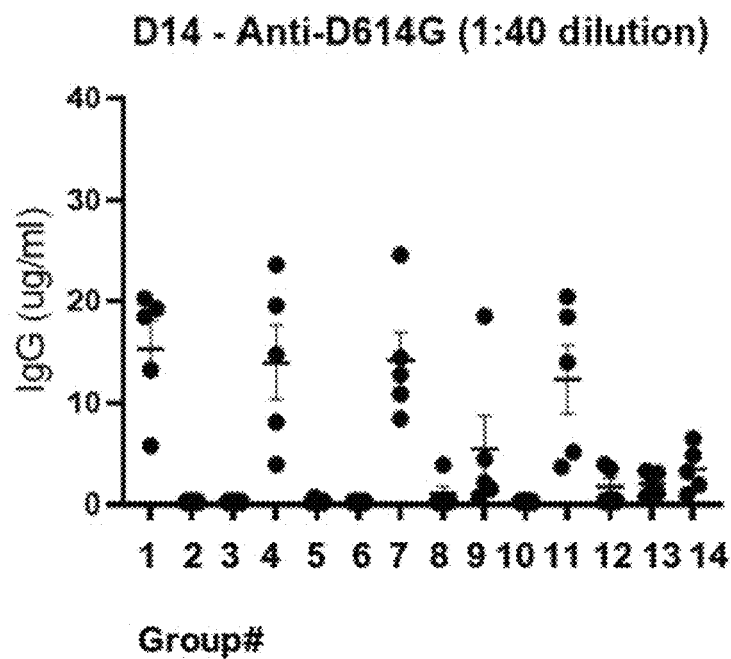
FIGS. 18A-18B show dot charts showing anti-D614G IgG levels for conditions 1 to 14.
Figure 18B:
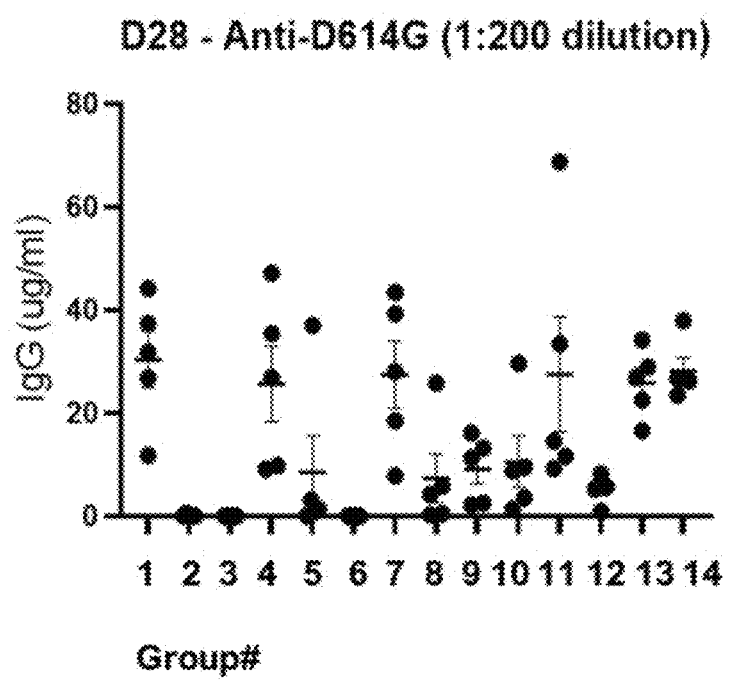

FIGS. 18A-18B are dot charts with IgG (μg/ml) on the Y-axis, group number on the X-axis for conditions 1 to 14, and recordings shown for measurements at day 14 anti-D614G (1:40 dilution) and day 28 anti-D614G (1:200 dilution), respectively.

Figure 19:
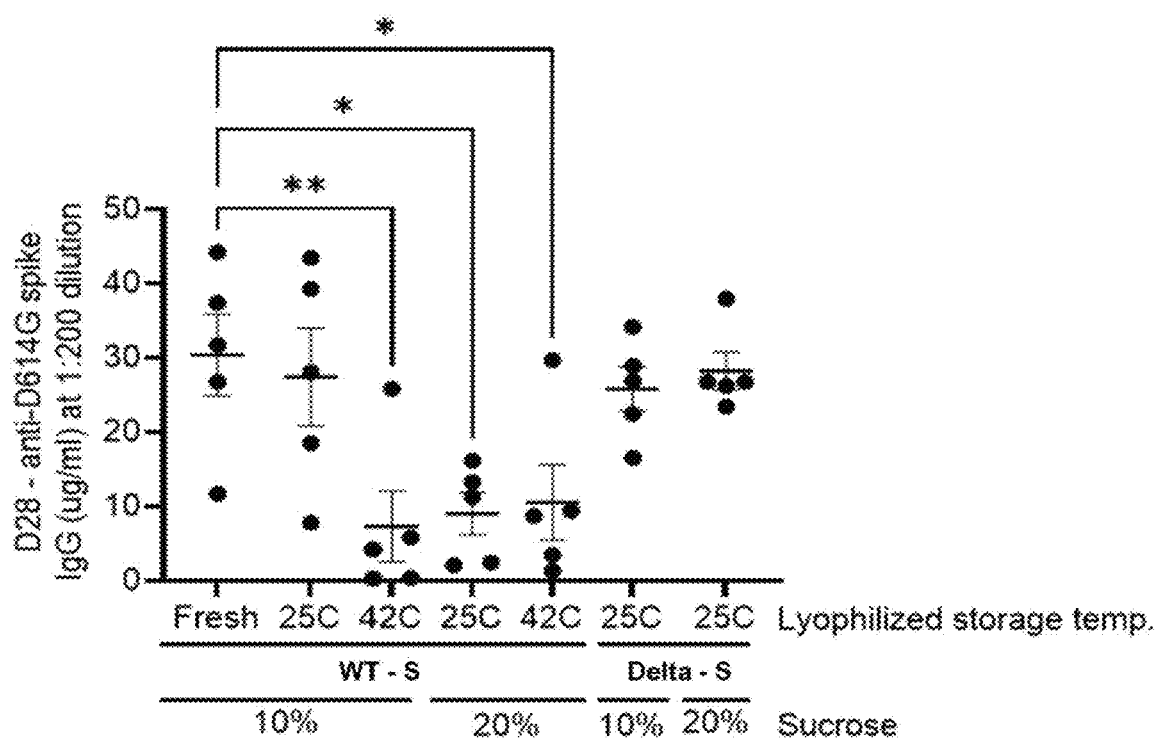
FIG. 19 shows a dot chart at day 28 with anti-D614G (1:200 dilution) IgG (μg/ml) measurements on the Y-axis and indications of storage conditions on the X-axis.

FIG. 19 shows a dot chart at day 28 with anti-D614G (1:200 dilution) IgG (μg/ml) measurements on the Y-axis and indications of storage conditions on the X-axis.

No other major differences between formulations were observed. This suggests that the formulation comprising of lipid carrier and miglyol (Fe-lipid carrier miglyol) could be a potential formulation in therapeutic applications, such as, but not limited to anti-viral therapy and cancer therapy. In such therapeutic applications, a high protein production and low immunostimluation are desired, such as, but not limited to the in vivo production of a therapeutic protein or antibody.

Example 9: DNA (SEAP) Bioactivity in Mice

This example studies the impact of an injected dose on bioactivity of lipid carrier and DNA (SEAP) in BALB/c mice. The kinetics, duration and magnitude were studied. Materials: DNA encoding SEAP (vendor: Aldevron; catalog no.: gWiz-SEAP, lot no.: 38611), 5 mg/mL at −20 degrees Celsius, repRNA encoding SEAP (SEQ ID NO: 1), 2217 μg/mL at −80 degrees Celsius and a lipid carrier formulation (30 mg DOTAP/ml) at 4 degrees Celsius was used in this example. C57BL/6 mice were inoculated as described in the treatment groups listed in Table 14, after which SEAP levels were measured in serum.

TABLE 14

Treatment groups.

| Group | n | Formulation | DNA/RNA-SEAP | RNA dose [μg] | DNA dose [μg] | N:P | Injection Volume [μL] |
|---|---|---|---|---|---|---|---|
| 1 | 5 | Naked | DNA-SEAP | | 20 | n/a | 50 |
| 2 | 5 | Lipid carrier | DNA-SEAP | | 10 | 15 | 50 |
| 3 | 5 | Lipid carrier | DNA-SEAP | | 10 | 7.5 | |
| 4 | 5 | Lipid carrier | DNA-SEAP | | 20 | 15 | |
| 5 | 5 | Lipid carrier | DNA-SEAP | | 20 | 7.5 | |
| 6 | 5 | Lipid carrier | RNA-SEAP | 1 | | 15 | 50 |
| 7 | 5 | MIGLYOL + lipid carrier | RNA-SEAP | 1 | | 15 | 50 |

Seven different formulations were prepared and administered intramuscularly across the seven treatment groups (Groups 1-7). DNA-SEAP or RNA-SEAP was diluted according to the volumes set forth in Table 15 to prepare the formulations for Groups 1-7.

TABLE 15

Preparation of formulation: Dilution of RNA/DNA.

| Group | DNA- or RNA-SEAP | DNA or RNA [μL] | 40% sucrose [μL] | water [μL] | Total [μL] |
|---|---|---|---|---|---|
| 1 | DNA-SEAP | 40.0 | 125.0 | 85.0 | 250.0 |
| 2 | DNA-SEAP | 20.0 | 0.0 | 230.0 | 250.0 |
| 3 | DNA-SEAP | 20.0 | 0.0 | 230.0 | 250.0 |
| 4 | DNA-SEAP | 40.0 | 125.0 | 85.0 | 250.0 |

TABLE 15-continued

Preparation of formulation: Dilution of RNA/DNA.

| Group | DNA- or RNA-SEAP | DNA or RNA [μL] | 40% sucrose [μL] | water [μL] | Total [μL] |
|---|---|---|---|---|---|
| 5 | DNA-SEAP | 40.0 | 0.0 | 210.0 | 250.0 |
| 6 | RNA-SEAP | 4.5 | 0.0 | 245.5 | 250.0 |
| 7 | RNA-SEAP | 4.5 | 0.0 | 245.5 | 250.0 |

The concentrations of diluted DNA or RNA prior to complexing with the lipid carrier was as follows (measured by NanoDrop spec): Groups 1, 4 and 5 contains about 820 μg/ml DNA; Groups 2 and 3 contained about 480 μg/ml DNA; and Groups 6 and 7 contained about 43 μg/ml RNA. Formulations for Groups 1-6 were diluted with 100 MM citrate as set forth in Table 16 below.

TABLE 16

Dilution of lipid carrier formulations.

| Group | Formulation | Lipid Carrier [μl] | 40% sucrose [μl] | 100 mM citrate [μl] | Water [μl] | Total [μl] |
|---|---|---|---|---|---|---|
| 1 | Naked | 0 | 0 | 30 | 270 | 300 |
| 2 | Lipid carrier | 120 | 150 | 30 | 0 | 300 |
| 3 | Lipid carrier | 60 | 150 | 30 | 60 | 300 |
| 4 | Lipid carrier | 240 | 0 | 30 | 30 | 300 |
| 5 | Lipid carrier | 120 | 150 | 30 | 0 | 300 |
| 6 | Lipid carrier | 12 | 150 | 30 | 108 | 300 |
| 7 | MIGLYOL + lipid carrier | 12 | 150 | 30 | 108 | 300 |

The above formulations were complexed by adding 250 μl diluted lipid carrier to 250 μl diluted DNA or RNA. The resulting complexed formulations were incubated on ice for at least 30 minutes. Table 17 sets forth the schedule for this assay.

TABLE 17

Schedule.

| Day | Procedure | Notes on Mice |
|---|---|---|
| 0 | All inoculations | None |
| 4 | Bleed | Group 4 had ruffled fur, one mouse emaciated (died during collection). Hydropaque placed in cage. |
| 6 | Bleed | None |
| 8 | Bleed | None |
| 11 | Bleed | None |
| 14 | Bleed | None |

Mice were bled at regular intervals and serum was prepared immediately and stored at −80 degrees Celsius until analyses for SEAP activity.

To evaluate SEAP levels in serum, all serum samples were thawed at the same time and SEAP detection was conducted. FIGS. 16A-16F illustrate the SEAP levels in BALB/c mice injected intramuscularly with varying iterations of lipid carrier-formulated DNA SEAP. Mice were bled at regular intervals, serum prepared and stored until analysis by SEAP assay. Data are displayed as a mean and SE (n=5 per group).

As can be seen from FIGS. 16A-16F, lipid carrier formulations aide target protein production over delivery of DNA alone, particularly after day 6 following injection. Additionally, this example shows that inclusion of miglyol enhances protein production from an RNA replicon over lipid carrier formulations lacking miglyol.

Example 10: Lipid Carrier without Inorganic Core Formulation

The lipid carrier without inorganic core formulation was prepared at 100 ml scale. The lipid carrier without inorganic core comprises 37.5 mg/ml squalene (SEPPIC), 37 mg/ml SPANR 60 (Millipore Sigma), 37 mg/ml TWEEN® 80 (Fisher Chemical), 30 mg/ml DOTAP chloride (LIPOID) and 10 mM sodium citrate. To a 200 ml beaker 3.75 grams squalene, 3.7 grams SPANR 60, and 3.0 grams DOTAP were added to produce the oil phase. The oil phase was sonicated for 45 minutes in a 65 degrees Celsius water bath. Separately, the aqueous phase was prepared by dissolving 19.5 grams TWEEN® 80 in 500 ml of 10 mM sodium citrate buffer prepared in nuclease free water. 96 ml of the aqueous phase was transferred to a separate glass bottle and heated to 65 degrees Celsius for 30 minutes. The oil phase was mixed with the 96 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H3Z-200 Im ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation without inorganic core formulation was terminally filtered with a 200 nm pore-size polyethersulfone (PES) filter and stored at 2-8 degrees Celsius. DOTAP and Squalene concentration were measured by RP-HPLC.

Example 11: Additional Nanoparticle Formulations

Additional nanoparticle formulations are produced according to the following tables (Table 18 and Table 19).

TABLE 18 mRNA Vaccine Formulation.

Dosage form:
Solution for Injection for IM route of administration

| Composition: Each 0.5 ml Vial Contains: | Quantity | Concentration (mg/ml) |
|---|---|---|
| mRNA | 25 mcg | 0.05 |
| DOTAP | 0.75 mg | 1.5 |
| Iron Oxide Nanoparticles | 0.005 mg | 0.01 |
| Squalene | 0.94 mg | 1.88 |
| Sorbitan Monostearate | 0.93 mg | 1.86 |
| Polysorbate 80 | 0.93 mg | 1.86 |
| Sucrose IP | 50 mg | 100 |
| Citric Acid Monohydrate | 1.05 mg | 2.1 |
| Water for Injection | q.s. to 0.5 ml | |

TABLE 19

Lyophilized mRNA Vaccine Formulation.

Dosage form: Lyophilized powder

| Composition: | Each 5 dose vial contains: | Quantity | Concentration (mg/ml) | Approximate dry weight % |
|---|---|---|---|---|
| | mRNA | 50 mcg | 0.02 | 0.02 |
| | DOTAP | 1.5 mg | 0.6 | 0.57 |
| | Squalene | 1.88 mg | 0.752 | 0.72 |
| | Sorbitan Monostearate | 1.86 mg | 0.744 | 0.71 |
| | Polysorbate 80 | 1.86 mg | 0.744 | 0.71 |
| | Sucrose IP | 250 mg | 100 | 95.3 |
| | Citric Acid Monohydrate | 5.25 mg | 2.1 | 2 |
| | Water for Injection (for reconstitution) | 2.5 ml | | |

Example 12: Evaluation of Lyophilized COVID Vaccines in Mice

The following was performed to assay activity of lyophilized NP-1 with replicon RNA encoded SARS-COV-2 spike antigen sequence, physicochemical properties of reconstituted vaccines, potency, and immunogenicity. Briefly, materials in Table 20 were used.

TABLE 20

Materials.

| Name | Stock concentration |
|---|---|
| NP-1 | 30 mg/ml (measuring DOTAP conc.) |
| NP-7 | 30 mg/ml (measuring DOTAP conc.) |
| repRNA(VEEV)-SARS-CoV2-spike (wild type) encoding variant A.1 RNA sequence | 1687 µg/ml |
| repRNA(VEEV)-SARS- nCoV19-S-Delta.AY1-S2P-wtFur ("Delta-S") encoding variant Delta-preF sequence | 783 µg/ml |
| Sucrose (EMD, Millipore) | — |
| Na-citrate (Teknova) | 1M |

Preparation of formulation complexes. Compositions of lipid nanoparticle/RNA complexes were prepared in this assay as shown below in Table 21. NP-1 or NP-7 and repRNAs were complexed at a N-to-P ratio of 15 and complexed to obtain a final repRNA concentration of 50 mg/ml or 100 mg/ml ("2×" material), and 10% or 20% w/v sucrose content, respectively. Complexed material with 10% sucrose (50 mg/ml repRNA) contained 5 mM sodium citrate while that with 20% sucrose (100 mg/ml repRNA) contained 10 mM citrate. Complexes were filled in 2 ml sterile, depyrogenated and baked vials. Complexes with 10% sucrose were filled at 0.7 ml per vial and 20% sucrose at 0.35 ml per vial. Vials were then either lyophilized and stored or stored as is in liquid form. Storage temperature was 25 degrees C. or 42 degrees C. for 1 week. Quantity of lyophilized and liquid vials per composition is summarized in Table 21.

TABLE 21

Lyophilized and liquid compositions.

| Description | N:P | DOTAP [µg/ml] | RNA [µg/ml] | Volume per vial [ml] | Lyo vials | Liquid vials |
|---|---|---|---|---|---|---|
| NP-1 + WT-S in 10% sucrose | 15 | 1500 | 50 | 0.7 | 8 | 6 |
| NP-1 + Delta-S in 10% sucrose | 15 | 1500 | 50 | 0.7 | 2 | 0 |
| NP-1 + WT-S in 20% sucrose | 15 | 3000 | 100 | 0.35 | 8 | 0 |
| NP-1 + Delta-S in 20% sucrose | 15 | 3000 | 100 | 0.35 | 2 | 0 |
| NP-7 + WT-S in 10% sucrose | 15 | 1500 | 50 | 0.7 | 8 | 6 |

Lyophilization cycle. An SP VirTis Advantage Pro tray and batch lyophilizer with inert gas fill and stoppering capability was used. Summary of the lyophilization cycle is shown in Table 22 below. After end of cycle, vials were backfilled with nitrogen at 48 torr and stoppered, before equilibrating to room pressure.

TABLE 22

Lyophilization cycle.

| Time [hours] | Temp [° C] | Pressure [mT] | Notes |
|---|---|---|---|
| 0 | 5 | 760 | Shelf pre-cooled to 5 degrees C. |
| 0.5 | 5 | 760 | Freezing |
| 2 | −50 | 760 | |
| 2.5 | −50 | 50 | Evacuation |
| 3 | −30 | 50 | Primary drying |
| 20.5 | −30 | 50 | |
| 22.5 | 25 | 50 | Secondary drying |
| 24 | 25 | 50 | |

Condition groups. A summary of 14 groups analyzed in this assay is provided in Table 23 below. Groups 1 and 4, as indicated in the storage column, were prepared fresh to serve as positive controls for comparison with standard protocol for vaccine preparation.

TABLE 23

Condition groups.

| Group | Formulation | RNA | Sucrose [% w/v] | Form | Storage [temp/time] |
|---|---|---|---|---|---|
| 1 | NP-1 | WT-S | 10 | Liquid | Fresh |
| 2 | NP-1 | WT-S | 10 | Liquid | 25 C./1 wk |
| 3 | NP-1 | WT-S | 10 | Liquid | 42 C./1 wk |
| 4 | NP-7 | WT-S | 10 | Liquid | Fresh |
| 5 | NP-7 | WT-S | 10 | Liquid | 25 C./1 wk |
| 6 | NP-7 | WT-S | 10 | Liquid | 42 C./1 wk |
| 7 | NP-1 | WT-S | 10 | Lyo | 25 C./1 wk |
| 8 | NP-1 | WT-S | 10 | Lyo | 42 C./1 wk |
| 9 | NP-1 | WT-S | 20 | Lyo | 25 C./1 wk |
| 10 | NP-1 | WT-S | 20 | Lyo | 42 C./1 wk |
| 11 | NP-7 | WT-S | 10 | Lyo | 25 C./1 wk |
| 12 | NP-7 | WT-S | 10 | Lyo | 42 C./1 wk |
| 13 | NP-1 | Delta-S | 10 | Lyo | 25 C./1 wk |
| 14 | NP-1 | Delta-S | 20 | Lyo | 25 C./1 wk |

Immunogenicity assay. Induction of anti-spike IgG responses were evaluated in 6 to 8 weeks old female C57Bl1/6 mice. A group size of 5 mice was used. The schedule is shown in Table 24.

TABLE 24

Immunogenicity schedule.

| Date | Day | Procedure |
|---|---|---|
| Aug. 23, 2021 | −7 | Lyophilization |
| Sep. 1, 2021 | 0 | Immunization by IM route |
| Sep. 15, 2021 | 14 | Bleed |
| Sep. 29, 2021 | 28 | Bleed |
| Oct. 8, 2021 | 37 | Mice sacrificed |

After 1 week of storage in 25 degrees C. or 42 degrees C. stability chamber, lyophilized nanoparticle/RNA complexes were reconstituted in 0.7 ml sterile milliQ water and gently swirled until no particles were visible to the naked eye. Particle size (z-average) and size distribution (PDI) of the complexes was measured and is summarized in FIG. 17, with group designations shown in Table 25. Particle size and PDI of freshly prepared NP-1/WT-S complex (group 1) was 76.8 nm and 0.223, respectively. After reconstitution, lyophilized samples (groups 7-14) grew by an average of 45% (+/−11%). Summary of % change in z-average relative to group 1 is included in Table 25.

TABLE 25

Percent % change in z-average.

| Group # | 2 | 3 | 4 | 5 | 6 | 7 | 8 | 9 | 10 | 11 | 12 | 13 | 14 |
|---|---|---|---|---|---|---|---|---|---|---|---|---|---|
| % change z-average vs. group 1 | 2% | 0% | 15% | −4% | −1% | 30% | 42% | 59% | 53% | 48% | 33% | 41% | 55% |

Agarose gel electrophoresis of phenol-chloroform extracted repRNA. Liquid formulations of NP-1/repRNA and NP-7+repRNA in 10% sucrose or 20% sucrose, stored for 1 week at NP-1/repRNA and NP-7+repRNA, resulted in partial or full degradation of repRNA product, respectively. (Data not shown.) Lyophilization of NP-1/repRNA and NP-7+repRNA in 10% sucrose or 20% sucrose preserved repRNA integrity after 1 week storage at NP-1/repRNA and NP-7+repRNA. (Data not shown.)

Potency Assay. Lyophilized NP-1/WT-S in 10% sucrose stored for 1 week at 25 degrees C. produced a dose-dependent expression of spike protein in transfected BHK cells. The expression profile was similar to freshly complexed NP-1/WT-S. 1 week storage at 42 degrees C. of lyophilized NP-1/WT-S in 10% sucrose significantly reduced in vitro protein expression. Liquid NP-1/WT-S in 10% sucrose stored for 1 week at 25 degrees C. or 42 degrees C. did not produce spike protein in BHK cells. (Data not shown.)

Anti-D614G spike IgG responses by ELISA. Serum anti-D614G spike IgG levels was assessed on days 14 and 28 post-prime shown below in FIGS. 18A and 18B, respectively. Mouse sera were assayed in an anti-D614G spike ELISA at 1:40 (day 14) or 1:200 (day 28) dilution. Serum IgG level in μg/ml was interpolated from a 4PL standard curve generated by a known concentration of mouse IgG standard.

Day 28 post-prime anti-D614G IgG response. After 1 week at 25 degrees C., liquid NP-1/WT-S in 10% sucrose resulted in a statistically significant reduction in anti-spike IgG compared to the freshly prepared NP-1/WT-S positive control. There was no significant difference in mean IgG levels between freshly prepared NP-1/WT-S and lyophilized NP-1/WT-S in 10% sucrose stored for 1 week at 25 degrees C.

After 1 week at 42 degrees C., lyophilized NP-1/WT-S in 10% sucrose induced 100% seroconversion but mean IgG level was significantly reduced compared to freshly prepared NP-1/WT-S. Summary mean+/−standard deviation IgG concentration data from day 28 post-immunization, including p-values determined by ordinary one-way ANOVA comparing against the freshly prepared NP-1/WT-S positive control, shown in Table 26. $P<0.05$ are considered statistically significant differences.

TABLE 26

| Mean IgG at 1:200 serum dilution. | | | | | | | | |
|---|---|---|---|---|---|---|---|---|
| Group | Formulation | RNA | Sucrose [% | State | Storage temp. and time | D28 mean IgG at 1:200 serum | SD [μg/ml] | P-value vs. group 1 |
| 1 | NP-1 | WT-S | 10 | Liquid | Fresh | 30.38 | 12.29 | n/a |
| 2 | NP-1 | WT-S | 10 | Liquid | 25 C./1 wk | 0.17 | 0.23 | 0.0014 |
| 3 | NP-1 | WT-S | 10 | Liquid | 42 C./1 wk | 0.02 | 0.02 | 0.0013 |
| 4 | NP-7 | WT-S | 10 | Liquid | Fresh | 25.69 | 16.45 | 0.9990 |
| 5 | NP-7 | WT-S | 10 | Liquid | 25 C./1 wk | 8.47 | 15.99 | 0.0385 |
| 6 | NP-7 | WT-S | 10 | Liquid | 42 C./1 wk | 0.00 | 0.00 | 0.0013 |
| 7 | NP-1 | WT-S | 10 | Lyo | 25 C./1 wk | 27.44 | 14.68 | 0.9994 |
| 8 | NP-1 | WT-S | 10 | Lyo | 42 C./1 wk | 7.34 | 10.63 | 0.0257 |
| 9 | NP-1 | WT-S | 20 | Lyo | 25 C./1 wk | 9.07 | 6.41 | 0.0474 |
| 10 | NP-1 | WT-S | 20 | Lyo | 42 C./1 wk | 10.56 | 11.25 | 0.0777 |
| 11 | NP-7 | WT-S | 10 | Lyo | 25 C./1 wk | 27.53 | 24.96 | 0.9994 |
| 12 | NP-7 | WT-S | 10 | Lyo | 42 C./1 wk | 5.33 | 2.68 | 0.0121 |
| 13 | NP-1 | Delta-S | 10 | Lyo | 25 C./1 wk | 25.83 | 6.66 | 0.9990 |
| 14 | NP-1 | Delta-S | 20 | Lyo | 25 C./1 wk | 28.25 | 5.60 | 0.9996 |

Comparison of fresh versus lyophilized formulations. Day 28 post-prime anti-D614G spike IgG concentration in serum is shown in FIG. 19. Statistical differences between mean IgG values were determined by ordinary one-way ANOVA with Dunnett's multiple comparisons test. All groups compared to freshly prepared NP-1/RNA in 10% sucrose. No significant difference was shown between freshly prepared NP-1/RNA and lyophilized NP-1/RNA in 10% sucrose stored for 7 days at 25 degrees C. At 42 degrees C., lyophilized NP-1/RNA in 10% or 20% sucrose induced significantly lower anti-spike IgG compared to freshly prepared NP-1/RNA. Lyophilized NP-1/RNA in 20% sucrose, and stored at 25 degrees C. or 42 degrees C., induced significantly lower IgG than freshly prepared NP-1/WT-S. Lyophilized NP-1/Delta-S in 10% or 20% sucrose, and stored at 25 degrees C., induced similar mean IgG (statistically not significant) than freshly prepared NP-1/WT-S.

All references disclosed herein, including patent references and non-patent references, are hereby incorporated by reference in their entirety as if each was incorporated individually. It is to be understood that the terminology used herein is for the purpose of describing specific embodiments only and is not intended to be limiting. It is further to be understood that unless specifically defined herein, the terminology used herein is to be given its traditional meaning as known in the relevant art.

SEQUENCES

RNA

SEQ ID NO: 1
augcuccucu ugcuccuucu cuugggacuc cgauugcagc
ucucuuuggg uauaauuccu gucgaagaag agaaucccga
cuucuggaau cgcgaagcgg cagaagcauu gggugcggca
aaaaagcucc aaccggcaca gacugcggcc aagaaucuca
uaauuuucuu gggugauggc augggcguuu ccacugugac
ugcggcacga auccugaagg gucaaaagaa ggauaaacug
gguccagaga ucccgcugcc uauggauagg uuuccauacg
uugcgcucuc uaagaccuau aacgucgaua agcauguacc
agacuccgga gcgacggcca cugcuuaccu uuguggaguu
aagguaauu uccaaacaau aggacugagc gcagcugcaa
gauucaacca augcaacacg acaagaggga augaggugau
uucagucaug aaucgagcaa agaaagcugg gaaauccguu
ggcgugguca ccacuacaag agugcagcau gcaucuccag
caggaacuua cgcccacacu guaaacagaa acugguauag
ugacgccgau guucccgccu cugcgaggca agagguugu
caagacaucg cuacccagcu cauaagcaac auggacauug
auguaauacu gggugggggu cggaaauaca guuccggau
gggcacuccc gauccggagu acccggauga cuauucccaa
ggagguacca gauuggacgg gaaaaaucuu guccaagaau
ggcucgccaa gcggcagggg gcaagguacg uguggaacag
gacagaacug augcaggcaa gcuggaucc aagcguaacg
caucuuaugg gucuuuuga acccggugau augaaauacg aaauacaucg cgacucaaca cuggacccgu cucucaugga
gaugacugaa gcugccuuga gguuguugag ucggaaccu
aggggcuuuu ucuuguucgu agagggcggg cgaauugacc
acgucauca cgaaucucga gcguaccggg cgcucacaga
aaccaucaug uuugacgaug cuaucgaacg agcgggucag
cuuaccucug aagaagauac gcucucucuu gucaccgcgg
accauagcca uguuuuucc uucggugguu auccguugcg
agguccagc auauucggcc ucgcgccagg gaaagcccgc
gaccgcaaag cuuuauacggu gcugcuuuac ggaaacggcc
cugguuacgu ccuuaaagac ggugcgagac cugacgugac
ggaaucugaa uccgguucuc ccgaauauag acaacagagu
gcuguccgc uggaugaaga gacucaugcg ggagaagaug
uagcguuuu ugcuagggg ccgcaagcac accuuguuca
uggcguucag gagcaaacuu ucauagccca uguaauggca
uuugcugcgu gucucgagcc guauaccgcu ugcgaucucg
cuccgccggc ggguacaacc gaugcugccc acccgggguga
cucaagagua ggggcagcag ggcgauuuga acaaacu

RNA

SEQ ID NO: 2
augaacaguu ucaguaccuc cgcguucggg ccgguugccu
uuagccuggg gcuucuucug gugcucccg ccgcauuccc
agcgccgguc uucacacucg aagauuucgu uggggacugg
cgacagacag ccggcuacaa ccuggaccaa guccuugaac
agggaggugu guccaguuug uuucagaauc ucggggguc
cguaacuccg auccaaagga uuguccugag cggugaaaau
gggcugaaga ucgacaucca ugucaucauc ccguaugaag
gucugagcgg cgaccaaaug ggccagaucg aaaaaauuuu
uaagguggug uacccugugg augaucauca cuuuaagguug
auccugcacu auggcacacu gguaaucgac ggguuacgc
cgaacaugau cgacuauuuc ggacggccgu augaaggcau
cgccguguuc gacggcaaaa agaucacugu aacagggacc
cuguggaacg gcaacaaaau uaucgacgag cgccugauca
accccgacgg cucccugcug uuccgaguaa ccaucaacgg
agugaccggc uggcggcugu gcgaacgcau ucuggcg

What is claimed is:

1. A dried composition of comprising:
   a) a lipid carrier, wherein the lipid carrier is a nanoemulsion comprising a hydrophobic core, and one or more lipids, wherein the hydrophobic core comprises one or more inorganic nanoparticles, and wherein the one or more inorganic nanoparticles comprise magnetite ($Fe_3O_4$), maghemite ($\gamma$-$Fe_2O_3$), wüstite (FeO), hematite (alpha ($\alpha$)-$Fe_2O_3$), or combinations thereof;
   b) optionally one or more nucleic acids; and
   c) at least one sugar present in an amount of the composition by weight of 80% to 98%.

2. A dried composition comprising:
   a) a lipid carrier, wherein the lipid carrier is a nanoemulsion comprising a hydrophobic core, and one or more lipids;
   b) optionally one or more nucleic acids; and
   c) at least one sugar present in an amount of the composition by weight of 80% to 98%, wherein the at least one sugar is present in an amount of at least about 50 mg.

3. A dried composition comprising:
   a) a lipid carrier, wherein the lipid carrier is a nanoemulsion comprising a hydrophobic core, and one or more lipids, wherein the hydrophobic core further comprises:
   squalene at a concentration of up to about 1.88 mg/ml;
   sorbitan monostearate at a concentration of up to about 1.86 mg/ml;
   polysorbate 80 at a concentration of up to about 1.86 mg/ml; and
   optionally, iron oxide at a concentration of up to about 0.01 mg/ml, b) one or more nucleic acids; and c) at least one sugar present in an amount of the composition by weight of 80% to 98%, wherein:
the one or more nucleic acids is present in an amount of up to about 200 micrograms (μg), the lipid is a cationic lipid that is present in a concentration of up to about 1.5 mg/ml, and the sugar is sucrose that is present in a concentration of up to about 50 mg/ml.

4. The composition of claim 2, further comprising citric acid monohydrate present in a concentration of up to about 2.1 mg/ml.

5. The composition of claim 1, wherein the sugar is present in an amount of the composition by weight of 94% to 96%.

6. The composition of claim 1, wherein the composition is lyophilized.

7. The composition of claim 1, wherein the hydrophobic core comprises an oil.

8. The composition of claim 7, wherein the oil comprises at least one of a-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut/palmkernel oil derived caprylic and capric fatty acids and plant derived glycerol, dihydroisosqualene (DHIS), farnesene and squalane.

9. The composition of claim 1, wherein the one or more lipids is selected from the group consisting of cationic lipids, anionic lipids, neutral lipids, and any combinations thereof.

10. The composition of claim 1, wherein the one or more lipids comprises a cationic lipid.

11. The composition of claim 10, wherein the cationic lipid is selected from the group consisting of 1,2-dioleoyloxy-3-(trimethylammonium)propane (DOTAP); 3β-[N-(N', N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2, 3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis (2-hydroxydodecyl) amino)ethyl) (2-hydroxydodecyl) amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof.

12. The composition of claim 1, wherein the lipid carrier comprises at least one surfactant.

13. The composition of claim 12, wherein the at least one surfactant is selected from the group consisting of a hydrophobic surfactant, a hydrophilic surfactant, and any combinations thereof.

14. The composition of claim 13, wherein the hydrophobic surfactant comprises a sorbitan ester selected from the group consisting of sorbitan monolaurate, sorbitan monopalmitate, sorbitan monostearate, sorbitan tristearate, sorbitan monooleate, and sorbitan trioleate; and the hydrophilic surfactant comprises a polysorbate.

15. The composition of claim 1, wherein the lipid carrier has a z-average hydrodynamic diameter ranging from about 40 nm to about 150 nm, with an average polydispersity index ranging from about 0.1 to about 0.4.

16. The composition of claim 1, wherein the one or more nucleic acids comprise DNA or RNA.

17. The composition of claim 1, wherein the one or more nucleic acids are incorporated or complexed with the lipid carrier to form a lipid carrier-nucleic acid complex.

18. The composition of claim 1, wherein the at least one sugar is selected from the group consisting of sucrose, maltose, trehalose, mannitol, glucose, and any combinations thereof.

19. The composition of claim 3, further comprising citric acid monohydrate present in a concentration of up to about 2.1 mg/ml.

20. The composition of claim 3, wherein the sugar is present in an amount of the composition by weight of 94% to 96%.

21. The composition of claim 3, wherein the composition is lyophilized.

22. The composition of claim 3, wherein the one or more nucleic acids comprise DNA or RNA.

23. The composition of claim 3, wherein the one or more nucleic acids are incorporated or complexed with the lipid carrier to form a lipid carrier-nucleic acid complex.

24. The composition of claim 3, wherein the at least one sugar is selected from the group consisting of sucrose, maltose, trehalose, mannitol, glucose, and any combinations thereof.

25. The composition of claim 2, wherein the sugar is present in amount of the composition by weight of 94% to 96%.

26. The composition of claim 2, wherein the composition is lyophilized.

27. The composition of claim 2, wherein the composition is thermally stable at about-20 degrees Celsius.

28. The composition of claim 2, wherein the composition is thermally stable at about 2 degrees Celsius to about 8 degrees Celsius.

29. The composition of claim 2, wherein the composition is thermally stable at about 25 degrees Celsius.

30. The composition of claim 2, wherein the composition is thermally stable at about 45 degrees Celsius.

31. The composition of claim 2, wherein the composition is thermally stable for at least 1 week.

32. The composition of claim 2, wherein the hydrophobic core comprises an oil.

33. The composition of claim 32, wherein the oil comprises at least one of a-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut/palmkernel oil derived caprylic and capric fatty acids and plant derived glycerol, dihydroisosqualene (DHIS), farnesene and squalane.

34. The composition of claim 2, wherein the one or more lipids is selected from the group consisting of cationic lipids, anionic lipids, neutral lipids, and any combinations thereof.

35. The composition of claim 34, wherein the one or more lipids comprises a cationic lipid.

36. The composition of claim 34, wherein the cationic lipid is selected from the group consisting of 1,2-dioleoyloxy-3-(trimethylammonium) propane (DOTAP); 3β-[N-(N',N'-dimethylaminoethane)-carbamoyl]cholesterol (DC Cholesterol); dimethyldioctadecylammonium (DDA); 1,2- dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis (2-hydroxydodecyl) amino)ethyl) (2-hydroxydodecyl) amino)ethyl)piperazin-1-yl)ethyl)azanediyl)bis (dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof.

37. The composition of claim 2, wherein the lipid carrier comprises at least one surfactant.

38. The composition of claim 37, wherein the at least one surfactant is selected from the group consisting of a hydrophobic surfactant, a hydrophilic surfactant, and any combinations thereof.

39. The composition of claim 38, wherein the hydrophobic surfactant comprises a sorbitan ester selected from the group consisting of sorbitan monolaurate, sorbitan monopalmitate, sorbitan monostearate, sorbitan tristearate, sorbitan monooleate, and sorbitan trioleate; and the hydrophilic surfactant comprises a polysorbate.

40. The composition of claim 2, wherein the lipid carrier has a z-average hydrodynamic diameter ranging from about 40 nm to about 150 nm, with an average polydispersity index ranging from about 0.1 to about 0.4.

41. The composition of claim 2, wherein the one or more nucleic acids comprise DNA or RNA.

42. The composition of claim 41, wherein the RNA is a self-replicating RNA.

43. The composition of claim 2, wherein the one or more nucleic acids are incorporated or complexed with the lipid carrier to form a lipid carrier-nucleic acid complex.

44. The composition of claim 43, wherein the lipid carrier-nucleic acid complex is formed via non-covalent interactions or via reversible covalent interactions.

45. The composition of claim 2, wherein a molar ratio of the lipid carrier to the one or more nucleic acids, characterized by a nitrogen-to-phosphate (N:P) molar ratio, ranges from about 1:1 to about 150:1.

46. The composition of claim 2, wherein the at least one sugar is selected from the group consisting of sucrose, maltose, trehalose, mannitol, glucose, and any combinations thereof.

47. The composition of claim 2, wherein the at least one sugar comprises sucrose.

* * * * *